US005106965A

United States Patent [19]

Pieniazek et al.

[11] Patent Number: 5,106,965

[45] Date of Patent: Apr. 21, 1992

[54] DETECTION OF HUMAN ADENOVIRUS

[75] Inventors: Norman J. Pieniazek, Suwanee; Susan B. Slemenda, Decatur; Danuta Pieniazek, Suwanee, all of Ga.; Jorge Velarde, Jr., San Diego, Calif.; Ronald B. Luftig, Metairie, La.

[73] Assignee: Research Corporation Technologies, Inc., Tucson, Ariz.

[21] Appl. No.: 507,421

[22] Filed: Apr. 9, 1990

Related U.S. Application Data

[63] Continuation-in-part of Ser. No. 442,027, Nov. 27, 1989, abandoned.

[51] Int. Cl.[5] .......... C12Q 1/70; C07K 3/00

[52] U.S. Cl. .......... 536/27; 435/5; 530/350

[58] Field of Search .......... 435/5; 536/27; 530/350

[56] References Cited

U.S. PATENT DOCUMENTS 4,882,282 11/1989 Anderson et al. .......... 435/252.3

4,968,607 11/1990 Dower et al. .......... 435/69.1

*Primary Examiner*—Robert A. Wax

*Assistant Examiner*—Bradley L. Sisson

*Attorney, Agent, or Firm*—Scully, Scott, Murphy & Presser

[57] ABSTRACT

The present invention relates to DNA and proteins of human adenovirus Type 41 and their use in detection of said virus. More specifically, the present invention relates to the isolation of a 41.4 kd short fiber protein and a 60.6 kd long fiber protein of adenovirus type 41 (Ad41), as well as proteins derived from the Ad41 E3 region, thereby providing virus-derived antigens and active derivatives and parts thereof, useful in the development of diagnostic assays, DNA probes and vaccines for said virus or other related viruses belonging to the human enteric adenovirus family. In addition, the present invention is directed to recombinant DNA molecules containing the human enteric adenovirus Type 41 Tak long fiber protein gene, the Ad41 short fiber protein gene and the Ad41 E3 gene (encoding the Ad41 proteins RL-1 to RL-6) thereby providing a source of recombinant viral components useful in the development of said diagnostic assays, DNA probes and vaccines for human adenoviruses. The present invention is also directed to first antibodies specific to the above-identified Ad41 viral components and to second antibodies specific to the first antibodies. These second antibodies are also useful in the development of diagnostic assays for Ad41 and other adenoviruses.

40 Claims, 24 Drawing Sheets

```
        10        20        30        40        50        60
         *         *         *         *         *         *
CCCGGGCAAC ATGCTCATCC AAATCTCGCC TAACATCACC TTCAGTGTCG TCTACAACGA
GGGCCCGTTG TACGAGTAGG TTTAGAGCGG ATTGTAGTGG AAGTCACAGC AGATGTTGCT
SmaI

        70        80        90       100       110       120
         *         *         *         *         *         *
GATAAACAGT GGGTATGCTT TTACTTTTAA ATGGTCAGCC GAACCGGGAA AACCTTTTCA
CTATTTGTCA CCCATACGAA AATGAAAATT TACCAGTCGG CTTGGCCCTT TTGGAAAAGT

       130       140       150       160       170       180
         *         *         *         *         *         *
CCCACCTACC GCTGTATTTT GCTACATAAC TGAACAATAA AATCATTGCA GGCACAATCT
GGGTGGATGG CGACATAAAA CGATGTATTG ACTTGTTATT TTAGTAACGT CCGTGTTAGA

       190       200           210           220           230
         *         *           *           *           *
TCGCATTTCT TTTTTTCCAG ATG AAA CGA GCC AGA CTT GAA GAT GAC TTC AAC CCC
AGCGTAAAGA AAAAAAGGTC TAC TTT GCT CGG TCT GAA CTT CTA CTG AAG TTG GGG
                      Met Lys Arg Ala Arg Leu Glu Asp Asp Phe Asn Pro
                      ____________60.6 KD FIBER PROTEIN______________

 240         250         260           270         280
  *           *           *             *           *
GTC TAC CCT TAC GAA CAC TAC AAT CCC CTT GAC ATC CCA TTT ATT ACA CCC
CAG ATG GGA ATG CTT GTG ATG TTA GGG GAA CTG TAG GGT AAA TAA TGT GGG
Val Tyr Pro Tyr Glu His Tyr Asn Pro Leu Asp Ile Pro Phe Ile Thr Pro
______________________60.6 KD FIBER PROTEIN________________________

290          300         310         320           330
 *            *           *           *             *
CCG TTT GCC TCC TCC AAC GGC TTG CAA GAA AAA CCA CCG GGA GTC CTC AGC
GGC AAA CGG AGG AGG TTG CCG AAC GTT CTT TTT GGT GGC CCT CAG GAG TCG
Pro Phe Ala Ser Ser Asn Gly Leu Gln Glu Lys Pro Pro Gly Val Leu Ser
______________________60.6 KD FIBER PROTEIN________________________

340         350          360         370         380
 *           *            *           *           *
CTG AAA TAC ACT GAT CCA CTT ACA ACC AAA AAC GGG GCT TTA ACC TTA AAA
GAC TTT ATG TGA CTA GGT GAA TGT TGG TTT TTG CCC CGA AAT TGG AAT TTT
Leu Lys Tyr Thr Asp Pro Leu Thr Thr Lys Asn Gly Ala Leu Thr Leu Lys
______________________60.6 KD FIBER PROTEIN________________________
```

FIG. 1A 1B 1B

```
      390         400         410         420         430         440
       *           *           *           *           *           *
     CTG GGC ACG GGA CTA AAC ATT GAT GAA AAT GGA GAT CTT TCT TCA GAT GCT
     GAC CCG TGC CCT GAT TTG TAA CTA CTT TTA CCT CTA GAA AGA AGT CTA CGA
     Leu Gly Thr Gly Leu Asn Ile Asp Glu Asn Gly Asp Leu Ser Ser Asp Ala
                            ____60.6 KD FIBER PROTEIN____
                450         460         470         480         490
                 *           *           *           *           *
     AGC GTG GAA GTT AGC GCC CCT ATT ACT AAA ACC AAC AAA ATC GTA GGT TTA
     TCG CAC CTT CAA TCG CGG GGA TAA TGA TTT TGG TTG TTT TAG CAT CCA AAT
     Ser Val Glu Val Ser Ala Pro Ile Thr Lys Thr Asn Lys Ile Val Gly Leu
                            ____60.6 KD FIBER PROTEIN____

          500         510         520         530         540
           *           *           *           *           *
     AAT TAC ACT AAA CCT CTC GCC CTG CGA AGT AAC GCG CTC ACT CTT TCT TAC
     TTA ATG TGA TTT GGA GAG CGG GAC GCT TCA TTG CGC GAG TGA GAA AGA ATG
     Asn Tyr Thr Lys Pro Leu Ala Leu Arg Ser Asn Ala Leu Thr Leu Ser Tyr
                         ____60.6 KD FIBER PROTEIN____

          550         560         570         580         590
           *           *           *           *           *
     AAC GCA CCC TTA AAC GTA GTA AAT AAC AAT TTA GCT TTA AAT ATC TCA CAA
     TTG CGT GGG AAT TTG CAT CAT TTA TTG TTA AAT CGA AAT TTA TAG AGT GTT
     Asn Ala Pro Leu Asn Val Val Asn Asn Asn Leu Ala Leu Asn Ile Ser Gln
                         ____60.6 KD FIBER PROTEIN____

          600         610         620         630         640
           *           *           *           *           *
     CCT GTC ACT GTT AAT GCA AAC AAC GAA CTT TCT CTC TTA ATA GAC GCC CCA
     GGA CAG TGA CAA TTA CGT TTG TTG CTT GAA AGA GAG AAT TAT CTG CGG GGT
     Pro Val Thr Val Asn Ala Asn Asn Glu Leu Ser Leu Leu Ile Asp Ala Pro
                         ____60.6 KD FIBER PROTEIN____

          650         660         670         680         690
           *           *           *           *           *
     CTT AAT GCT GAC ACG GGC ACT CTT CGC CTT CAA AGT GCT GCA CCT CTT GGA
     GAA TTA CGA CTG TGC CCG TGA GAA GCG GAA GTT TCA CGA CGT GGA GAA CCT
     Leu Asn Ala Asp Thr Gly Thr Leu Arg Leu Gln Ser Ala Ala Pro Leu Gly
                         ____60.6 KD FIBER PROTEIN____

          700         710         720         730         740
           *           *           *           *           *
     CTA GTG GAC AAA ACA CTA AAA GTT TTG TTT TCT AGC CCC CTC TAT CTA GAT
     GAT CAC CTG TTT TGT GAT TTT CAA AAC AAA AGA TCG GGG GAG ATA GAT CTA
     Leu Val Asp Lys Thr Leu Lys Val Leu Phe Ser Ser Pro Leu Tyr Leu Asp
                         ____60.6 KD FIBER PROTEIN____
```

FIG.1B 1B 1B 750 760 770 780 790

AAT AAC TTT CTT ACA CTA GCC ATT GAA CGC CCG CTA GCT CTA TCC AGT AGC
TTA TTG AAA GAA TGT GAT CGG TAA CTT GCG GGC GAT CGA GAT AGG TCA TCG
Asn Asn Phe Leu Thr Leu Ala Ile Glu Arg Pro Leu Ala Leu Ser Ser Ser
60.6 KD FIBER PROTEIN 800 810 820 830 840

AGA GCA GTG ACC CTT AAG TAT TCA CCA CCT TTA AAA ATA GAA AAC GAA AAC
TCT CGT CAC TGG GAA TTC ATA AGT GGT GGA AAT TTT TAT CTT TTG CTT TTG
Arg Ala Val Thr Leu Lys Tyr Ser Pro Pro Leu Lys Ile Glu Asn Glu Asn
60.6 KD FIBER PROTEIN 850 860 870 880 890

TTA ACC CTA AGC ACA GGC GGG CCT TTT ACT GTA AGC GGG GGA AAT CTA AAC
AAT TGG GAT TCG TGT CCG CCC GGA AAA TGA CAT TCG CCC CCT TTA GAT TTG
Leu Thr Leu Ser Thr Gly Gly Pro Phe Thr Val Ser Gly Gly Asn Leu Asn
60.6 KD FIBER PROTEIN 900 910 920 930 940 950

TTA ACA ACA TCG GCA CCT CTC TCC GTG CAA AAC AAC TCT CTC TCC TTA GTC
AAT TGT TGT AGC CGT GGA GAG AGG CAC GTT TTG TTG AGA GAG AGG AAT CAG
Leu Thr Thr Ser Ala Pro Leu Ser Val Gln Asn Asn Ser Leu Ser Leu Val
60.6 KD FIBER PROTEIN 960 970 980 990 1000

ATT ACT TCT CCT TTA AAA GTT ATT AAT TCT ATG TTA GCC GTT GGG GTT AAC
TAA TGA AGA GGA AAT TTT CAA TAA TTA AGA TAC AAT CGG CAA CCC CAA TTG
Ile Thr Ser Pro Leu Lys Val Ile Asn Ser Met Leu Ala Val Gly Val Asn
60.6 KD FIBER PROTEIN 1010 1020 1030 1040 1050

CCG CCT TTT ACC ATC ACT GAC TCT GGA TTA GCT ATG GAC TTA GGA GAC GGT
GGC GGA AAA TGG TAG TGA CTG AGA CCT AAT CGA TAC CTG AAT CCT CTG CCA
Pro Pro Phe Thr Ile Thr Asp Ser Gly Leu Ala Met Asp Leu Gly Asp Gly
60.6 KD FIBER PROTEIN

FIG. 1C 1D 1D

```
            1060          1070          1080          1090          1100
       *      *      *      *      *      *      *      *      *      *
      CTT    GCA    CTA    GGT    GGC    TCT    AAG    TTA    ATA    ATC    AAT    CTT    GGT    CCA    GGT    TTA    CAA
      GAA    CGT    GAT    CCA    CCG    AGA    TTC    AAT    TAT    TAG    TTA    GAA    CCA    GGT    CCA    AAT    GTT
      Leu    Ala    Leu    Gly    Gly    Ser    Lys    Leu    Ile    Ile    Asn    Leu    Gly    Pro    Gly    Leu    Gln
                                        ____60.6 KD FIBER PROTEIN_____

            1110          1120          1130          1140          1150
       *      *      *      *      *      *      *      *      *      *
      ATG    TCT    AAT    GGA    GCT    ATT    ACT    TTA    GCA    CTA    GAT    GCA    GCG    CTG    CCT    TTG    CAA
      TAC    AGA    TTA    CCT    CGA    TAA    TGA    AAT    CGT    GAT    CTA    CGT    CGC    GAC    GGA    AAC    GTT
      Met    Ser    Asn    Gly    Ala    Ile    Thr    Leu    Ala    Leu    Asp    Ala    Ala    Leu    Pro    Leu    Gln
                                        ____60.6 KD FIBER PROTEIN_____

            1160          1170          1180          1190          1200
       *      *      *      *      *      *      *      *      *      *      *
      TAT    AGA    GAC    AAC    CAA    CTT    CAA    CTC    AGA    ATT    GGC    TCA    ACA    TCT    GGC    TTA    ATT
      ATA    TCT    CTG    TTG    GTT    GAA    GTT    GAG    TCT    TAA    CCG    AGT    TGT    AGA    CCG    AAT    TAA
      Tyr    Arg    Asp    Asn    Gln    Leu    Gln    Leu    Arg    Ile    Gly    Ser    Thr    Ser    Gly    Leu    Ile
                                        ____60.6 KD FIBER PROTEIN_____

       1210          1220          1230          1240          1250
       *      *      *      *      *      *      *      *      *      *
      ATG    AGC    GGA    GTA    ACA    CAA    ACA    TTA    AAC    GTC    AAT    GCC    AAT    ACC    GGC    AAA    GGT
      TAC    TCG    CCT    CAT    TGT    GTT    TGT    AAT    TTG    CAG    TTA    CGG    TTA    TGG    CCG    TTT    CCA
      Met    Ser    Gly    Val    Thr    Gln    Thr    Leu    Asn    Val    Asn    Ala    Asn    Thr    Gly    Lys    Gly
                                        ____60.6 KD FIBER PROTEIN_____

       1260          1270          1280          1290          1300
       *      *      *      *      *      *      *      *      *      *
      CTT    GCT    GTT    GAA    AAC    AAC    TCA    CTA    GTT    GTT    AAG    CTT    GGG    AAC    GGT    CTT    CGC
      GAA    CGA    CAA    CTT    TTG    TTG    AGT    GAT    CAA    CAA    TTC    GAA    CCC    TTG    CCA    GAA    GCG
      Leu    Ala    Val    Glu    Asn    Asn    Ser    Leu    Val    Val    Lys    Leu    Gly    Asn    Gly    Leu    Arg
                                        ____60.6 KD FIBER PROTEIN_____

      1310          1320          1330          1340          1350
       *      *      *      *      *      *      *      *      *      *
      TTT    GAT    AGC    TGG    GGA    AGC    ATA    ACT    GTC    TCG    CCT    ACT    ACC    ACT    ACC    CCT    ACC
      AAA    CTA    TCG    ACC    CCT    TCG    TAT    TGA    CAG    AGC    GGA    TGA    TGG    TGA    TGG    GGA    TGG
      Phe    Asp    Ser    Trp    Gly    Ser    Ile    Thr    Val    Ser    Pro    Thr    Thr    Thr    Thr    Pro    Thr
                                        ____60.6 KD FIBER PROTEIN_____

      1360          1370          1380          1390          1400
       *      *      *      *      *      *      *      *      *      *
      ACC    CTA    TGG    ACC    ACC    GCA    GAC    CCA    TCA    CCT    AAC    GCC    ACT    TTT    TAT    GAA    TCA
      TGG    GAT    ACC    TGG    TGG    CGT    CTG    GGT    AGT    GGA    TTG    CGG    TGA    AAA    ATA    CTT    AGT
      Thr    Leu    Trp    Thr    Thr    Ala    Asp    Pro    Ser    Pro    Asn    Ala    Thr    Phe    Tyr    Glu    Ser
                                        ____60.6 KD FIBER PROTEIN_____
```

FIG.ID

```
       1410         1420         1430         1440         1450         1460
         *            *            *            *            *            *
      CTA GAC GCC AAA GTG TGG CTA GTT TTA GTA AAA TGC AAC GGC ATG GTT AAC
      GAT CTG CGG TTT CAC ACC GAT CAA AAT CAT TTT ACG TTG CCG TAC CAA TTG
      Leu Asp Ala Lys Val Trp Leu Val Leu Val Lys Cys Asn Gly Met Val Asn
      _____60.6 KD FIBER PROTEIN_____

              1470         1480         1490         1500         1510
                *            *            *            *            *
      GGG ACC ATA TCC ATT AAA GCT CAG AAA GGC ATT TTA CTT AGA CCT ACA GCT
      CCC TGG TAT AGG TAA TTT CGA GTC TTT CCG TAA AAT GAA TCT GGA TGT CGA
      Gly Thr Ile Ser Ile Lys Ala Gln Lys Gly Ile Leu Leu Arg Pro Thr Ala
      _____60.6 KD FIBER PROTEIN_____

              1520         1530         1540         1550         1560
                *            *            *            *            *
      AGT TTT ATT TCC TTT GTC ATG TAT TTC TAC AGC GAT GGA ACA TGG AGA AAA
      TCA AAA TAA AGG AAA CAG TAC ATA AAG ATG TCG CTA CCT TGT ACC TCT TTT
      Ser Phe Ile Ser Phe Val Met Tyr Phe Tyr Ser Asp Gly Thr Trp Arg Lys
      _____60.6 KD FIBER PROTEIN_____

              1570         1580         1590         1600         1610
                *            *            *            *            *
      AAC TAT CCC GTG TTT GAC AAC GAA GGG ATA CTA GCA AAC AGT GCC ACG TGG
      TTG ATA GGG CAC AAA CTG TTG CTT CCC TAT GAT CGT TTG TCA CGG TGC ACC
      Asn Tyr Pro Val Phe Asp Asn Glu Gly Ile Leu Ala Asn Ser Ala Thr Trp
      _____60.6 KD FIBER PROTEIN_____

              1620         1630         1640         1650         1660
                *            *            *            *            *
      GGT TAT CGA CAA GGA CAG TCT GCC AAC ACT AAC GTT TCT AAT GCT GTA GAA
      CCA ATA GCT GTT CCT GTC AGA CGG TTG TGA TTG CAA AGA TTA CGA CAT CTT
      Gly Tyr Arg Gln Gly Gln Ser Ala Asn Thr Asn Val Ser Asn Ala Val Glu
      _____60.6 KD FIBER PROTEIN_____

              1670         1680         1690         1700         1710
                *            *            *            *            *
      TTT ATG CCT AGC TCT AAA AGA TAT CCC AAT CAA AAA GGT TCT GAA GTT CAG
      AAA TAC GGA TCG AGA TTT TCT ATA GGG TTA GTT TTT CCA AGA CTT CAA GTC
      Phe Met Pro Ser Ser Lys Arg Tyr Pro Asn Gln Lys Gly Ser Glu Val Gln
      _____60.6 KD FIBER PROTEIN_____
```

```
 1720        1730        1740        1750        1760
AAC ATG GCT CTT ACC TAC ACT TTT TTG CAA GGT GAT CCT AAC ATG GCC ATA
TTG TAC CGA GAA TGG ATG TGA AAA AAC GTT CCA CTA GGA TTG TAC CGG TAT
Asn Met Ala Leu Thr Tyr Thr Phe Leu Gln Gly Asp Pro Asn Met Ala Ile
_____________________60.6 KD FIBER PROTEIN_______________________

 1770        1780        1790        1800        1810
TCC TTT CAG AGT ATT TAT AAT CAT GCA TTA GAA GGC TAC TCA TTA AAA TTT
AGG AAA GTC TCA TAA ATA TTA GTA CGT AAT CTT CCG ATG AGT AAT TTT AAA
Ser Phe Gln Ser Ile Tyr Asn His Ala Leu Glu Gly Tyr Ser Leu Lys Phe
_____________________60.6 KD FIBER PROTEIN_______________________

1820        1830        1840        1850        1860
ACC TGG CGC GTT CGA AAT AAT GAA CGT TTT GAC ATC CCC TGC TGC TCA TTT
TGG ACC GCG CAA GCT TTA TTA CTT GCA AAA CTG TAG GGG ACG ACG AGT AAA
Thr Trp Arg Val Arg Asn Asn Glu Arg Phe Asp Ile Pro Cys Cys Ser Phe
_____________________60.6 KD FIBER PROTEIN_______________________

1870        1880        1890        1900        1910        1920
TCT TAT GTA ACA GAA CAA TAA A ATATTGTTGT TTTTGTTTTT ATAACTTTAT
AGA ATA CAT TGT CTT GTT ATT T TATAACAACA AAAACAAAAA TATTGAAATA
Ser Tyr Val Thr Glu Gln End
___60.6 KD FIBER PROTEI____

      1930
TGATACTTTT ACAGAATTC
ACTATGAAAA TGTCTTAAG
               EcoRI
```

FIG. 1F

```
        10         20         30         40         50         60
    *    *     *    *     *    *     *    *     *    *     *    *
GATATCAGTT GTTTGTCAAG TTTTTCCAGC AGCACCACCT GCCCTTCCTC CCAACTTTCG
CTATAGTCAA CAAACAGTTC AAAAAGGTCG TCGTGGTGGA CGGGAAGGAG GGTTGAAAGC

        70         80         90        100        110        120
    *    *     *    *     *    *     *    *     *    *     *    *
TAGGGGATGT GCCAACGGGC AGCAAACTTT CTCCACGTCC TAAAGGGTAT ATCGGTGTTC
ATCCCCTACA CGGTTGCCCG TCGTTTGAAA GAGGTGCAGG ATTTCCCATA TAGCCACAAG

       130        140        150        160        170        180
    *    *     *    *     *    *     *    *     *    *     *    *
ACCTTTTTAC CCTGACCCAC GATCTTCATC TTGCAGATGA AAAGAACCAG AATTGAAGAC
TGGAAAAATG GGACTGGGTG CTAGAAGTAG AACGTCTACT TTTCTTGGTC TTAACTTCTG

       190        200        210        220        230        240
    *    *     *    *     *    *     *    *     *    *     *    *
GACTTCAACC CCGTCTACCC CTATGACACC TTCTCAACTC CCAGCATCCC CTATGTAGCT
CTGAAGTTGG GGCAGATGGG GATACTGTGG AAGAGTTGAG GGTCGTAGGG GATACATCGA

       250        260        270        280        290        300
    *    *     *    *     *    *     *    *     *    *     *    *
CCGCCCTTCG TTTCTTCTGA CGGGTTACAG GAAAAACCCC CAGGAGTTTT AGCACTCAAG
GGCGGGAAGC AAAGAAGACT GCCCAATGTC CTTTTTGGGG GTCCTCAAAA TCGTGAGTTC

       310        320        330        340        350        360
    *    *     *    *     *    *     *    *     *    *     *    *
TACACTGACC CCATTACTAC CAATGCTAAG CATGAGCTTA CTTTAAAACT TGGAAGCAAC
ATGTGACTGG GGTAATGATG GTTACGATTC GTACTCGAAT GAAATTTTGA ACCTTCGTTG

       370        380        390        400        410        420
    *    *     *    *     *    *     *    *     *    *     *    *
ATAACTTTAG AAAATGGGTT ACTTTCGGCC ACAGTTCCCA CTGTTTCTCC TCCCCTTACA
TATTGAAATC TTTTACCCAA TGAAAGCCGG TGTCAAGGGT GACAAAGAGG AGGGGAATGT

       430        440        450        460        470        480
    *    *     *    *     *    *     *    *     *    *     *    *
AACAGTAACA ACTCCCTGGG TTTAGCCACA TCCGCTCCCA TAGCTGTATC AGCTAACTCT
TTGTCATTGT TGAGGGACCC AAATCGGTGT AGGCGAGGGT ATCGACATAG TCGATTGAGA
```

FIG. 2A 2B 2B 2A 2A

```
       490        500        510        520        530        540
    *    *     *    *     *    *     *    *     *    *     *    *
CTCACATTGG CCACCGCCGC ACCACTGACA GTAAGCAACA ACCAGCTTAG TATTAACGCG
GAGTGTAACC GGTGGCGGCG TGGTGACTGT CATTCGTTGT TGGTCGAATC ATAATTGCGC

       550        560        570        580        590        600
    *    *     *    *     *    *     *    *     *    *     *    *
GGCAGAGGTT TAGTTATAAC TAACAATGCC TTAACAGTTA ATCCTACCGG AGCGCTAGGT
CCGTCTCCAA ATCAATATTG ATTGTTACGG AATTGTCAAT TAGGATGGCC TCGCGATCCA

       610        620        630        640        650        660
    *    *     *    *     *    *     *    *     *    *     *    *
TTCAATAACA CAGGAGCTTT ACAATTAAAT GCTGCAGGAG GAATGAGAGT GGACGGTGCC
AAGTTATTGT GTCCTCGAAA TGTTAATTTA CGACGTCCTC CTTACTCTCA CCTGCCACGG

       670        680        690        700        710        720
    *    *     *    *     *    *     *    *     *    *     *    *
AACTTAATTC TTCATGTAGC ATATCCCTTT GAAGCAATCA ACCAGCTAAC ACTGCGATTA
TTGAATTAAG AAGTACATCG TATAGGGAAA CTTCGTTAGT TGGTCGATTG TGACGCTAAT

       730        740        750        760        770        780
    *    *     *    *     *    *     *    *     *    *     *    *
GAAAACGGGT TAGAAGTAAC CAGCGGAGGA AAGCTTAACG TTAAGTTGGG ATCAGGCCTC
CTTTTGCCCA ATCTTCATTG GTCGCCTCCT TTCGAATTGC AATTCAACCC TAGTCCGGAG

       790        800        810        820        830        840
    *    *     *    *     *    *     *    *     *    *     *    *
CAATTTGACA GTAACGGACG CATTGCTATT AGTAATAGCA ACCGAACTCG AAGTGTACCA
GTTAAACTGT CATTGCCTGC GTAACGATAA TCATTATCGT TGGCTTGAGC TTCACATGGT

       850        860        870        880        890        900
    *    *     *    *     *    *     *    *     *    *     *    *
TCCCTCACTA CCATTTGGTC TATCTCGCCT ACGCCTAACT GCTCCATTTA TGAAACCCAA
AGGGAGTGAT GGTAAACCAG ATAGAGCGGA TGCGGATTGA CGAGGTAAAT ACTTTGGGTT

       910        920        930        940        950        960
    *    *     *    *     *    *     *    *     *    *     *    *
GATGCAAACC TATTTCTTTG TCTAACTAAA AACGGAGCTC ACGTATTAGG TACTATAACA
CTACGTTTGG ATAAAGAAAC AGATTGATTT TTGCCTCGAG TGCATAATCC ATGATATTGT

       970        980        990       1000       1010       1020
    *    *     *    *     *    *     *    *     *    *     *    *
ATCAAAGGTC TTAAAGGAGC ACTGCGGGAA ATGCACGATA ACGCTCTATC TTTAAAACTT
TAGTTTCCAG AATTTCCTCG TGACGCCCTT TACGTGCTAT TGCGAGATAG AAATTTTGAA
```

FIG. 2B 2C 2C

```
       1030       1040       1050       1060       1070       1080
     *    *     *    *     *    *     *    *     *    *     *    *
CCCTTTGACA ATCAGGGAAA TTTACTTAAC TGTGCCTTGG AATCATCCAC CTGGCGTTAC
GGGAAACTGT TAGTCCCTTT AAATGAATTG ACACGGAACC TTAGTAGGTG GACCGCAATG

       1090       1100       1110       1120       1130       1140
     *    *     *    *     *    *     *    *     *    *     *    *
CAGGAAACCA ACGCAGTGGC CTCTAATGCC TTAACATTTA TGCCCAACAG TACAGTGTAT
GTCCTTTGGT TGCGTCACCG GAGATTACGG AATTGTAAAT ACGGGTTGTC ATGTCACATA

       1150       1160       1170       1180       1190       1200
     *    *     *    *     *    *     *    *     *    *     *    *
CCACGAAACA AAACCGCTCA CCCGGGCAAC ATGCTCATCC AAATCTCGCC TAACATCACC
GGTGCTTTGT TTTGGCGAGT GGGCCCGTTG TACGAGTAGG TTTAGAGCGG ATTGTAGTGG

       1210       1220       1230       1240       1250       1260
     *    *     *    *     *    *     *    *     *    *     *    *
TTCAGTGTCG TCTACAACGA GATAAACAGT GGGTATGCTT TTACTTTTAA ATGGTCAGCC
AAGTCACAGC AGATGTTGCT CTATTTGTCA CCCATACGAA AATGAAAATT TACCAGTCGG

       1270       1280       1290       1300       1310       1320
     *    *     *    *     *    *     *    *     *    *     *    *
GAACCGGGAA AACCTTTTCA CCCACCTACC GCTGTATTTT GCTACATAAC TGAACAATAA
CTTGGCCCTT TTGGAAAAGT GGGTGGATGG CGACATAAAA CGATGTATTG ACTTGTTATT

       1330       1340       1350       1360       1370       1380
     *    *     *    *     *    *     *    *     *    *     *    *
AATCATTGCA GGCACAATCT TCGCATTTCT TTTTTTCCAG ATGAAACGAG CCAGACTTGA
TTAGTAACGT CCGTGTTAGA AGCGTAAAGA AAAAAAGGTC TACTTTGCTC GGTCTGAACT

       1390       1400
     *    *     *    *
AGATGACTTC AACCCCGTCT AC
TCTACTGAAG TTGGGGCAGA TG
```

FIG.2C

Met Lys Arg Thr Arg Ile Glu Asp Asp Phe Asn Pro Val Tyr Pro Tyr Asp
Thr Phe Ser Thr Pro Ser Ile Pro Tyr Val Ala Pro Pro Phe Val Ser Ser
Asp Gly Leu Gln Glu Lys Pro Pro Gly Val Leu Ala Leu Lys Tyr Thr Asp
Pro Ile Thr Thr Asn Ala Lys His Glu Leu Thr Leu Lys Leu Gly Ser Asn
Ile Thr Leu Glu Asn Gly Leu Leu Ser Ala Thr Val Pro Thr Val Ser Pro
Pro Leu Thr Asn Ser Asn Asn Ser Leu Gly Leu Ala Thr Ser Ala Pro Ile
Ala Val Ser Ala Asn Ser Leu Thr Leu Ala Thr Ala Ala Pro Leu Thr Val
Ser Asn Asn Gln Leu Ser Ile Asn Ala Gly Arg Gly Leu Val Ile Thr Asn
Asn Ala Leu Thr Val Asn Pro Thr Gly Ala Leu Gly Phe Asn Asn Thr Gly
Ala Leu Gln Leu Asn Ala Ala Gly Gly Met Arg Val Asp Gly Ala Asn Leu
Ile Leu His Val Ala Tyr Pro Phe Glu Ala Ile Asn Gln Leu Thr Leu Arg
Leu Glu Asn Gly Leu Glu Val Thr Ser Gly Gly Lys Leu Asn Val Lys Leu
Gly Ser Gly Leu Gln Phe Asp Ser Asn Gly Arg Ile Ala Ile Ser Asn Ser
Asn Arg Thr Arg Ser Val Pro Ser Leu Thr Thr Ile Trp Ser Ile Ser Pro
Thr Pro Asn Cys Ser Ile Tyr Glu Thr Gln Asp Ala Asn Leu Phe Leu Cys
Leu Thr Lys Asn Gly Ala His Val Leu Gly Thr Ile Thr Ile Lys Gly Leu
Lys Gly Ala Leu Arg Glu Met His Asp Asn Ala Leu Ser Leu Lys Leu Pro
Phe Asp Asn Gln Gly Asn Leu Leu Asn Cys Ala Leu Glu Ser Ser Thr Trp
Arg Tyr Gln Glu Thr Asn Ala Val Ala Ser Asn Ala Leu Thr Phe Met Pro
Asn Ser Thr Val Tyr Pro Arg Asn Lys Thr Ala His Pro Gly Asn Met Leu
Ile Gln Ile Ser Pro Asn Ile Thr Phe Ser Val Val Tyr Asn Glu Ile Asn
Ser Gly Tyr Ala Phe Thr Phe Lys Trp Ser Ala Glu Pro Gly Lys Pro Phe
His Pro Pro Thr Ala Val Phe Cys Tyr Ile Thr Glu Gln

FIG. 3

```
        10         20         30         40         50         60
    *    *     *    *     *    *     *    *     *    *     *    *
GAATTCGCGC CACTCGAAAC CAAATTTTGC TGGAGCAAGC TGCCCTGACC TCCACCCCGC
CTTAAGCGCG GTGAGCTTTG GTTTAAAACG ACCTCGTTCG ACGGGACTGG AGGTGGGGCG

        70         80         90        100        110        120
    *    *     *    *     *    *     *    *     *    *     *    *
GAAGTCAATT GAACCCGCCC AATTGGCCCG CTGCCCAGGT GTATCAGGAA AACCCCGCTC
CTTCAGTTAA CTTGGGCGGG TTAACCGGGC GACGGGTCCA CATAGTCCTT TTGGGGCGAG

       130        140        150        160        170        180
    *    *     *    *     *    *     *    *     *    *     *    *
CGACCACAGT TCTCCTGCCA CGCGACGCTG AGGCCGAAGT CCAAATGACT AACTCCGGAG
GCTGGTGTCA AGAGGACGGT GCGCTGCGAC TCCGGCTTCA GGTTTACTGA TTGAGGCCTC

       190        200        210        220        230        240
    *    *     *    *     *    *     *    *     *    *     *    *
CGCAATTAGC GGGCGGATCC AGACACGTCA GGTTCAGAGG TCGGTCCTCG CCCTACTCTC
GCGTTAATCG CCCGCCTAGG TCTGTGCAGT CCAAGTCTCC AGCCAGGAGC GGGATGAGAG

       250        260        270        280        290        300
    *    *     *    *     *    *     *    *     *    *     *    *
CAGGTCCTAT AAAGAGGCTG ATTATCCGAG GCCGGGGTAT CCAGCTCAAC GACGAAGTGG
GTCCAGGATA TTTCTCCGAC TAATAGGCTC CGGCCCCATA GGTCGAGTTG CTGCTTCACC

       310        320        330        340        350        360
    *    *     *    *     *    *     *    *     *    *     *    *
TGAGCTCCTT AACCGGTCTC CGACCTGACG GAGTTTTCCA GCTTGGAGGT GCCGGCCGCT
ACTCGAGGAA TTGGCCAGAG GCTGGACTGC CTCAAAAGGT CGAACCTCCA CGGCCGGCGA

       370        380        390        400        410        420
    *    *     *    *     *    *     *    *     *    *     *    *
CCTCCTTCAC TCCTCGCCAG GCGTACCTGA CACTCCAGAG CTCTTCTTCC CAGCCTCGCT
GGAGGAAGTG AGGAGCGGTC CGCATGGACT GTGAGGTCTC GAGAAGAAGG GTCGGAGCGA

       430        440        450        460        470        480
    *    *     *    *     *    *     *    *     *    *     *    *
CCGGCGGCAT TGGAACCCTC CAGTTTGTGG AGGAGTTTGT ACCCTCCGTT TACTTCAACC
GGCCGCCGTA ACCTTGGGAG GTCAAACACC TCCTCAAACA TGGGAGGCAA ATGAAGTTGG
```

FIG.4A 4B 4B 4A 4A

```
       490        500        510        520        530        540
     *    *     *    *     *    *     *    *     *    *     *    *
CATTCTCGGG CGCTCCTGGT CTTTACCCAG ACGACTTCAT CCCAAACTAC GACGCGGTGA
GTAAGAGCCC GCGAGGACCA GAAATGGGTC TGCTGAAGTA GGGTTTGATG CTGCGCCACT

       550        560        570        580        590        600
     *    *     *    *     *    *     *    *     *    *     *    *
GCGAATCTGT GGACGGCTAC GACTGAATCC CAATGGTGCG TCCGTGACTG TGTGGCTGCA
CGCTTAGACA CCTGCCGATG CTGACTTAGG GTTACCACGC AGGCACTGAC ACACCGACGT

       610        620        630        640        650        660
     *    *     *    *     *    *     *    *     *    *     *    *
ACATCTACAT CGGCGCCGTA ATCCTTGCTA CTTTGTCTGA AAAGTCTGTG ATTTTTACTT
TGTAGATGTA GCCGCGGCAT TAGGAACGAT GAAACAGACT TTTCAGACAC TAAAAATGAA

       670        680        690        700        710        720
     *    *     *    *     *    *     *    *     *    *     *    *
ACCGCTCCAG CGCTTGGATT ACATGAAGAT CTGTGTTCTT TTTTGTGTGC TAAGTTTAAC
TGGCGAGGTC GCGAACCTAA TGTACTTCTA GACACAAGAA AAAACACACG ATTCAAATTG

       730        740        750        760        770        780
     *    *     *    *     *    *     *    *     *    *     *    *
AAGTAGCCTA AGGACTTCAC CTACAACCGT TGGTTCCTTA CGTCAGCTAC AAGATTCCAC
TTCATCGGAT TCCTGAAGTG GATGTTGGCA ACCAAGGAAT GCAGTCGATG TTCTAAGGTG

       790        800        810        820        830        840
     *    *     *    *     *    *     *    *     *    *     *    *
CAAAGGTACA CACCAAACTC TTTATTTTTC TGAGTCTACC ACTTCTATTG CACTTAACTG
GTTTCCATGT GTGGTTTGAG AAATAAAAAG ACTCAGATGG TGAAGATAAC GTGAATTGAC

       850        860        870        880        890        900
     *    *     *    *     *    *     *    *     *    *     *    *
TTCTTGTCGT AACCAACTCG TTCAGTGGCG CGCTAACAGA CAATTTTGCA AACTATTTTG
AAGAACAGCA TTGGTTGAGC AAGTCACCGC GCGATTGTCT GTTAAAACGT TTGATAAAAC

       910        920        930        940        950        960
     *    *     *    *     *    *     *    *     *    *     *    *
GGACGCTCTT ATTGTTCAAG GAAACAACAG CCTTTGTAAC AACTGTACTG CTACTACTTT
CCTGCGAGAA TAACAAGTTC CTTTGTTGTC GGAAACATTG TTGACATGAC GATGATGAAA

       970        980        990       1000       1010       1020
     *    *     *    *     *    *     *    *     *    *     *    *
AACTCTTACA CCTCCTTTTG TTCCCGGTCC ATACTTGTGC ATTGGCACAG GAAGAGGGCC
TTGAGAATGT GGAGGAAAAC AAGGGCCAGG TATGAACACG TAACCGTGTC CTTCTCCCGG
```

FIG.4B 4C 4C 4B 4B

```
      1030      1040      1050      1060      1070      1080
TAGCTGCTTT AATCGCTGGA CTTTACAAAA AGAGAACCTA ACCACTACCA CCCTCCTTCC
ATCGACGAAA TTAGCGACCT GAAATGTTTT TCTCTTGGAT TGGTGATGGT GGGAGGAAGG

      1090      1100      1110      1120      1130      1140
CCTTACTACT TATACTTTTT CCCAAAAAAA AATTTACTTT TTGCCCATTA TTGCACTTTT
GGAATGATGA ATATGAAAAA GGGTTTTTTT TTAAATGAAA AACGGGTAAT AACGTGAAAA

      1150      1160      1170      1180      1190      1200
GGCCTTTGTC TGTGTTATTA CCGCTAATTA CATTTTAATT TTCAATCTTG ATAATTTTTA
CCGGAAACAG ACACAATAAT GGCGATTAAT GTAAAATTAA AAGTTAGAAC TATTAAAAAT

      1210      1220      1230      1240      1250      1260
CTAATCATGC TGCTGTTTTT ACTTTGCCTT CTTTTCTGCT CTGCCTATGC CGCCGTGCCA
GATTAGTACG ACGACAAAAA TGAAACGGAA GAAAAGACGA GACGGATACG GCGGCACGGT

      1270      1280      1290      1300      1310      1320
GAAAAAACTC TTAACAACCT CGTTCGGGTG TATGCCTTAG TTGGTACCAA TCTATCCCTT
CTTTTTTGAG AATTGTTGGA GCAAGCCCAC ATACGGAATC AACCATGGTT AGATAGGGAA

      1330      1340      1350      1360      1370      1380
GATTCTATGA AAACTCCTCA GATTGACGAA CTTACTAGTC TTAGCTGGAT TAAACAGGAA
CTAAGATACT TTTGAGGAGT CTAACTGCTT GAATGATCAG AATCGACCTA ATTTGTCCTT

      1390      1400      1410      1420      1430      1440
GACAATCCTA ACAAAAACTT ACAATCATTT TTTTTTATTG GTCAAAAACT CTGTGAAGTT
CTGTTAGGAT TGTTTTTGAA TGTTAGTAAA AAAAAATAAC CAGTTTTTGA GACACTTCAA

      1450      1460      1470      1480      1490      1500
ACCAAAGACA AAATCACTGT TTTTAACTAT TATCCGTTGG AATTTTCCTG CGCTAACGTA
TGGTTTCTGT TTTAGTGACA AAAATTGATA ATAGGCAACC TTAAAAGGAC GCGATTGCAT

      1510      1520      1530      1540      1550      1560
ACCTTGTATT TGTATAATCT TAAAACTGAC GATTCTGGCC TCTATAATGG AAAGGCCCAT
TGGAACATAA ACATATTAGA ATTTTGACTG CTAAGACCGG AGATATTACC TTTCCGGGTA
```

FIG.4C 4D 4D 4C 4C

```
      1570       1580       1590       1600       1610       1620
    *    *     *    *     *    *     *    *     *    *     *    *
ACCAAAGAGC TTGAACATAA CACCTATGTT AGGCTTTATG TTATTGACAT TCCTCCGCCT
TGGTTTCTCG AACTTGTATT GTGGATACAA TCCGAAATAC AATAACTGTA AGGAGGCGGA

      1630       1640       1650       1660       1670       1680
    *    *     *    *     *    *     *    *     *    *     *    *
AAGTGTGACA TTACTTCACG TTACTTAGGC ATACAGGCTA CTGGGGAAGA TTATTGTTTA
TTCACACTGT AATGAAGTGC AATGAATCCG TATGTCCGAT GACCCCTTCT AATAACAAAT

      1690       1700       1710       1720       1730       1740
    *    *     *    *     *    *     *    *     *    *     *    *
ATTGAAATCA ATTGCACTAA CTCCAAATAC CCAGCTGTGG TTAAATTTAA TGGCAGGCAA
TAACTTTAGT TAACGTGATT GAGGTTTATG GGTCGACACC AATTTAAATT ACCGTCCGTT

      1750       1760       1770       1780       1790       1800
    *    *     *    *     *    *     *    *     *    *     *    *
AGCAACTTCT ACCATTATGT TAGCGAAAAC GGAAACAAAG AACTTCCAAA TTTTTATGAA
TCGTTGAAGA TGGTAATACA ATCGCTTTTG CCTTTGTTTC TTGAAGGTTT AAAAATACTT

      1810       1820       1830       1840       1850       1860
    *    *     *    *     *    *     *    *     *    *     *    *
ACACACATCA CTGTTAATGG TACCCACAAA AGCTTTCACT TTAATTACCC TTTTAACGAC
TGTGTGTAGT GACAATTACC ATGGGTGTTT TCGAAAGTGA AATTAATGGG AAAATTGCTG

      1870       1880       1890       1900       1910       1920
    *    *     *    *     *    *     *    *     *    *     *    *
CTTTGTCAAA CAACCAGCGC TCTACAATAT AATGACAATG TCCAGGTAGT CCTCATTCTT
GAAACAGTTT GTTGGTCGCG AGATGTTATA TTACTGTTAC AGGTCCATCA GGAGTAAGAA

      1930       1940       1950       1960       1970       1980
    *    *     *    *     *    *     *    *     *    *     *    *
CTCATAGTAG TTGGCTTAAT AATAATTTCC GCTAGTTTAA TATTGCTTTA TTGCCACCGC
GAGTATCATC AACCGAATTA TTATTAAAGG CGATCAAATT ATAACGAAAT AACGGTGGCG

      1990       2000       2010       2020       2030       2040
    *    *     *    *     *    *     *    *     *    *     *    *
AAAAAAATCA AGGCCGAAGT TCAACATCAA CCAGTGCATA TTTGTTTAGA AAAATAAAAT
TTTTTTTAGT TCCGGCTTCA AGTTGTAGTT GGTCACGTAT AAACAAATCT TTTTATTTTA

      2050       2060       2070       2080       2090       2100
    *    *     *    *     *    *     *    *     *    *     *    *
TTTTTTCTTT TCAGTATGGT AACTCCTCTT CTCCTGCTTG TCTGTCTGCC AATTATCTAC
AAAAAAGAAA AGTCATACCA TTGAGGAGAA GAGGACGAAC AGACAGACGG TTAATAGATG
```

FIG.4D 4E 4E 4D 4D

```
      2110       2120       2130       2140       2150       2160
    *    *     *    *     *    *     *    *     *    *     *    *
GCCTCCACCA CCTTCGCCGC AGTCTCCCAC CTTGATACGG ATTGTCTTCC CGCCTTGCTG
CGGAGGTGGT GGAAGCGGCG TCAGAGGGTG GAACTATGCC TAACAGAAGG GCGGAACGAC

      2170       2180       2190       2200       2210       2220
    *    *     *    *     *    *     *    *     *    *     *    *
ACTTATCTCA TCTTCACCTC TGTTTGCTGC ACTGCCATCT GCAGCATTGC CACTTTTTTT
TGAATAGAGT AGAAGTGGAG ACAAACGACG TGACGGTAGA CGTCGTAACG GTGAAAAAAA

      2230       2240       2250       2260       2270       2280
    *    *     *    *     *    *     *    *     *    *     *    *
GTGGCCATTT TCCAAACTGC GGACTACCTA TACGTTAGAG TGGCATACTA TCGTCATCAT
CACCGGTAAA AGGTTTGACG CCTGATGGAT ATGCAATCTC ACCGTATGAT AGCAGTAGTA

      2290       2300       2310       2320       2330       2340
    *    *     *    *     *    *     *    *     *    *     *    *
CCCCAATATA GGAACCACGA GGTGGCCGCC CTTCTGTGCC TGTCATGAAA GTTCCTCTTC
GGGGTTATAT CCTTGGTGCT CCACCGGCGG GAAGACACGG ACAGTACTTT CAAGGAGAAG

      2350       2360       2370       2380       2390       2400
    *    *     *    *     *    *     *    *     *    *     *    *
TCTGTCTTAT CCTCCTTCAC AAAGTCCTGG CCAACTGCCA CCTCCACCGG CCCACCGAGT
AGACAGAATA GGAGGAAGTG TTTCAGGACC GGTTGACGGT GGAGGTGGCC GGGTGGCTCA

      2410       2420       2430       2440       2450       2460
    *    *     *    *     *    *     *    *     *    *     *    *
TCCTGCGCTG CTACTCAACA GAAACCTCTT CCTTTTGGCT GTACTCCATT ATTTTTATTT
AGGACGCGAC GATGAGTTGT CTTTGGAGAA GGAAAACCGA CATGAGGTAA TAAAAATAAA

      2470       2480       2490       2500       2510       2520
    *    *     *    *     *    *     *    *     *    *     *    *
TGATTTTCTT TGCCACCTTT TTGGGATTAC AAATTTACGG CTGCCTTCAC CTGGGCTGGA
ACTAAAAGAA ACGGTGGAAA AACCCTAATG TTTAAATGCC GACGGAAGTG GACCCGACCT

      2530       2540       2550       2560       2570       2580
    *    *     *    *     *    *     *    *     *    *     *    *
TGCATCCTCC CAACAACCTA CCCAGATTTC CTGGTTTCTT ATTACAGCCC CCGCCGCCCC
ACGTAGGAGG GTTGTTGGAT GGGTCTAAAG GACCAAAGAA TAATGTCGGG GGCGGCGGGG

      2590       2600       2610       2620       2630       2640
    *    *     *    *     *    *     *    *     *    *     *    *
CACCAGCTCC TGTACAGCGC GCTCCATCAG TTATTAGCTA CTTTCATCTT AACTCTGAAG
GTGGTCGAGG ACATGTCGCG CGAGGTAGTC AATAATCGAT GAAAGTAGAA TTGAGACTTC
```

FIG.4E 4F 4F 4E 4E

```
      2650       2660       2670       2680       2690       2700
       *    *     *    *     *    *     *    *     *    *     *    *
ATGTCTGACC AACTAGAAAT CGACGGGCAG CGCACTGAGC AGCTGATCCT TGCTCGGCGA
TACAGACTGG TTGATCTTTA GCTGCCCGTC GCGTGACTCG TCGACTAGGA ACGAGCCGCT

      2710       2720       2730       2740       2750       2760
       *    *     *    *     *    *     *    *     *    *     *    *
AAACTCAAAC AACAAAACCA GGAATTGTTC AACCTTCAAG CCTTACACCA ATGCAAAAAG
TTTGAGTTTG TTGTTTTGGT CCTTAACAAG TTGGAAGTTC GGAATGTGGT TACGTTTTTC

      2770       2780       2790       2800       2810       2820
       *    *     *    *     *    *     *    *     *    *     *    *
GGTCTTTTCT GCCTGGTTAA ACAAGCTGAA CTTTGCTATG ATGTAACCCA ACAGGGGCAT
CCAGAAAAGA CGGACCAATT TGTTCGACTT GAAACGATAC TACATTGGGT TGTCCCCGTA

      2830       2840       2850       2860       2870       2880
       *    *     *    *     *    *     *    *     *    *     *    *
GAGCTATCAT ACACTTTAAA CAAGCAAAGA CAGAGCTTTA TGACTATGGT GGGGGTTAAG
CTCGATAGTA TGTGAAATTT GTTCGTTTCT GTCTCGAAAT ACTGATACCA CCCCCAATTC

      2890       2900       2910       2920       2930       2940
       *    *     *    *     *    *     *    *     *    *     *    *
CCCATTAAGG TTACTCAGCA ATCCGGCCCA GTTGAGGGAA GCATTCTTTG TCAGTGCACC
GGGTAATTCC AATGAGTCGT TAGGCCGGGT CAACTCCCTT CGTAAGAAAC AGTCACGTGG

      2950       2960       2970       2980       2990       3000
       *    *     *    *     *    *     *    *     *    *     *    *
AATTCTGAAT GCATGTACAC TATGGTAAAA ACCCTGTGTG GTCTCAGGGA ACTTCTCCCC
TTAAGACTTA CGTACATGTG ATACCATTTT TGGGACACAC CAGAGTCCCT TGAAGAGGGG

      3010       3020       3030       3040       3050       3060
       *    *     *    *     *    *     *    *     *    *     *    *
TTTAATTAAA GTTATCTGAT TAATAAAGCT TACCTTAAAT TTGATATCAG TTGTTTGTCA
AAATTAATTT CAATAGACTA ATTATTTCGA ATGGAATTTA AACTATAGTC AACAAACAGT

      3070       3080       3090       3100       3110       3120
       *    *     *    *     *    *     *    *     *    *     *    *
AGTTTTTCCA GCAGCACCAC CTGCCCTTCC TCCCAACTTT CGTAGGGGAT GTGCCAACGG
TCAAAAAGGT CGTCGTGGTG GACGGGAAGG AGGGTTGAAA GCATCCCCTA CACGGTTGCC

      3130       3140       3150       3160       3170       3180
       *    *     *    *     *    *     *    *     *    *     *    *
GCAGCAAACT TTCTCCACGT CCTAAAGGGT ATATCGGTGT TCACCTTTTT ACCCTGACCC
CGTCGTTTGA AAGAGGTGCA GGATTTCCCA TATAGCCACA AGTGGAAAAA TGGGACTGGG
```

FIG. 4F 4G 4G

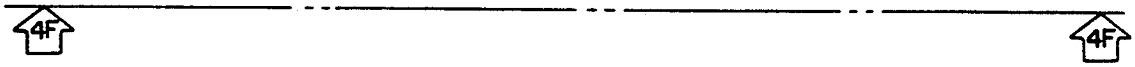

```
      3190       3200       3210       3220       3230       3240
     *    *     *    *     *    *     *    *     *    *     *    *
ACGATCTTCA TCTTGCAGAT GAAAAGAACC AGAATTGAAG ACGACTTCAA CCCCGTCTAC
TGCTAGAAGT AGAACGTCTA CTTTTCTTGG TCTTAACTTC TGCTGAAGTT GGGGCAGATG

      3250       3260       3270       3280       3290       3300
     *    *     *    *     *    *     *    *     *    *     *    *
CCCTATGACA CCTTCTCAAC TCCCAGCATC CCCTATGTAG CTCCGCCCTT CGTTTCTTCT
GGGATACTGT GGAAGAGTTG AGGGTCGTAG GGGATACATC GAGGCGGGAA GCAAAGAAGA

      3310       3320       3330       3340       3350       3360
     *    *     *    *     *    *     *    *     *    *     *    *
GACGGGTTAC AGGAAAAACC CCCAGGAGTT TTAGCACTCA AGTACACTGA CCCCATTACT
CTGCCCAATG TCCTTTTTGG GGGTCCTCAA AATCGTGAGT TCATGTGACT GGGGTAATGA

      3370
     *    *
ACCAATGCTA AGC
TGGTTACGAT TCG
```

FIG.4G

Met Lys Ile Cys Val Leu Phe Cys Val Leu Ser Leu Thr Ser Ser Leu Arg
Thr Ser Pro Thr Thr Val Gly Ser Leu Arg Gln Leu Gln Asp Ser Thr Lys
Gly Thr His Gln Thr Leu Tyr Phe Ser Glu Ser Thr Thr Ser Ile Ala Leu
Asn Cys Ser Cys Arg Asn Gln Leu Val Gln Trp Arg Ala Asn Arg Gln Phe
Cys Lys Leu Phe Trp Asp Ala Leu Ile Val Gln Gly Asn Asn Ser Leu Cys
Asn Asn Cys Thr Ala Thr Thr Leu Thr Leu Thr Pro Pro Phe Val Pro Gly
Pro Tyr Leu Cys Ile Gly Thr Gly Arg Gly Pro Ser Cys Phe Asn Arg Trp
Thr Leu Gln Lys Glu Asn Leu Thr Thr Thr Thr Leu Leu Pro Leu Thr Thr
Tyr Thr Phe Ser Gln Lys Lys Ile Tyr Phe Leu Pro Ile Ile Ala Leu Leu
Ala Phe Val Cys Val Ile Thr Ala Asn Tyr Ile Leu Ile Phe Asn Leu Asp
Asn Phe Tyr

FIG.5

```
Met Leu Leu Phe Leu Leu Cys Leu Leu Phe Cys Ser Ala Tyr Ala Ala Val
Pro Glu Lys Thr Leu Asn Asn Leu Val Arg Val Tyr Ala Leu Val Gly Thr
Asn Leu Ser Leu Asp Ser Met Lys Thr Pro Gln Ile Asp Glu Leu Thr Ser
Leu Ser Trp Ile Lys Gln Glu Asp Asn Pro Asn Lys Asn Leu Gln Ser Phe
Phe Phe Ile Gly Gln Lys Leu Cys Glu Val Thr Lys Asp Lys Ile Thr Val
Phe Asn Tyr Tyr Pro Leu Glu Phe Ser Cys Ala Asn Val Thr Leu Tyr Leu
Tyr Asn Leu Lys Thr Asp Asp Ser Gly Leu Tyr Asn Gly Lys Ala His Thr
Lys Glu Leu Glu His Asn Thr Tyr Val Arg Leu Tyr Val Ile Asp Ile Pro
Pro Pro Lys Cys Asp Ile Thr Ser Arg Tyr Leu Gly Ile Gln Ala Thr Gly
Glu Asp Tyr Cys Leu Ile Glu Ile Asn Cys Thr Asn Ser Lys Tyr Pro Ala
Val Val Lys Phe Asn Gly Arg Gln Ser Asn Phe Tyr His Tyr Val Ser Glu
Asn Gly Asn Lys Glu Leu Pro Asn Phe Tyr Glu Thr His Ile Thr Val Asn
Gly Thr His Lys Ser Phe His Phe Asn Tyr Pro Phe Asn Asp Leu Cys Gln
Thr Thr Ser Ala Leu Gln Tyr Asn Asp Asn Val Gln Val Val Leu Ile Leu
Leu Ile Val Val Gly Leu Ile Ile Ile Ser Ala Ser Leu Ile Leu Leu Tyr
Cys His Arg Lys Lys Ile Lys Ala Glu Val Gln His Gln Pro Val His Ile
Cys Leu Glu Lys
```

FIG.6

Met Ala Gly Lys Ala Thr Ser Thr Ile Met Leu Ala Lys Thr Glu Thr Lys
Asn Phe Gln Ile Phe Met Lys His Thr Ser Leu Leu Met Val Pro Thr Lys
Ala Phe Thr Leu Ile Thr Leu Leu Thr Thr Phe Val Lys Gln Pro Ala Leu
Tyr Asn Ile Met Thr Met Ser Arg

FIG.7

Met Val Thr Pro Leu Leu Leu Leu Val Cys Leu Pro Ile Ile Tyr Ala Ser
Thr Thr Phe Ala Ala Val Ser His Leu Asp Thr Asp Cys Leu Pro Ala Leu
Leu Thr Tyr Leu Ile Phe Thr Ser Val Cys Cys Thr Ala Ile Cys Ser Ile
Ala Thr Phe Phe Val Ala Ile Phe Gln Thr Ala Asp Tyr Leu Tyr Val Arg
Val Ala Tyr Tyr Arg His His Pro Gln Tyr Arg Asn His Glu Val Ala Ala
Leu Leu Cys Leu Ser

FIG.8

Met Lys Val Pro Leu Leu Cys Leu Ile Leu Leu His Lys Val Leu Ala Asn
Cys His Leu His Arg Pro Thr Glu Phe Leu Arg Cys Tyr Ser Thr Glu Thr
Ser Ser Phe Trp Leu Tyr Ser Ile Ile Phe Ile Leu Ile Phe Phe Ala Thr
Phe Leu Gly Leu Gln Ile Tyr Gly Cys Leu His Leu Gly Trp Met His Pro
Pro Asn Asn Leu Pro Arg Phe Pro Gly Phe Leu Leu Gln Pro Pro Pro Pro
Pro Pro Ala Pro Val Gln Arg Ala Pro Ser Val Ile Ser Tyr Phe His Leu
Asn Ser Glu Asp Val

FIG.9

Met Ser Asp Gln Leu Glu Ile Asp Gly Gln Arg Thr Glu Gln Leu Ile Leu
Ala Arg Arg Lys Leu Lys Gln Gln Asn Gln Glu Leu Phe Asn Leu Gln Ala
Leu His Gln Cys Lys Lys Gly Leu Phe Cys Leu Val Lys Gln Ala Glu Leu
Cys Tyr Asp Val Thr Gln Gln Gly His Glu Leu Ser Tyr Thr Leu Asn Lys
Gln Arg Gln Ser Phe Met Thr Met Val Gly Val Lys Pro Ile Lys Val Thr
Gln Gln Ser Gly Pro Val Glu Gly Ser Ile Leu Cys Gln Cys Thr Asn Ser
Glu Cys Met Tyr Thr Met Val Lys Thr Leu Cys Gly Leu Arg Glu Leu Leu
Pro Phe Asn

FIG. 10

PROTEIN CODING REGIONS IN THE E3-FIBER AREA OF THE HUMAN ENTERIC ADENOVIRUS TYPE 41 TAK (MAP POSITION OF FRAGMENT SHOWN: 74% TO 92%)

DETECTION OF HUMAN ADENOVIRUS

CROSS-REFERENCE TO PRIOR APPLICATION

The present application is a continuation-in-part of U.S. Pat. Ser. No. 442,027 filed Nov. 27, 1989, now abandoned.

FIELD OF INVENTION

The present invention relates to DNA and proteins of human adenovirus type 41 and methods of detection thereof. In particular, the present invention relates to the isolation of a 41.4 kd fiber protein ("short" fiber protein) and a 60.6 kd fiber protein ("long" fiber protein) of human adenovirus type 41 (Ad41), as well as proteins derived from the Ad41 E3 region, thereby providing virus-derived antigens and active derivatives and parts thereof, useful in the development of diagnostic assays, DNA probes and vaccines for said virus or other related viruses belonging to the human enteric adenovirus family. The present invention is further directed to recombinant DNA molecules containing the Ad41 long fiber protein gene, the Ad41 short fiber protein gene and the Ad41 E3 gene (encoding the proteins RL-1 to RL-6) thereby providing a source of recombinant viral components useful in the development of said diagnostic assays for Ad41. The present invention is also directed to first antibodies specific to the above-identified Ad41 viral components and to second antibodies specific to the first antibodies. These second antibodies are also useful in the development of diagnostic assays for Ad41 and other adenoviruses.

BACKGROUND OF THE INVENTION

Adenoviruses are simple DNA-containing viruses (i.e., composed of only DNA and protein) that multiply in the cell nucleus of the host. These viruses induce latent or acute infections in tonsils, adenoids, lungs, bladder and cornea as well as the gastrointestinal tract and are readily activated. Several adenoviruses are the first common viruses of humans shown to be oncogenic for lower animals under special experimental circumstances. The adenoviruses may serve as "helpers" for adeno-associated viruses which cannot replicate in their absence.

The viral particles of the adenovirus have a dense central core and an outer coat known as the capsid. These particles have an icosahedral configuration and are composed of 252 capsomers: 240 hexons make up the faces and edges of the equilateral triangles and 12 pentons comprise the vertices. The hexons are truncated triangular or polygonal prisms with a central hole. The pentons are more complex, consisting of a polygonal base with an attached fiber protein, whose length (i.e., short or long) varies with viral type. Minor capsid proteins are also associated with the hexons or pentons and confer stability on the capsid to form links with the core proteins, and to function in virion assembly.

Each virion contains one linear, double-stranded DNA molecule associated with proteins to form the core of the adenovirus.

The early region 3 (E3) of adenoviruses plays a critical role in pathogenesis of the virus's disease process even though none of its gene products are essential for replication of the virus in cell cultures. Not all proteins coded in the E3 regions of adenoviruses have been identified, even for the most commonly studied adenovirus, type 2 (Ad2). However, it has been postulated that they mediate cellular or immunological responses through structural or functional homology to regulatory molecules. For this reason, it is possible that proteins generated from the E3 region, or their derivatives, can be used in therapy as modulators of the immune response (e.g., as an immunostimulation system in AIDS patients) or as anti-cancer agents to modify the action of various growth factors. In addition, specific E3 proteins can be used to distinguish between different adenovirus types.

Adenoviruses are widespread in nature. The 89 accepted members of the adenovirus family have similar chemical and physical characteristics and a family cross-reactive antigen but are distinguished by antibodies to their individual type-specific antigens: at least 41 are from humans and the rest from various animals.

The enteric adenoviruses, such as Adenovirus Type 40 or 41 (and also known as Type F Enteric Adenoviruses), are a virus group that cause serious intestinal and diarrheal diseases of young children. In 1978, the World Health Organization initiated a program for global prevention and control for such childhood diseases. As a result, the relative importance of various pathogens in the etiology of diarrhea in many parts of the world has been recognized. For example, rotaviruses, which rank as the most prevalent viral pathogen in childhood diarrhea, may now be close to control as many vaccines are now in sight. This has been made possible through very intensive research over the past decade.

However, the control of enteric adenoviruses, which are responsible for at least 15% of all cases of severe infantile gastroenteritis, is not yet within reach. Although they are second after rotaviruses as viral agents causing this type of infection, enteric adenoviruses remain a poorly defined group of viruses. The paucity of research done on enteric adenoviruses is mainly due to the difficulty of propagating the viruses in cultures. For this reason, there is no sensitive, fast, and diagnostic procedure able to distinguish between enteric adenoviruses and other adenoviruses (Group A, B, C, D, and E) which are commonly present in stools but are not agents of gastroenteritis. Another reason for studying enteric adenoviruses is their possible link to intestinal cancer which appears later in the life of infected individuals.

The standard reference methods for diagnosis of enteric adenoviruses have been (1) immunoelectron microscopy; (2) type-specific neutralization; (3) growth differences on primary human and Graham-293 cells. None of these methods are accurate and suitable for rapid routine use. Recently a new commercially available enzyme-linked immunoabsorbent assay (ELISA) to detect enteric adenoviruses (Adeno-Type 40/41 EIA, Cambridge Bioscience) based on a polyclonal antibody to enteric adenovirus hexon protein was created, but this kit lacks both specificity and sensitivity.

However, the present invention solves the problems associated with the previous methodologies. The present invention describes a recombinant DNA molecule which can produce at least one of Human Adenovirus Type 41 Tak (Ad41) short fiber protein, long fiber protein, or proteins RL-1 to RL-6 of the Ad41 E3 region. (There are presently several isolates known of human adenovirus type 41, but the most common isolate of this adenovirus is human adenovirus type 41 Tak, represented in the present invention. This isolate is the standard Ad41 strain and it is listed in the American Type Culture collection under catalog number ATCC #VR-930.)

The Ad41 short and long fiber protein gene and Ad41 E3 proteins are useful for assays for human enteric adenoviruses since they express only minor immunological cross-reactivity between adenoviruses belonging to different serotypes; they are unique adenovirus proteins (i.e., Ad41 long fiber protein and possibly the short fiber as well are responsible for attachment of the virus to specific cellular receptors in the cell membrane during infection) and they express selective type-specific antigenicity. The genes of the present invention are ideal candidates for specific, selective monoclonal antibodies based on an enzyme immunoassay (EIA) kit, a DNA probe assay system and a vaccine derived from the gene products. The present invention will not only enhance the understanding of the mechanism by which human enteric adenoviruses cause disease in humans, but will also assist in developing molecular probes for diagnosis of such infections.

SUMMARY OF THE INVENTION

The present invention relates to human adenovirus type 41 Tak long fiber protein gene and the encoded Ad41 long fiber protein.

Another aspect of this invention is directed to human adenovirus type 41 Tak short fiber protein gene and the encoded Ad41 short fiber protein.

Yet another aspect of this invention is directed to the human adenovirus type 41 Tak E3 region gene and 6 proteins, RL1-RL6, identified by their encoding DNA sequence in the E3 gene and their encoding amino acid sequence.

A further aspect of this invention is directed to using at least one of the above-identified proteins in methods of detection of adenoviruses, and in particular, human enteric adenoviruses.

Still another aspect of this invention is the production of polyclonal or monoclonal antibodies to at least one of the above-identified proteins.

Yet another aspect of the present invention is the use of said antibodies in the detection and diagnosis of human adenovirus type 41 and antigenically related viruses such as Ad40.

Another aspect of this invention is directed to recombinant DNA molecules containing at least one of the above-identified genes thereby providing a source of recombinant viral components useful in the development of diagnostic assays for adenoviruses.

A further aspect of this invention is directed to the use of the recombinant viral components of at least one of the above-identified genes or derivatives or parts thereof in the development of diagnostic assays for Ad41 and antigenically related viruses, such as Ad40.

Still another aspect of this invention is the use of said recombinant viral components or derivatives or parts thereof, to generate antibodies useful in diagnostic and therapeutic techniques for human adenoviruses.

Still another aspect of this invention relates to probe nucleic acids for hybridization to homologous Ad41 DNA sequences utilizing the sequence of at least one of the above-identified Ad41 genes.

A further aspect of this invention is the use of at least one of said recombinant viral components to produce a vaccine to Ad41, or other antigenically related viruses such as Ad40.

Yet another aspect of the present invention relates to a kit for diagnosis and monitoring of human adenovirus antibody generated by Ad41 long fiber protein and/or Ad41 short fiber protein and/or Ad41 E3 proteins.

A further aspect of this invention relates to a method of treating infectious diseases caused by Ad41 and other related adenoviruses such as Ad40.

Another aspect of this invention relates to a method of inactivating human adenovirus type 41 and structurally related adenoviruses.

Yet another aspect of the present invention relates to a kit for production of recombinant viral components of at least one of the above-identified Ad41 genes to produce a vaccine to Ad41 or related viruses such as Ad40.

Still another aspect of this invention relates to a method for detection and diagnosis of human enteric adenoviruses, and in particular, human Ad41, by probe nucleic acids utilizing the sequence of at least one of the above-identified genes.

A further aspect of this invention relates to a pharmaceutical composition containing at least one of the above-identified Ad41 proteins or derivatives thereof, for treatment of Ad41 or related viruses such as Ad40.

These and other aspects of the present invention can be achieved by utilization of the previously undiscovered Ad41 DNA and proteins of the present invention.

BRIEF DESCRIPTION OF THE FIGURES

FIG. 1A-1F are a representation of the DNA sequence of the human enteric adenovirus Type 41 Tak long fiber protein gene, and the corresponding amino acid sequence of Ad41 long fiber protein FIGS. 1A-1F are hereinafter referred to as FIG. 1.

FIGS. 2A-2C are a representation of the DNA sequence of the human enteric adenovirus Type 41 Tak short fiber protein gene FIGS. 2A-2C are hereinafter referred to as FIG. 2.

FIG. 3 is a representation of the amino acid sequence of Ad41 short fiber protein.

FIGS. 4A-4G are a representation of the DNA sequence of the human enteric adenovirus Type 41 Tak E3 gene FIGS. 4A-4G are hereinafter referred to as FIG. 4.

FIG. 5 is a representation of the amino acid sequence of Ad41 RL-1, protein.

FIG. 6 is a representation of the amino acid sequence of Ad41 RL-2 protein.

FIG. 7 is a representation of the amino acid sequence of Ad41 RL-3 protein.

FIG. 8 is a representation of the amino acid sequence of Ad41 RL-4 protein.

FIG. 9 is a representation of the amino acid sequence of Ad41 RL-5 protein.

FIG. 10 is a representation of the amino acid sequence of Ad41 RL-6 protein.

DETAILED DESCRIPTION OF THE INVENTION

Figure 11:
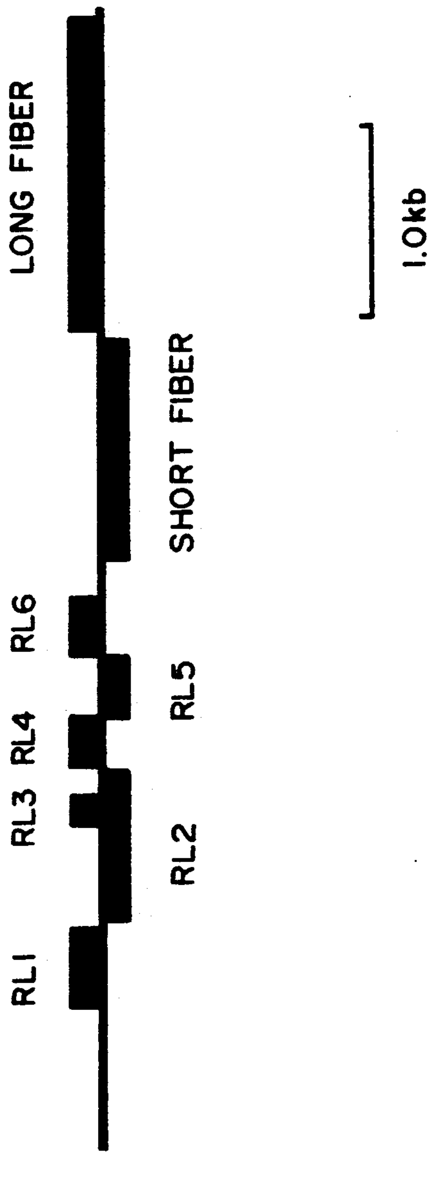
FIG. 11 is a representation of a map of the protein coding regions in the E3 region and fiber (short and long) area of the human enteric adenovirus type 41 Tak. The E3 region is represented by proteins RL-1 to RL-6. The map position of the fragment shown is 74% to 92%.

The present invention contemplates identification, isolation and utilization of structural components of Type F Adenoviruses. In particular, the present invention relates to the human adenovirus Type 41 Tak (Ad41) long fiber protein gene, short fiber protein gene, and the entire E3 gene, and diagnostic assays, monoclonal and polyclonal antibodies, DNA probes, and vaccines prepared relative thereto. This invention provides the advantage of a previously unavailable source of virus particles and parts thereof, and antigenic determinants and parts thereof, being highly desirable for its medical and experimental utility.

In accordance with the present invention, the Ad41 long fiber protein gene, the Ad41 short fiber protein gene and the Ad41 E3 gene have been obtained by DNA sequencing of selected clones from an Ad41 library using standard techniques.

With respect to the Ad41 fiber protein gene coding for a 60.6 kd Ad41 fiber protein, henceforth this will be referred to in the Specification and Claims, as "Ad41 long fiber protein" and "Ad41 long fiber protein gene". In particular, this Ad41 long fiber protein gene found in the 1.9 Kb SmaI-EcoRI DNA fragment (map position 86.4% to 92%) of the human enteric Ad41 strain Tak was cloned in pBluescript II and sequenced directly using custom oligonucleotide primers. The gene coding for the Ad41 long fiber protein was identified using the sequence of Ad5 fiber protein gene as a reference. The procedure is outlined in more detail in the Examples.

In general, the fiber protein gene has three structural domains, the tail, the shaft and the knob, (i.e., $NH_2$ [N-terminus]—tail, shaft, knob—COOH [C-terminus]). Of these three domains, the "knob", which is responsible for the interaction of the virus with the cellular receptors displayed the lowest homology with other human adenoviruses such as Ad2, Ad3, Ad5, and Ad7 at the DNA or protein level.

A 650 bp Hind III/Eco RI DNA fragment coding for the "knob" domain is subcloned on pUC18 vector and used in standard Southern hybridization with DNAs of representative serotypes of the Adenovirus subgroups, A, B, C, D, E, and F. Only human enteric adenoviruses Ad40 and Ad41 of Type F can be detected.

The dsDNA sequence of the Ad41 long fiber protein gene and subsequent amino acid sequence of Ad41 long fiber protein is represented in FIG. 1. Ad41 long fiber protein shows a high degree of homology with Ad40 fiber protein, except for the shaft region. The Ad41 long fiber protein gene shaft contains 22 typical amino acid repeats, whereas Ad40 has only 21 such repeats. (This refers to the fact that all fiber protein genes sequenced to date have shown a characteristic 15-residue motif, which is repeated 6 to 12 times and detection of this motif has aided rapid recognition of the sequence.) There is 97.7% homology between the amino acid sequence of Ad41 long fiber protein and Ad40 fiber protein in the knob region.

Further analysis has shown that the long fiber protein gene as represented in FIG. 1, starting from the N-terminus (from the left in FIG. 1 or from the 5' end of the DNA) is composed of the domains discussed above and set forth in further detail below.

(i) "Tail". It is 126 bases long (from base at position 201 to 326). On the protein level, it has 42 amino acid residues (from Met [Methionine] to Pro [Proline]). The "tail" anchors the fiber in the penton base on the virion surface and show a high degree of homology between all adenoviruses.

(ii) "Shaft". It is 1038 bases long (from base at position 327 to 1364). On the protein level it has 346 amino acid residues (from Gly [Glycine] to Leu [Leucine]). The "shaft" is a structural part of the fiber and is composed of repeating units (about 15 amino acids in each unit) showing high structural (but not sequence) homology among all adenoviruses. The number of these repeating units determines the length of fiber protein. In the case of Ad5, Ad2 and Ad41, there are 22 such units; in the case of Ad3 and Ad7, 6 units; and in Ad40, 21 units.

(iii) "Knob". It is 525 bases long (from base at position 1365 to 1889). On the protein level, it has amino acid residues (from Trp [Tryptophan] to Gln [Glutamic acid]). The TAA sequence ending the DNA sequence of the fiber gene (bases 1887–1889) is a part of the gene, but is not translated into an amino acid; it is a termination (or nonsense) codon. The "knob" region is responsible for the interaction of the virus with cellular receptors and determines the specificity of the virus. It differs substantially from adenovirus to adenovirus, depending on the types of cells infected by the virus.

The sequences flanking the Ad41 long fiber protein gene found in FIG. 1 contain various regulatory signals.

With respect to the previously undiscovered 41.4 kd Ad41 protein gene and subsequent protein encoded therein, these are henceforth characterized in the Specification and Claims as "Ad41 short fiber protein gene" and "Ad41 short fiber protein".

It was surprisingly found when sequencing the DNA of the human enteric adenovirus type 41 Tak genome upstream of the Ad41 long fiber protein gene, using standard techniques, that an open reading frame of 387 amino acids existed coding for the heretofore undisclosed Ad41 short fiber protein. The first 42 amino acids of the Ad41 short fiber protein show a high degree of homology both to Ad41 (74%) and Ad2 (61%) 60.6 kd long fiber protein tail domains. Furthermore, amino acids 43 to 233 of the short fiber protein form a typical shaft domain of twelve 15-residue repetitive motifs which is in contrast to 22 such repeats found for Ad2, Ad5, and the long fiber protein of Ad41 or 6 repeats found for Ad3 and Ad7. The knob domain (amino acids 234 to 387) is about 15% shorter than found for the above mentioned viruses. If this gene is expressed, Ad41 would resemble avian adenoviruses which were found to have two fibers of different length protruding from their pentons. The sequence presented in FIG. 2 is from the EcoRV site at map position 83.1% to the AccI site at map position 87.1%. This region was cloned and sequenced in a manner similar to that described above.

The structure of the short fiber shows the same structural elements as described for other fiber genes (but not the identical sequence), namely:

(i) "Tail". It is 126 bases long (from base at position 157 to 282). On the protein level, it has 42 amino acid residues (from Met [Methionine] to Pro [Proline]).

(ii) "Shaft". It is 573 bases long (from base at position 283 to 855). On the protein level it has 191 amino acid residues (from Gly [Glycine] to Ile [Isoleucine]). The short fiber of Ad41 has 12 repeating units.

(iii) "Knob". The short fiber "knob" of Ad41 is 465 bases long (from base at position 856 to base at position 1320). On the protein level, it has 154 amino acids (from Trp [Tryptophane] to Gln [Glutamine]). The TAA sequence ending the short fiber protein gene (bases 1318–1320) is a part of the gene, but is not translated into an amino acid; it is a termination codon.

The knob region of the Ad41 short fiber protein is very different from the knob region of the long fiber protein as well as from knob regions of fiber proteins of other adenoviruses.

This enteric adenovirus (Ad41) is understood to use two different receptors on the surface of a cell for binding and/or penetration. It is also understood that two different fibers with distinct "knobs" permit the Ad41 virus to infect at least two different types of cells in the gastrointestinal tract. Therefore the present invention also relates to diagnostic immunoassays and effective vaccines which utilize the different Ad41 fiber proteins as discussed in further detail below.

In addition, the present invention also contemplates another critical sequence, the DNA sequence of the Ad41 E3 region as shown in FIG. 3. This will be referred to in the Specification and Claims as the Ad41 E3 gene. In addition, the amino acid sequences of six putative proteins encoded by this region are described herein, and referred to in the Specification and Claims as RL-1, RL-2, RL-3, RL-4, RL-5 and RL-6 as set forth in further detail below.

The Ad41 E3 region DNA sequence has 3373 bases, including the flanking regions. The sequence disclosed herein is from the EcoRI restriction site at map position 74% to the EspI restriction site at map position 83.9%.

The Ad41 E3 region codes for some unique, previously unrevealed proteins. The Ad41 E3 region contains information sufficient to code for at least 6 proteins; in the following order (from the left, or 5' end):

(1) The region from base 683 to base 1204 codes for a 19.4 kd protein, referred to herein as RL-1. This protein has 173 amino acid residues. It is unique for Ad41.

(2) The region from base 1207 to 2037 codes for a 31.6 kd protein, referred to herein as RL-2. This protein has 276 amino acid residues. It is unique for Ad41.

(3) The region from base 1730 to 1909 codes for a 6.7 kd protein (in a different reading frame than the 31.6 kd protein), referred to herein as RL-3. This protein has 59 amino acid residues and is unique for Ad41.

(4) The region from base 2056 to base 2328 codes for a 10.1 kd protein, referred to herein as RL-4. This protein has 90 amino acid residues and shows 40% homology to an Ad2 10.4 kd protein. It was postulated by Carlin, et al., *Cell*, 57:135-144 (1989) that the same protein in Ad2 induces internalization and degradation of the epidermal growth factor receptors (EGF-R).

(5) The region from base 2325 to base 2648 codes for a 12.3 kd protein, referred to herein as RL-5. This protein has 107 amino acid residues and shows 35% homology to an Ad2 14.5 kd protein; the function of the Ad2 protein is unknown.

(6) Finally, the region from base 2641 to base 3009 codes for a 14.0 kd protein, referred to herein as RL-6. This protein has 122 amino acid residues and shows 50% homology to an Ad2 14.7 kd protein which was found by Gooding, et al., *Cell*, 53:341-346 (1988) to inhibit cytolysis by the tumor necrosis factor (TNF).

The present invention contemplates the use of the Ad41 long and short fiber protein genes, and the Ad41 E3 region gene, via production of their gene products, to prepare antibodies. Such antibodies may be monoclonal or polyclonal. Additionally, it is within the scope of this invention to include second antibodies (monoclonal or polyclonal) directed to the first antibodies discussed above.

Accordingly, the present invention relates to a method for stimulating an immune response to human adenovirus type 41 Tak which consists of administering an effective amount of at least one of Ad41 long fiber protein, Ad41 short fiber protein, and Ad41 E3 proteins RL-1, RL-2, RL-3, RL-4, RL-5 and RL-6, under conditions as described below, sufficient to cause the production of polyclonal or monoclonal antibodies to at least one of said Ad41 proteins, wherein the dosage effective amount of said Ad41 proteins can be from about 0.001 mg to 100 mg.

In order to produce such antibodies, Ad41 long fiber protein, Ad41 short fiber protein or Ad41 E3 proteins (RL-1 to RL-6) are first purified, and methods of antibody production are described below. Both polyclonal and monoclonal antibodies are obtainable by immunization with at least one of the above-identified proteins or their active components (which, in the case of the fiber proteins, can be the tail, shaft or knob). The methods of obtaining both types of antibodies are well known in the art; e.g., extensive protocols for antibody production can be found in Harlow, et al., *Antibodies: A Laboratory Manual*, Cold Spring Harbor, N.Y., 1988. Polyclonal antibodies are less preferred, but are relatively easily prepared by injection of a suitable laboratory animal with, for example, 0.001 to 100 mg of the purified viral antigenic component, collecting serum from the animal, and isolating specific sera by any of the known immunoadsorbent techniques. Although antibodies produced by this method are utilizable in virtually any type of immunoassay, they are generally less favored because of the potential heterogeneity of the product.

In another embodiment of the present invention, monoclonal antibodies are contemplated for detection and diagnosis of Ad41 and related adenoviruses.

The production of monoclonal antibodies relative to the present invention is particularly preferred because of the ability to produce monoclonal antibodies in large quantities and the homogeneity of the final product. The preparation of hybridoma cell lines for monoclonal antibody production derived by fusing an immortal cell line and lymphocytes sensitized against the immunogenic preparation can be done by techniques which are well known to those who are skilled in the art. (See, e.g., Kohler, G. and Milstein, C., Nature 256: 495-497, 1975; *European Journal of Immunology*, 6:511-519, 1976; the teachings of which are herein incorporated by reference).

Unlike preparation of polyclonal sera, the choice of animal is dependent on the availability of appropriate immortal lines capable of fusing with lymphocytes thereof. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with, for example, a preferred range from about 1 mg to about 20 mg of the purified virus or antigenic component thereof. (A range of 0.001 mg to 100 mg of purified viral component is also contemplated.) Usually the injecting material is emulsified in Freund's complete adjuvant. Boosting injections may also be required. The detection of antibody production can be carried out by testing the antisera with appropriately labeled antigen. Lymphocytes can be obtained by removing the spleen or lymph nodes of sensitized animals in a sterile fashion and carrying out fusion. Alternately, lymphocytes can be stimulated or immunized in vitro, as described, for example, in C.Reading, *J. Immunol. Meth.* 53: 261-291, 1982.

A number of cell lines suitable for cell fusion have been developed, and the choice of any particular cell line for hybridization protocols in the production of monoclonal antibodies is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglubulin. Included among these are the following mouse myeloma lines: $MPC_{11}$-X45-6TG, P3-NS1-1-Ag4-1, P3-X63-Ag8, or mutants thereof such as X63-Ag8.653, SP2-0-Ag14 (all BALB/C derived), Y3-'Ag1.2.3 (rat), and U266 (human).

Cell fusion can be induced either by virus, such as Epstein-Barr on Sendai virus, or polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1,000 to about 70% w/w in saline or serum-free medium. Exposure to PEG at 37° C. for about 30 seconds is preferred in the present case, utilizing murine cells. Extremes of temperature (i.e. about 45° C.) are avoided, and preincubation of each component of the fusion system at 37° C. prior to fusion gives optimum results. The ratio between lymphocytes and malignant cells range of from about 1:1 to about 1:10 gives good results.

The successfully fused cells can be separated from the myeloma line by any technique known by the art. The most common and preferred method is to choose a malignant line which is Hypoxanthine Guanine Phosphoribosyl Transferase (HGPRT) deficient, which will not grow in an aminopterin-containing medium used to allow only growth of hybrids and which is generally composed of hypoxanthine $1\times10^{-4}$M, aminopterin $1\times10^{5}$M, and thymidine $3\times10^{-5}$M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxanthine, thymidine-containing medium.

The growing colonies described above are tested for the presence of monoclonal antibodies that recognize the antigenic preparation, wherein said antigenic preparation which includes at least one of the above-identified Ad41 proteins or a derivative thereof. Hybridoma antibodies are identified by using an assay where the antigen is bound to a solid support and allowed to react to hybridoma supernatants containing putative antibodies. The presence of antibodies is shown by "sandwich" techniques using a variety of indicators, as discussed in further detail below. Most of the common methods are sufficiently sensitive for use in the range of antibody concentrations secreted during hybrid growth.

Cloning of antibody-secreting hybrids can be carried out after 21–23 days of cell growth in selected medium. Cloning can be performed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semisolid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

The present invention further contemplates the use of the above-described antibodies in a detection assay (immunoassay) for human enteric adenoviruses (Group F), particularly Ad41 and Ad40.

A wide range of immunoassay techniques are available as can be seen by reference to U.S. Pat. Nos. 4,016,043, 4,424,279, 4,018,653 and by Harlow, et al., supra. This, of course, includes both single-site and two-site, or "sandwich", assays of the non-competitive types, as well as in traditional competitive binding assays. Sandwich assays are among the most useful and commonly used assays and are favored for use in the present invention. A number of variations of the sandwich assay technique exist, and all are intended to be encompassed by the present invention.

In a typical forward assay, an unlabeled antibody is immobilized in a solid substrate and the sample to be tested brought into contact with the bound molecule. After a suitable period of incubation, for a period of time sufficient to allow formation of an antibody-antigen binary complex, a second antibody, labeled with a reporter molecule capable of producing a detectable signal is then added and incubated, allowing time sufficient for the formation of a ternary complex of antibody-labeled antibody. Any unreacted material is washed away, and the presence of the antigen is determined by observation of the visible signal produced by the reporter molecule. The results may either be qualitative, by simple observation of the visible signal, or may be quantitated by comparing with a control sample containing known amounts of hapten.

Variations on the forward assay include a simultaneous assay, in which both sample and labeled antibody are added simultaneously to the bound antibody, or a reverse assay in which the labeled antibody and sample to be tested are first combined, incubated and then added to the unlabeled surface bound antibody. These techniques are well known to those skilled in the art, and the possibility of minor variations will be readily apparent to those skilled in the art.

As used herein, "sandwich assay" is intended to encompass all variations on the basic two-site technique. For example, these antibodies may be used to detect Ad41 by its long and/or short fiber proteins or any one of E3 proteins RL-1 to RL-6 or other antigenically related adenoviruses (i.e., Ad40) by use of specific antigenic determinants, or parts thereof (i.e., Ad41 fiber proteins, or the tails, shafts or knobs of said proteins) as immobilized immunoadsorbants. Serum is obtained from subjects to be tested and said serum contacted to the immobilized viral immunoadsorbants. If said serum contains antibodies to said immunoadsorbants, an antibody-adsorbant conjugate will result. After removing excess serum and non-bound antibodies, a second antibody specific to a first antibody, said first antibody being capable of forming a conjugate with said immunoadsorbant, is added thus resulting in a double antibody-adsorbant conjugate. This double antibody-adsorbant conjugate will only result if the test serum contains antibodies to the immunoadsorbant. Consequently, standard detection techniques can be used to identify the conjugate.

In another immunoassay, the competitive binding assay, a limiting amount of antibody specific for the molecule of interest (either an antigen or hapten) is combined with specific volumes of solutions containing an unknown amount of the molecule to be detected and a solution containing a detectably labeled known amount of the molecule to be detected or an analog thereof. Labeled and unlabeled molecules then compete for the available binding sites on the antibody. Phase separation of the free and antibody-bound molecules allows measurement of the amount of label present in each phase, thus indicating the amount of antigen or hapten in the sample being tested. A number of variations in this general competitive binding assay currently exist.

In any of the known immunoassays, for practical purposes, one of the antibodies to the antigen (Ad41 long fiber protein, Ad41 short fiber protein or any one of Ad41 E3 proteins RL-1 to RL-6 or fragments thereof) will be typically bound to a solid phase and a second molecule, either the second antibody in a sandwich assay, or, in a competitive assay, the known amount of antigen, will bear a detectable label or reporter molecule in order to allow visual detection of an antibody-antigen reaction. When two antibodies are employed, as in the sandwich assay, it is only necessary that one of the antibodies be specific for, e.g., Ad41 short or long fiber protein or its antigenic fragments (the tail, the shaft or the knob). The following description will relate to a discussion of a typical forward sandwich assay; however, the general techniques are to be understood as being applicable to any of the contemplated immunoassays.

In the typical forward sandwich assay, a first antibody having specificity for, e.g., Ad41 short or long fiber protein or its antigenic fragments is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking, covalently binding, or physically adsorbing the molecule to the insoluble carrier. Following binding, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary, but will generally be in the range of about 2–40 minutes. Following the incubation period, the antibody subunit solid phase is washed and dried and incubated with a second antibody specific for a portion of the hapten. The second antibody is linked to a reporter molecule which is used to indicated the binding of the second antibody to the hapten.

By "reporter molecule", as used in the present specification and claims, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionucleotide-containing molecules.

In the case of an enzyme immunoassay (EIA), an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphates, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; and for peroxidase conjugates, 1,2-phenylenediamine, 5-aminosali-cyclic acid, or tolidine are commonly used. It is also possible to employ fluorogenic substrates, which yield a fluorescent product rather than the chromogenic substrates noted above.

In all cases, the enzyme-labeled antibody is added to the first antibody hapten complex, allowed to bind, and then excess reagent is washed away. A solution containing the appropriate substrate is then added to the ternary complex of antibody-antigen-antibody. The substrate will react with the enzyme linked to the second antibody, giving a qualitative visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic color visually detectable with a light microscope. As in the EIA, the fluorescent labeled antibody is allowed to bind to the first antibody-hapten complex. After washing off the unbound reagent, the remaining ternary complex is then exposed to the light of the appropriate wavelength, the fluorescence observed indicates the presence of the hapten of interest. Immunofluorescence and EIA techniques are both very well established in the art and are particularly preferred for the present method. However, other report molecules, such as radioisotope, chemiluminescent of bioluminescent molecules, may also be employed. It will be readily apparent to the skilled technician how to vary the procedure to suit the required purpose. It will also be apparent that the foregoing can be used to detect directly or indirectly (i.e., via antibodies) Type F adenoviruses.

In a preferred embodiment, the present invention also contemplates the use of the Ad41 E3 proteins RL-1 to RL-6 and Ad41 short fiber protein knob and Ad41 long fiber protein knob in enzyme immunoassays for selective detection of human enteric adenoviruses and in particular Ad41 and Ad40 in the stool of patients with gastroenteritis. EIA can give a clear, rapid result in about 2 hours and can therefore be more convenient and efficient and less expensive than a DNA probe test.

The present invention further contemplates an ELISA (enzyme-linked immunoabsorbent assay) test for the presence of antibodies to Ad41 long or short fiber protein or Ad41 E3 proteins RL-1 to RL-6 in serum or other specimens, such as saliva or the duodenal fluid from patients with gastroenteritis. The Ad41 long or short fiber protein "knob" of the present invention can be used, for example, to coat microtiter plates.

The present invention also contemplates the use of recombinant DNA molecules which contain at least one of the following genes: Ad41 long fiber protein gene, Ad41 short fiber protein gene, Ad41 E3 region gene encoding for proteins RL-1, RL-2, RL-3, RL-4, RL-5 or RL-6. The present invention contemplates using these recombinant DNA molecules in the development of diagnostic assays for Ad41. In another embodiment, the present invention contemplates the use of recombinant DNA molecules or derivatives thereof as described above, to generate antibodies useful in diagnostic and therapeutic techniques.

Another aspect of the present invention is the employment of the genetic information contained in the DNA of the Ad41 long fiber protein gene, the Ad41 short fiber protein gene and the Ad41 E3 gene. As defined herein, DNA is referred to as the genetic component of the virus (i.e., double-stranded DNA). Said DNA can be inserted in recombinant expression molecules such that, for example, the Ad41 long fiber protein gene encoded thereon is transcribed and the product can then be obtained. Such products can then be used as antigenic components to generate, for example, antibodies. The present invention contemplates the transformation of a host cell or organism with dsDNA of FIG. 1 (Ad41 long fiber protein gene) and/or FIG. 2 (Ad41 short fiber protein gene) and/or FIG. 4 (Ad41 E3 gene) which is capable of producing Ad41 (long or short) fiber protein or Ad41 E3 (RL-1 to RL-6) proteins wherein the host cell or organism is a bacterium (e.g., *E. coli*), yeast, insect cell or a mammalian cell.

The present invention also relates to DNA described above which can be used to generate probe nucleic acids for hybridization to homologous Ad41 or Ad40 DNA sequences, utilizing at least one of the following Ad41 genes: Ad41 long fiber protein gene, Ad41 short fiber protein gene or Ad41 E3 gene encoding the RL-1 to RL-6 Ad41 proteins.

Another aspect of this invention relates to a recombinant nucleic acid or an isolated nucleic acid molecule, said molecule defined herein to be dsDNA or recombinant DNA encoding Ad41 short fiber protein, Ad41 long fiber protein, or E3 proteins RL-1 to RL-6, or parts thereof. In one embodiment the recombinant nucleic acid molecule is complementary DNA (cDNA). It is considered within the scope of the present invention to include the cDNA molecule encoding the above-identified Ad41 proteins, or to regions or parts thereof including any base deletion, insertion or substitution or any other alteration with respect to nucleotide sequence or chemical composition (e.g. methylation and glycosylation). Additionally, the present invention is directed to restriction fragments and synthetic fragments from a nucleic acid encoding the above-identified Ad41 proteins. Moreover, another embodiment of the this invention is directed to the genomic Ad41 long fiber protein gene, Ad41 short fiber protein gene or E3 gene, which may include recombinant clones like cosmids encoding the entire gene or subclones encoding any region of the above-identified genes. Recombinant DNA encoding such subregions of the gene are useful as hybridization probes to detect the presence of the above-identified genes.

Methods considered useful in obtaining recombinant Ad41 cDNA are contained in Maniatis, et al., Molecular Cloning: A Laboratory Manual, Cold Spring Harbor Laboratory, N.Y. (2d Ed. 1989), for example, or any of the myriads of laboratory manuals on recombinant DNA technology which are widely available. Maniatis, et al. further discloses how to obtain deletions and insertions by site-directed mutagenesis, and subsequent selection of mutants for activity.

In a preferred embodiment, the present invention provides a dsDNA or recombinant DNA or cDNA having a nucleotide sequence encoding the Ad41 long fiber protein gene, as shown in FIG. 1. This sequence encodes the 60.6 kd Ad41 long fiber protein having the amino acid sequence shown in FIG. 1.

The present invention further provides a dsDNA or recombinant DNA or cDNA having a nucleotide sequence encoding the Ad41 short fiber as shown in FIG. 2, wherein this sequence encodes a 41.4 kd Ad41 short fiber protein having an amino acid sequence as shown in FIG. 3.

The present invention additionally provides a dsDNA or recombinant DNA or cDNA having a nucleotide sequence which encodes for the E3 region of Ad41 as shown in FIG. 4 wherein this region encodes six E3 proteins, RL-1 to RL-6. The E3 DNA sequence, from base 683 to base 1204, encodes RL-1, a 19.4 kd protein having an amino acid sequence as shown in FIG. 5. The E3 DNA sequence from base 1207 to base 2037 encodes RL-2, a 31.6 kd protein having an amino acid sequence as shown in FIG. 6. The E3 DNA sequence from base 1730 to base 1909 encodes RL-3, a 6.7 kd protein having an amino acid sequence as shown in FIG. 7. The E3 DNA sequence from base 2056 to base 2328 encodes RL-4, a 10.1 kd protein having an amino acid sequence as shown in FIG. 8. The E3 DNA sequence from base 2325 to base 2648 encodes RL-5, a 12.3 kd protein having an amino acid sequence as shown in FIG. 9. The E3 DNA sequence from base 2641 to base 3009 encodes RL-6, a 14.0 kd protein having an amino acid sequence as shown in FIG. 10.

The present invention further contemplates the preparation and use of a vaccine composition for the treatment of human adenovirus type 41 and related adenoviruses, including Ad40. The preparation of said vaccine is accomplished by utilization of at least one of the following adenovirus type 41 proteins: Ad41 short fiber protein, Ad41 long fiber protein, and E3 proteins RL-1 through RL-6. This is done by genetic engineering of at least one of the above-identified proteins and expressing at least one of these proteins in suitable vector/host cell systems such as bacteria, yeast or any other suitable vector/host system. In a further preferred embodiment, the vaccine of the present invention contemplates the use of cloned Ad41 long fiber protein "knob" or short fiber protein "knob" as an immunizing agent.

Previously used vaccines have generally comprised (I) an attenuated live virus type of vaccine in which the virus has been rendered avirulent but not killed by some form of genetic attenuation; or (II) specific viral components isolated and purified from the virus and inactivated by formalin or some other chemical or physical treatment. The present invention contemplates conventional Type II vaccines, wherein the specific viral components isolated and purified from the virus and inactivated by formalin or other treatments are contemplated to be at least one of Ad41 short fiber protein, AD41 long fiber protein, E3 RL-1, RL-2, RL-3, RL-4, RL-5 or RL-6 protein. In addition, with respect to Ad41 long and short fiber protein "viral component" also contemplates at least one of the tail, shaft or knob of these proteins. The present invention also contemplates the preparation of recombinant Ad41 proteins for use in a vaccine against Ad41 and Ad40.

In another embodiment, the present invention is directed to a Type II vaccine which is a combination of inactivated Ad41 and at least one of recombinant long and short Ad41 protein fibers and Ad41 E3 proteins RL-1 to RL-6.

By vaccine is meant an agent used to stimulate the immune system of a living organism so that protection against future harm is provided. Administration of a vaccine contemplated by the present invention to the patient (or animal) may be by any known or standard techniques. These include oral ingestion, intestinal intubation, or broncho-nasal spraying. Other methods of administration, such as intravenous injection, that allow the carrier microbe to reach the human or animal's bloodstream may be acceptable when the carrier microbe is unable to reproduce.

Recombinant DNA techniques for the preparation of recombinant Ad41 proteins for use in the preparation of vaccines are sufficiently well-known and widespread so as to be considered routine. In very general and broad terms, a method for use herein consists of transferring the genetic material, or more usually part of the genetic material, of one organism into a second organism so that the transferred genetic material becomes a permanent part of (recombines with) the genetic material of the organisms to which it is transferred. This usually consists of first obtaining a small piece of DNA from the parent organism either from a plasmid or a parent chromosome. A plasmid (also called an extrachromosomal element) is a hereditary unit that is physically separate from the chromosome of the cell. The DNA may be of any size and is often obtained by the action of a restriction endonuclease enzyme which acts to split DNA molecules at specific base-pair sites. In the present invention an Ad41 long fiber protein gene can be obtained which is a 1.9 kb SmaI-EcoRI DNA fragment or an Ad41 short fiber protein gene which is an EcoRV-AccI DNA fragment or an Ad41 E3 sequence which is an EcoRI-EspI DNA fragment. The DNA pieces of the Ad41 protein gene may be transferred into a host cell by various means such as transformation (uptake of naked DNA from the external environment, which can be artificially induced by the presence of various chemical agents, such as calcium ions). Other methods such as transduction are also suitable, wherein the DNA is packaged within a phage such as the co-called cosmid vector. Once the parent DNA is in the carrier cell, it may continue to exist as a separate piece (generally true of complete transmitted plasmids) or it may insert into the host cell chromosome and be reproduced with the chromosome during cell division.

Transferring genetic material is relatively straightforward. Any method capable of producing recombinant organisms comprising genes from pathogenic organisms that are expressed in avirulent microbes will suffice. The techniques of DNA isolation, gene cloning, and related techniques are disclosed in great detail in, for example, Recombinant DNA, Methods of Enzymology, Volume 68, Ray Wu, ed., Academic Press (1979), and Maniatis, T., et al., Molecular Cloning, Cold Spring Harbor Laboratories (1982), which are herein incorporated by reference and are applicable to the Ad41 protein gene of the present invention.

Vaccines of the present invention may be administered either as a liquid or in enteric-coated capsules. Such preparations are resistant to acid and enzymes in the stomach of the inoculated animal while dissolving in the intestines. Various enteric-coatings are known in the art, for example, as disclosed in U.S. Pat. Nos. 3,241,520 and 3,253,944 and are commercially available. A method suitable for preparation of enteric-coated capsules is described in U.S. Pat. No. 4,152,415, which is herein incorporated by reference, and can be easily modified to provide capsules containing the carrier microbes of the present invention.

Vaccines of the present invention may be administered orally in enteric-coated capsules as described above or may be administered parenterally (e.g., by intramuscular, subcutaneous, or intravenous injection). The amount required will vary with the antigenicity of the gene product and need only be an amount sufficient to induce an immune response typical of existing vaccines. Routine experimentation will easily establish the required amount. Typical initial dosages of vaccine could be about 0.001-100 mg antigen/kg body weight, with increasing amounts or multiple dosages used as needed to provide the desired level of protection.

The pharmaceutical carrier in which the vaccine is suspended or dissolved may be any solvent or solid that is non-toxic to the inoculated animal and compatible with the carrier organism or antigenic gene product. Suitable pharmaceutical carriers include liquid carriers, such as normal saline and other non-toxic salts at or near physiological concentrations, and solid carriers, such as talc or sucrose. Adjuvants, such as Freund's adjuvant, complete or incomplete, may be added to enhance the antigenicity via the bronchial tubes, the vaccine is suitably present in the form of an aerosol. Booster immunizations may be repeated numerous times with beneficial results.

In a preferred embodiment, the present invention contemplates a vaccine specific to Ad41 long fiber protein or at least one of its active fragments, e.g., the tail, the shaft or the knob of the long fiber protein, a vaccine specific to Ad41 short fiber protein or at least one of its active fragments, or a vaccine specific to at least one of the proteins of the Ad41 E3 region, RL-1 to RL-6.

A number of viral polypeptide preparations derived from viral coats or envelopes have been suggested as possible active components for vaccine compositions. For example, U.S. Pat. No. 4,470,967 describes vaccine preparations which are made by complexing viral polypeptide with a lectin, the latter element acting as adjuvant. A number of references, e.g., 4,344,935 or 4,356,169 or Morein, et al., *J. Gen. Virol.*, 64: 1557-1569, 1983, utilize a method of preparation of parainfluenza glycoprotein compositions in which the viral glycoprotein HN and F are solubilized with a detergent, to extract them from the viral envelope, followed by some method of phase separation in order to remove the detergent and lipids. The latter procedures produce a glycoprotein subunit which is not only substantially detergent free, but also lipid free. The latter type of highly purified glycoprotein is considered the preferred type of active agent for potential use of commercial vaccine.

In another aspect, the present invention relates to a method of treating infectious diseases caused by Ad41 and other related adenoviruses such as Ad40.

The subject invention also encompasses antibodies, either monoclonal or polyclonal, which are useful in the therapeutic control of infection by adenoviruses and in particular, Ad41 or Ad40. Said antibodies can be prepared as described above and by injecting mammalian species, e.g., human, horse, rabbit, sheep, mice, etc. with inactivated virus or derivatives thereof (i.e., the tail, shaft or knob) and then purifying said antibodies employing the detection systems contemplated and described herein.

In another embodiment, the present invention relates to the development of specific human or other eukaryotic (e.g., yeast, baculovirus, or Chinese hamster cells) polyclonal or monoclonal antibodies, as well as human-mouse chimeric polyclonal or monoclonal antibodies for administration in passive immunization against human adenoviruses, and in particular, Ad41 and Ad40. Immunization refers to the process of inducing a continuing high antibody level in an organism i.e., in humans, which is directed against an antigen to which the organism has been previously exposed.

Passive immunization, as defined herein, refers to resistance (e.g., temporary or sustained protection against infection) based on giving preformed antibodies to a patient from an in vivo or in vitro source. The main advantage of passive immunization is the prompt availability of large amounts of antibodies against human adenoviruses as described in the above embodiment of the present invention.

A chimeric antibody, as defined herein, is an antibody molecule made by recombinant DNA technology involving immunoglobulin genes of two different species. The human-mouse chimeric antibody is produced by combining the Fab portion of the mouse immunoglobulin gene and the Fc portion of the human immunoglobulin gene by recombinant DNA techniques. The production of human-mouse chimeric antibodies is advantageous since large amounts of antibodies can be produced by this system and human-mouse chimeric antibodies can be recognized by cells of the human immune system whereas non-chimeric antibodies would not be recognized as easily by cells (e.g., phagocytic) of the human immune system. The chimeric antibodies can be produced in large amounts in the mouse system and can recognize human adenoviruses as contemplated in the present invention. Human-mouse immunoglobulins have also been found to make large amounts of antibodies in yeast and this system is also contemplated herein. The following references discuss the methodologies for producing such antibodies and are incorporated herein by reference: Morrison, et al., *P.N.A.S.*, 81:6851 (1984); Horowitz, et al., *P.N.A.S.*, 85:8678 (1988); and Tao, et al., *J. Immunol.*, 143:2595 (1989).

The present invention also provides a kit for production of recombinant viral components of at least one of the above-identified Ad41 genes, to produce a vaccine to Ad41 or related viruses such as Ad40.

The present invention further contemplates the use of probes to detect, by hybridization, cellular DNA from infected tissue (e.g. biopsy material) carrying integrated structural Ad41 DNA (i.e., of the Ad41 long or short fiber protein gene or the Ad41 E3 gene). The probe can be DNA, cDNA, recombinant DNA or RNA. The present invention further contemplates a kit for detection of viral components of Ad41 or Ad40.

In one particular embodiment of the present invention, patient specimens (tissue or tissue extracts) containing biopsy material are smeared onto a standard microscope slide, then fixed with an appropriate fixative. The DNA or RNA probe, which has been labeled (e.g. with biotin-avidin-enzyme) is added. The slide is then placed onto a heating block for one or two minutes to allow both the probe and the target nucleic acids to be separated from their complementary strand (if double stranded). Non-hybridized probe DNA or RNA is removed by gentle washing. After a suitable detection complex is added, hybridization is detected with a light microscope following formation of a colored compound. Alternatively, the probe nucleic acid is labeled with a radioactive isotope and tissue to be tested lysed and their DNA fixed to, for example, nitrocellulose paper. Hybridization and DNA/RNA detection systems are well known in the art.

In a further embodiment, the present invention also relates to a kit for the detection of Ad41 long and/or short fiber protein and its active fragments and fiber protein of related adenoviruses and/or Ad41 E3 region proteins, the kit being compartmentalized to receive a first container adapted to contain an antibody having specificity for Ad41 long and/or short fiber protein or fragments thereof or Ad41 E3 region proteins, and a second container containing an antibody specific for first antibody and being labeled with a reporter molecule capable of giving a detectable signal. If the reporter molecule is an enzyme, then a third container, containing a substrate for said enzyme is provided.

In another embodiment, the present invention contemplates pharmaceutical compositions containing at least one of the above-identified Ad41 proteins, or derivatives thereof, for treatment of Ad41 or related viruses such as Ad40. The dosage effective amount of such compounds is from about 10 mg to about 100 mg per kg body weight.

The DNA sequence comprising the full-length 60.6 kD Ad41 (Tak) long fiber protein has been deposited with the European Molecular Biology Laboratory (EMBL) database and accorded the accession number X16583.

The DNA sequence comprising the full-length 41.4 kd Ad41 short fiber protein has been deposited with the EMBL database and accorded the accession number X17016. The Ad41 E3 DNA sequence has been deposited with the GenBank database and accorded the accession number M33160.

EXAMPLES

1. Cells and virus

Monolayer cultures of HEp-2, HeLa, Human Intestine (HI407), and Graham-293 cell lines were grown in Dulbecco's modification of Eagle minimal essential medium containing 10% fetal bovine serum (FBS). 293 cells were obtained from Flow Laboratories as well as ATCC; all other cell lines were from ATCC The adenovirus type 41 (Ad41) strain Tak (prototype strain 73-3544=ATCC #VR-930) used was provided by Dr. Jan C. de Jong, Bilthoven, The Netherlands, and originally passaged by him in HeLa (pl), Hep-2 (p4) and HeLa (p4). Detailed methods for growth and analysis of Ad41 were performed as described in Pieniazek et. al, Virology, 174:239-249 (1990).

2. Isolation of viral DNA

A modification of the method of Hirt, *J. Mol. Biol.*, 26: 365-369 (1967) was used. Monolayers of cells, grown in 25 cm2 flasks, are inoculated with the virus.

After 2 hours the solution was discarded and medium containing 5% FBS was added. The cultures were incubated at 37° C. for up to 15 days or until maximal CPE could be observed. The cells to be analyzed were scraped into the culture fluid and centrifuged at 1000×g for 5 min. The pellet was suspended in 0.5 ml of 1×SSPE buffer, pH 7.4, per flask. EDTA and SDS were added to the final concentration of 50 mM and 1%, respectively. The lysate was allowed to stand 20 min. at room temperature, then NaCl was added to 1.0 M and the sample was incubated at 4° C. for at least 1 hr. The high-molecular weight DNA and cell debris was pelleted by spinning the lysate for 15 min. in an Eppendorf centrifuge. T1 RNase was added to the clarified supernatant to a final concentration of 25 μg/ml. After incubation for 30 min. at 37° C. proteinase K (Boehringer-Mannheim) was added to 200 μg/ml and the sample was further incubated for 30 min. as above. The proteins were removed by one extraction with saturated phenol and one by phenol/chloroform mixture (1:1 v/v) according to the method of Maniatis et al., *Molecular Cloning: A Lab Manual,* Cold Spring Harbor, N.Y. (1982). DNA was precipitated with 3 volumes of ethanol. Nucleic acid, prepared from one culture flask was suspended in 50 μl of TE buffer (10 mM Tris-HCl, 1 mM EDTA, pH 7.5) and stored at 4° C.

3. Cloning of Ad41 EcoRI band B

Restriction enzyme EcoRI was purchased from BRL and is used according to manufacturer's specifications. Briefly, 3 μl of sample was digested at 37° C. with 5 units of enzyme in a final volume of 10 μl. Nucleic acid fragments were separated by electrophoresis on 1% agarose gels (BioRad) and the EcoRI band was identified by ethidium bromide staining. An agarose fragment containing this band was excised from the gel and the DNA was recovered using the GENECLEAN kit (Bio 101, La Jolla, Calif.). This isolated DNA fragment was mixed with EcoRI-digested plasmid pBluescript II SK(+) (Stratagene, La Jolla, Calif.) and treated with phage T4 DNA ligase (BRL). Next, competent cells of *E. coli* strain XL-1 Blue (Stratagene) were transformed with this ligation mixture and a clone containing Ad41 EcoRI band B was selected by estimating the size of the insert and restriction enzyme mapping.

4. DNA Sequencing

Preliminary sequencing was accomplished using the method of Deininger, *Analyt. Biochem.,* 135: 247-263 (1983). Ad41 EcoRI band B was isolated from an agarose gel as above and sheered by sonication. The ends of the sheered fragments were then filled with T4 DNA polymerase and the fragments were cloned into the SmaI site of the M13mp18 phage vector. Individual M13 clones were sequenced using the Sequenase kit from USB (Cleveland, Ohio). DNA sequences were analyzed using the IBI/Pustell software package from IBI (New Haven, Conn.) and their Gel Reader sonic digitizer.

After locating the start and end of the fiber gene by homology to the published Ad5 fiber sequence (Chroboczek and Jacrot, *Virology,* 161: 549-554, 1987), Ad41 long fiber gene was sequenced using a modified approach. Custom oligonucleotide primers were used in a double-stranded DNA sequencing protocol according to the Sequenase Version 2.0 manual (in the Sequenase kit from USB, Cleveland, Ohio). The complete sequence of the SmaI - EcoRI fragment (map position 86.4% to 92%), shown in FIG. 1, was assembled from fragment obtained by sequencing both strands including sequencing in the presence of dITP to resolve problems with compressions of the DNA.

The same method as described above was utilized for sequencing the Ad41 short fiber gene, and the complete sequence of the EcoRv-AccI fragment (map position 83.1% to 87.1%) is shown in FIG. 2. The Ad41 E3 region DNA was also sequenced in similar fashion, and the complete sequence of this EcoRI-EspI fragment (map position 74% to 83.9%) is shown in FIG. 4.

The protein coding regions of E3 DNA, short fiber DNA and long fiber DNA of human adenovirus type 41 Tak, are shown by the proteins RL-1 to RL-6, short fiber protein and long fiber protein as illustrated in the map of FIG. 11.

We claim:

1. An isolated nucleic acid having a sequence encoding a human adenovirus type 41 Tak long fiber protein.

2. The nucleic acid of claim 1 wherein said nucleic acid is DNA, cDNA, recombinant DNA or RNA.

3. The nucleic acid according to claim 1 having a nucleotide sequence which comprises:

```
CCCGGGCAAC  ATGCTCATCC  AAATCTCGCC  TAACATCACC  TTCAGTGTCG  TCTACAACGA
GGGCCCGTTG  TACGAGTAGG  TTTAGAGCGG  ATTGTAGTGG  AAGTCACAGC  AGATGTTGCT

GATAAACAGT  GGGTATGCTT  TTACTTTTAA  ATGGTCAGCC  GAACCGGGAA  AACCTTTTCA
CTATTTGTCA  CCCATACGAA  AATGAAAATT  TACCAGTCGG  CTTGGCCCTT  TTGGAAAAGT

CCCACCTACC  GCTGTATTTT  GCTACATAAC  TGAACAATAA  AATCATTGCA  GGCACAATCT
GGGTGGATGG  CGACATAAAA  CGATGTATTG  ACTTGTTATT  TTAGTAACGT  CCGTGTTAGA

TCGCATTTCT  TTTTTTCCAG  ATG AAA CGA GCC AGA CTT GAA GAT GAC TTC AAC CCC
AGCGTAAAGA  AAAAAAGGTC  TAC TTT GCT CGG TCT GAA CTT CTA CTG AAG TTG GGG

GTC TAC CCT TAC GAA CAC TAC AAT CCC CTT GAC ATC CCA TTT ATT ACA CCC
CAG ATG GGA ATG CTT GTG ATG TTA GGG GAA CTG TAG GGT AAA TAA TGT GGG

CCG TTT GCC TCC TCC AAC GGC TTG CAA GAA AAA CCA CCG GGA GTC CTC AGC
GGC AAA CGG AGG AGG TTG CCG AAC GTT CTT TTT GGT GGC CCT CAG GAG TCG

CTG AAA TAC ACT GAT CCA CTT ACA ACC AAA AAC GGG GCT TTA ACC TTA AAA
GAC TTT ATG TGA CTA GGT GAA TGT TGG TTT TTG CCC CGA AAT TGG AAT TTT

CTG GGC ACG GGA CTA AAC ATT GAT GAA AAT GGA GAT CTT TCT TCA GAT GCT
GAC CCG TGC CCT GAT TTG TAA CTA CTT TTA CCT CTA GAA AGA AGT CTA CGA

AGC GTG GAA GTT AGC GCC CCT ATT ACT AAA ACC AAC AAA ATC GTA GGT TTA
```

-continued

TCG CAC CTT CAA TCG CGG GGA TAA TGA TTT TGG TTG TTT TAG CAT CCA AAT

AAT TAC ACT AAA CCT CTC GCC CTG CGA AGT AAC GCG CTC ACT CTT TCT TAC
TTA ATG TGA TTT GGA GAG CGG GAC GCT TCA TTG CGC GAG TGA GAA AGA ATG

AAC GCA CCC TTA AAC GTA GTA AAT AAC AAT TTA GCT TTA AAT ATC TCA CAA
TTG CGT GGG AAT TTG CAT CAT TTA TTG TTA AAT CGA AAT TTA TAG AGT GTT

CCT GTC ACT GTT AAT GCA AAC AAC GAA CTT TCT CTC TTA ATA GAC GCC CCA
GGA CAG TGA CAA TTA CGT TTG TTG CTT GAA AGA GAG AAT TAT CTG CGG GGT

CTT AAT GCT GAC ACG GGC ACT CTT CGC CTT CAA AGT GCT GCA CCT CTT GGA
GAA TTA CGA CTG TGC CCG TGA GAA GCG GAA GTT TCA CGA CGT GGA GAA CCT

CTA GTG GAC AAA ACA CTA AAA GTT TTG TTT TCT AGC CCC CTC TAT CTA GAT
GAT CAC CTG TTT TGT GAT TTT CAA AAC AAA AGA TCG GGG GAG ATA GAT CTA

AAT AAC TTT CTT ACA CTA GCC ATT GAA CGC CCG CTA GCT CTA TCC AGT AGC
TTA TTG AAA GAA TGT GAT CGG TAA CTT GCG GGC GAT CGA GAT AGG TCA TCG

AGA GCA GTG ACC CTT AAG TAT TCA CCA CCT TTA AAA ATA GAA AAC GAA AAC
TCT CGT CAC TGG GAA TTC ATA AGT GGT GGA AAT TTT TAT CTT TTG CTT TTG

TTA ACC CTA AGC ACA GGC GGG CCT TTT ACT GTA AGC GGG GGA AAT CTA AAC
AAT TGG GAT TCG TGT CCG CCC GGA AAA TGA CAT TCG CCC CCT TTA GAT TTG

TTA ACA ACA TCG GCA CCT CTC TCC GTG CAA AAC AAC TCT CTC TCC TTA GTC
AAT TGT TGT AGC CGT GGA GAG AGG CAC GTT TTG TTG AGA GAG AGG AAT CAG

ATT ACT TCT CCT TTA AAA GTT ATT AAT TCT ATG TTA GCC GTT GGG GTT AAC
TAA TGA AGA GGA AAT TTT CAA TAA TTA AGA TAC AAT CGG CAA CCC CAA TTG

CCG CCT TTT ACC ATC ACT GAC TCT GGA TTA GCT ATG GAC TTA GGA GAC GGT
GGC GGA AAA TGG TAG TGA CTG AGA CCT AAT CGA TAC CTG AAT CCT CTG CCA

CTT GCA CTA GGT GGC TCT AAG TTA ATA ATC AAT CTT GGT CCA GGT TTA CAA
GAA CGT GAT CCA CCG AGA TTC AAT TAT TAG TTA GAA CCA GGT CCA AAT GTT

ATG TCT AAT GGA GCT ATT ACT TTA GCA CTA GAT GCA GCG CTG CCT TTG CAA
TAC AGA TTA CCT CGA TAA TGA AAT CGT GAT CTA CGT CGC GAC GGA AAC GTT

TAT AGA GAC AAC CAA CTT CAA CTC AGA ATT GGC TCA ACA TCT GGC TTA ATT
ATA TCT CTG TTG GTT GAA GTT GAG TCT TAA CCG AGT TGT AGA CCG AAT TAA

ATG AGC GGA GTA ACA CAA ACA TTA AAC GTC AAT GCC AAT ACC GGC AAA GGT
TAC TCG CCT CAT TGT GTT TGT AAT TTG CAG TTA CGG TTA TGG CCG TTT CCA

CTT GCT GTT GAA AAC AAC TCA CTA GTT GTT AAG CTT GGG AAC GGT CTT CGC
GAA CGA CAA CTT TTG TTG AGT GAT CAA CAA TTC GAA CCC TTG CCA GAA GCG

TTT GAT AGC TGG GGA AGC ATA ACT GTC TCG CCT ACT ACC ACT ACC CCT ACC
AAA CTA TCG ACC CCT TCG TAT TGA CAG AGC GGA TGA TGG TGA TGG GGA TGG

ACC CTA TGG ACC ACC GCA GAC CCA TCA CCT AAC GCC ACT TTT TAT GAA TCA
TGG GAT ACC TGG TGG CGT CTG GGT AGT GGA TTG CGG TGA AAA ATA CTT AGT

CTA GAC GCC AAA GTG TGG CTA GTT TTA GTA AAA TGC AAC GGC ATG GTT AAC
GAT CTG CGG TTT CAC ACC GAT CAA AAT CAT TTT ACG TTG CCG TAC CAA TTG

GGG ACC ATA TCC ATT AAA GCT CAG AAA GGC ATT TTA CTT AGA CCT ACA GCT
CCC TGG TAT AGG TAA TTT CGA GTC TTT CCG TAA AAT GAA TCT GGA TGT CGA

AGT TTT ATT TCC TTT GTC ATG TAT TTC TAC AGC GAT GGA ACA TGG AGA AAA
TCA AAA TAA AGG AAA CAG TAC ATA AAG ATG TCG CTA CCT TGT ACC TCT TTT

AAC TAT CCC GTG TTT GAC AAC GAA GGG ATA CTA GCA AAC AGT GCC ACG TGG
TTG ATA GGG CAC AAA CTG TTG CTT CCC TAT GAT CGT TTG TCA CGG TGC ACC

GGT TAT CGA CAA GGA CAG TCT GCC AAC ACT AAC GTT TCT AAT GCT GTA GAA
CCA ATA GCT GTT CCT GTC AGA CGG TTG TGA TTG CAA AGA TTA CGA CAT CTT

TTT ATG CCT AGC TCT AAA AGA TAT CCC AAT CAA AAA GGT TCT GAA GTT CAG
AAA TAC GGA TCG AGA TTT TCT ATA GGG TTA GTT TTT CCA AGA CTT CAA GTC

AAC ATG GCT CTT ACC TAC ACT TTT TTG CAA GGT GAT CCT AAC ATG GCC ATA
TTG TAC CGA GAA TGG ATG TGA AAA AAC GTT CCA CTA GGA TTG TAC CGG TAT

TCC TTT CAG AGT ATT TAT AAT CAT GCA TTA GAA GGC TAC TCA TTA AAA TTT
AGG AAA GTC TCA TAA ATA TTA GTA CGT AAT CTT CCG ATG AGT AAT TTT AAA

ACC TGG CGC GTT CGA AAT AAT GAA CGT TTT GAC ATC CCC TGC TGC TCA TTT
TGG ACC GCG CAA GCT TTA TTA CTT GCA AAA CTG TAG GGG ACG ACG AGT AAA

-continued

```
TCT TAT GTA  ACA GAA CAA  TAA A ATATTGTTGT TTTTGTTTTT ATAACTTTAT
AGA ATA CAT  TGT CTT GTT  ATT T TATAACAACA AAAACAAAAA TATTGAAATA

TGATACTTTT  ACAGAATTC
ACTATGAAAA  TGTCTTAAG
```

4. The nucleic acid according to claim 1 having a nucleotide sequence which comprises:

```
                                          ATG AAA CGA GCC  AGA CTT GAA  GAT GAC TTC  AAC CCC
                                          TAC TTT GCT CGG  TCT GAA CTT  CTA CTG AAG  TTG GGG

GTC TAC CCT  TAC GAA CAC  TAC AAT CCC  CTT GAC ATC  CCA TTT ATT  ACA CCC
CAG ATG GGA  ATG CTT GTG  ATG TTA GGG  GAA CTG TAG  GGT AAA TAA  TGT GGG

CCG TTT GCC  TCC TCC AAC  GGC TTG CAA  GAA AAA CCA  CCG GGA GTC  CTC AGC
GGC AAA CGG  AGG AGG TTG  CCG AAC GTT  CTT TTT GGT  GGC CCT CAG  GAG TCG

CTG AAA TAC  ACT GAT CCA  CTT ACA ACC  AAA AAC GGG  GCT TTA ACC  TTA AAA
GAC TTT ATG  TGA CTA GGT  GAA TGT TGG  TTT TTG CCC  CGA AAT TGG  AAT TTT

CTG GGC ACG  GGA CTA AAC  ATT GAT GAA  AAT GGA GAT  CTT TCT TCA  GAT GCT
GAC CCG TGC  CCT GAT TTG  TAA CTA CTT  TTA CCT CTA  GAA AGA AGT  CTA CGA

AGC GTG GAA  GTT AGC GCC  CCT ATT ACT  AAA ACC AAC  AAA ATC GTA  GGT TTA
TCG CAC CTT  CAA TCG CGG  GGA TAA TGA  TTT TGG TTG  TTT TAG CAT  CCA AAT

AAT TAC ACT  AAA CCT CTC  GCC CTG CGA  AGT AAC GCG  CTC ACT CTT  TCT TAC
TTA ATG TGA  TTT GGA GAG  CGG GAC GCT  TCA TTG CGC  GAG TGA GAA  AGA ATG

AAC GCA CCC  TTA AAC GTA  GTA AAT AAC  AAT TTA GCT  TTA AAT ATC  TCA CAA
TTG CGT GGG  AAT TTG CAT  CAT TTA TTG  TTA AAT CGA  AAT TTA TAG  AGT GTT

CCT GTC ACT  GTT AAT GCA  AAC AAC GAA  CTT TCT CTC  TTA ATA GAC  GCC CCA
GGA CAG TGA  CAA TTA CGT  TTG TTG CTT  GAA AGA GAG  AAT TAT CTG  CGG GGT

CTT AAT GCT  GAC ACG GGC  ACT CTT CGC  CTT CAA AGT  GCT GCA CCT  CTT GGA
GAA TTA CGA  CTG TGC CCG  TGA GAA GCG  GAA GTT TCA  CGA CGT GGA  GAA CCT

CTA GTG GAC  AAA ACA CTA  AAA GTT TTG  TTT TCT AGC  CCC CTC TAT  CTA GAT
GAT CAC CTG  TTT TGT GAT  TTT CAA AAC  AAA AGA TCG  GGG GAG ATA  GAT CTA

AAT AAC TTT  CTT ACA CTA  GCC ATT GAA  CGC CCG CTA  GCT CTA TCC  AGT AGC
TTA TTG AAA  GAA TGT GAT  CGG TAA CTT  GCG GGC GAT  CGA GAT AGG  TCA TCG

AGA GCA GTG  ACC CTT AAG  TAT TCA CCA  CCT TTA AAA  ATA GAA AAC  GAA AAC
TCT CGT CAC  TGG GAA TTC  ATA AGT GGT  GGA AAT TTT  TAT CTT TTG  CTT TTG

TTA ACC CTA  AGC ACA GGC  GGG CCT TTT  ACT GTA AGC  GGG GGA AAT  CTA AAC
AAT TGG GAT  TCG TGT CCG  CCC GGA AAA  TGA CAT TCG  CCC CCT TTA  GAT TTG

TTA ACA ACA  TCG GCA CCT  CTC TCC GTG  CAA AAC AAC  TCT CTC TCC  TTA GTC
AAT TGT TGT  AGC CGT GGA  GAG AGG CAC  GTT TTG TTG  AGA GAG AGG  AAT CAG

ATT ACT TCT  CCT TTA AAA  GTT ATT AAT  TCT ATG TTA  GCC GTT GGG  GTT AAC
TAA TGA AGA  GGA AAT TTT  CAA TAA TTA  AGA TAC AAT  CGG CAA CCC  CAA TTG

CCG CCT TTT  ACC ATC ACT  GAC TCT GGA  TTA GCT ATG  GAC TTA GGA  GAC GGT
GGC GGA AAA  TGG TAG TGA  CTG AGA CCT  AAT CGA TAC  CTG AAT CCT  CTG CCA

CTT GCA CTA  GGT GGC TCT  AAG TTA ATA  ATC AAT CTT  GGT CCA GGT  TTA CAA
GAA CGT GAT  CCA CCG AGA  TTC AAT TAT  TAG TTA GAA  CCA GGT CCA  AAT GTT

ATG TCT AAT  GGA GCT ATT  ACT TTA GCA  CTA GAT GCA  GCG CTG CCT  TTG CAA
TAC AGA TTA  CCT CGA TAA  TGA AAT CGT  GAT CTA CGT  CGC GAC GGA  AAC GTT

TAT AGA GAC  AAC CAA CTT  CAA CTC AGA  ATT GGC TCA  ACA TCT GGC  TTA ATT
ATA TCT CTG  TTG GTT GAA  GTT GAG TCT  TAA CCG AGT  TGT AGA CCG  AAT TAA

ATG AGC GGA  GTA ACA CAA  ACA TTA AAC  GTC AAT GCC  AAT ACC GGC  AAA GGT
TAC TCG CCT  CAT TGT GTT  TGT AAT TTG  CAG TTA CGG  TTA TGG CCG  TTT CCA

CTT GCT GTT  GAA AAC AAC  TCA CTA GTT  GTT AAG CTT  GGG AAC GGT  CTT CGC
GAA CGA CAA  CTT TTG TTG  AGT GAT CAA  CAA TTC GAA  CCC TTG CCA  GAA GCG

TTT GAT AGC  TGG GGA AGC  ATA ACT GTC  TCG CCT ACT  ACC ACT ACC  CCT ACC
AAA CTA TCG  ACC CCT TCG  TAT TGA CAG  AGC GGA TGA  TGG TGA TGG  GGA TGG

ACC CTA TGG  ACC ACC GCA  GAC CCA TCA  CCT AAC GCC  ACT TTT TAT  GAA TCA
TGG GAT ACC  TGG TGG CGT  CTG GGT AGT  GGA TTG CGG  TGA AAA ATA  CTT AGT
```

-continued

| | | | | | | | | | | | | | | | |
|---|---|---|---|---|---|---|---|---|---|---|---|---|---|---|---|
| GAA | GAC | GAC | TTC | AAC | CCC | GTC | TAC | CCC | TAT | GAC | ACC | TTC | TCA | ACT | CCC |
| CTT | CTG | CTG | AAG | TTG | GGG | CAG | ATG | GGG | ATA | CTG | TGG | AAG | AGT | TGA | GGG |
| AGC | ATC | CCC | TAT | GTA | GCT | CCG | CCC | TTC | GTT | TCT | TCT | GAC | GGG | TTA | CAG |
| TCG | TAG | GGG | ATA | CAT | CGA | GGC | GGG | AAG | CAA | AGA | AGA | CTG | CCC | AAT | GTC |
| GAA | AAA | CCC | CCA | GGA | GTT | TTA | GCA | CTC | AAG | TAC | ACT | GAC | CCC | ATT | ACT |
| CTT | TTT | GGG | GGT | CCT | CAA | AAT | CGT | GAG | TTC | ATG | TGA | CTG | GGG | TAA | TGA |
| ACC | AAT | GCT | AAG | CAT | GAG | CTT | ACT | TTA | AAA | CTT | GGA | AGC | AAC | ATA | ACT |
| TGG | TTA | CGA | TTC | GTA | CTC | GAA | TGA | AAT | TTT | GAA | CCT | TCG | TTG | TAT | TGA |
| TTA | GAA | AAT | GGG | TTA | CTT | TCG | GCC | ACA | GTT | CCC | ACT | GTT | TCT | CCT | CCC |
| AAT | CTT | TTA | CCC | AAT | GAA | AGC | CGG | TGT | CAA | GGG | TGA | CAA | AGA | GGA | GGG |
| CTT | ACA | AAC | AGT | AAC | AAC | TCC | CTG | GGT | TTA | GCC | ACA | TCC | GCT | CCC | ATA |
| GAA | TGT | TTG | TCA | TTG | TTG | AGG | GAC | CCA | AAT | CGG | TGT | AGG | CGA | GGG | TAT |
| GCT | GTA | TCA | GCT | AAC | TCT | CTC | ACA | TTG | GCC | ACC | GCC | GCA | CCA | CTG | ACA |
| CGA | CAT | AGT | CGA | TTG | AGA | GAG | TGT | AAC | CGG | TGG | CGG | CGT | GGT | GAC | TGT |
| GTA | AGC | AAC | AAC | CAG | CTT | AGT | ATT | AAC | GCG | GGC | AGA | GGT | TTA | GTT | ATA |
| CAT | TCG | TTG | TTG | GTC | GAA | TCA | TAA | TTG | CGC | CCG | TCT | CCA | AAT | CAA | TAT |
| ACT | AAC | AAT | GCC | TTA | ACA | GTT | AAT | CCT | ACC | GGA | GCG | CTA | GGT | TTC | AAT |
| TGA | TTG | TTA | CGG | AAT | TGT | CAA | TTA | GGA | TGG | CCT | CGC | GAT | CCA | AAG | TTA |
| AAC | ACA | GGA | GCT | TTA | CAA | TTA | AAT | GCT | GCA | GGA | GGA | ATG | AGA | GTG | GAC |
| TTG | TGT | CCT | CGA | AAT | GTT | AAT | TTA | CGA | CGT | CCT | CCT | TAC | TCT | CAC | CTG |
| GGT | GCC | AAC | TTA | ATT | CTT | CAT | GTA | GCA | TAT | CCC | TTT | GAA | GCA | ATC | AAC |
| CCA | CGG | TTG | AAT | TAA | GAA | GTA | CAT | CGT | ATA | GGG | AAA | CTT | CGT | TAG | TTG |
| CAG | CTA | ACA | CTG | CGA | TTA | GAA | AAC | GGG | TTA | GAA | GTA | ACC | AGC | GGA | GGA |
| GTC | GAT | TGT | GAC | GCT | AAT | CTT | TTG | CCC | AAT | CTT | CAT | TGG | TCG | CCT | CCT |
| AAG | CTT | AAC | GTT | AAG | TTG | GGA | TCA | GGC | CTC | CAA | TTT | GAC | AGT | AAC | GGA |
| TTC | GAA | TTG | CAA | TTC | AAC | CCT | AGT | CCG | GAG | GTT | AAA | CTG | TCA | TTG | CCT |
| CGC | ATT | GCT | ATT | AGT | AAT | AGC | AAC | CGA | ACT | CGA | AGT | GTA | CCA | TCC | CTC |
| GCG | TAA | CGA | TAA | TCA | TTA | TCG | TTG | GCT | TGA | GCT | TCA | CAT | GGT | AGG | GAG |
| ACT | ACC | ATT | TGG | TCT | ATC | TCG | CCT | ACG | CCT | AAC | TGC | TCC | ATT | TAT | GAA |
| TGA | TGG | TAA | ACC | AGA | TAG | AGC | GGA | TGC | GGA | TTG | ACG | AGG | TAA | ATA | CTT |
| ACC | CAA | GAT | GCA | AAC | CTA | TTT | CTT | TGT | CTA | ACT | AAA | AAC | GGA | GCT | CAC |
| TGG | GTT | CTA | CGT | TTG | GAT | AAA | GAA | ACA | GAT | TGA | TTT | TTG | CCT | CGA | GTG |
| GTA | TTA | GGT | ACT | ATA | ACA | ATC | AAA | GGT | CTT | AAA | GGA | GCA | CTG | CGG | GAA |
| CAT | AAT | CCA | TGA | TAT | TGT | TAG | TTT | CCA | GAA | TTT | CCT | CGT | GAC | GCC | CTT |
| ATG | CAC | GAT | AAC | GCT | CTA | TCT | TTA | AAA | CTT | CCC | TTT | GAC | AAT | CAG | GGA |
| TAC | GTG | CTA | TTG | CGA | GAT | AGA | AAT | TTT | GAA | GGG | AAA | CTG | TTA | GTC | CCT |
| AAT | TTA | CTT | AAC | TGT | GCC | TTG | GAA | TCA | TCC | ACC | TGG | CGT | TAC | CAG | GAA |
| TTA | AAT | GAA | TTG | ACA | CGG | AAC | CTT | AGT | AGG | TGG | ACC | GCA | ATG | GTC | CTT |
| ACC | AAC | GCA | GTG | GCC | TCT | AAT | GCC | TTA | ACA | TTT | ATG | CCC | AAC | AGT | ACA |
| TGG | TTG | CGT | CAC | CGG | AGA | TTA | CGG | AAT | TGT | AAA | TAC | GGG | TTG | TCA | TGT |
| GTG | TAT | CCA | CGA | AAC | AAA | ACC | GCT | CAC | CCG | GGC | AAC | ATG | CTC | ATC | CAA |
| CAC | ATA | GGT | GCT | TTG | TTT | TGG | CGA | GTG | GGC | CCG | TTG | TAC | GAG | TAG | GTT |
| ATC | TCG | CCT | AAC | ATC | ACC | TTC | AGT | GTC | GTC | TAC | AAC | GAG | ATA | AAC | AGT |
| TAG | AGC | GGA | TTG | TAG | TGG | AAG | TCA | CAG | CAG | ATG | TTG | CTC | TAT | TTG | TCA |
| GGG | TAT | GCT | TTT | ACT | TTT | AAA | TGG | TCA | GCC | GAA | CCG | GGA | AAA | CCT | TTT |
| CCC | ATA | CGA | AAA | TGA | AAA | TTT | ACC | AGT | CGG | CTT | GGC | CCT | TTT | GGA | AAA |
| CAC | CCA | CCT | ACC | GCT | GTA | TTT | TGC | TAC | ATA | ACT | GAA | CAA | TAA | | |
| GTG | GGT | GGA | TGG | CGA | CAT | AAA | ACG | ATG | TAT | TGA | CTT | GTT | ATT | | |

| | | | | | |
|---|---|---|---|---|---|
| AATCATTGCA | GGCACAATCT | TCGCATTTCT | TTTTTTCCAG | ATGAAACGAG | CCAGACTTGA |
| TTAGTAACGT | CCGTGTTAGA | AGCGTAAAGA | AAAAAAGGTC | TACTTTGCTC | GGTCTGAACT |
| AGATGACTTC | AACCCCGTCT | AC | | | |
| TCTACTGAAG | TTGGGGCAGA | TG | | | |

9. The nucleic acid according to claim 6 having a nucleotide sequence which comprises:

-continued

CTA GAC GCC AAA GTG TGG CTA GTT TTA GTA AAA TGC AAC GGC ATG GTT AAC
GAT CTG CGG TTT CAC ACC GAT CAA AAT CAT TTT ACG TTG CCG TAC CAA TTG

GGG ACC ATA TCC ATT AAA GCT CAG AAA GGC ATT TTA CTT AGA CCT ACA GCT
CCC TGG TAT AGG TAA TTT CGA GTC TTT CCG TAA AAT GAA TCT GGA TGT CGA

AGT TTT ATT TCC TTT GTC ATG TAT TTC TAC AGC GAT GGA ACA TGG AGA AAA
TCA AAA TAA AGG AAA CAG TAC ATA AAG ATG TCG CTA CCT TGT ACC TCT TTT

AAC TAT CCC GTG TTT GAC AAC GAA GGG ATA CTA GCA AAC AGT GCC ACG TGG
TTG ATA GGG CAC AAA CTG TTG CTT CCC TAT GAT CGT TTG TCA CGG TGC ACC

GGT TAT CGA CAA GGA CAG TCT GCC AAC ACT AAC GTT TCT AAT GCT GTA GAA
CCA ATA GCT GTT CCT GTC AGA CGG TTG TGA TTG CAA AGA TTA CGA CAT CTT

TTT ATG CCT AGC TCT AAA AGA TAT CCC AAT CAA AAA GGT TCT GAA GTT CAG
AAA TAC GGA TCG AGA TTT TCT ATA GGG TTA GTT TTT CCA AGA CTT CAA GTC

AAC ATG GCT CTT ACC TAC ACT TTT TTG CAA GGT GAT CCT AAC ATG GCC ATA
TTG TAC CGA GAA TGG ATG TGA AAA AAC GTT CCA CTA GGA TTG TAC CGG TAT

TCC TTT CAG AGT ATT TAT AAT CAT GCA TTA GAA GGC TAC TCA TTA AAA TTT
AGG AAA GTC TCA TAA ATA TTA GTA CGT AAT CTT CCG ATG AGT AAT TTT AAA

ACC TGG CGC GTT CGA AAT AAT GAA CGT TTT GAC ATC CCC TGC TGC TCA TTT
TGG ACC GCG CAA GCT TTA TTA CTT GCA AAA CTG TAG GGG ACG ACG AGT AAA

TCT TAT GTA ACA GAA CAA TAA A
AGA ATA CAT TGT CTT GTT ATT T

5. The nucleic acid according to claim 1 having a nucleotide sequence encoding an amino acid sequence for Ad41 long fiber protein which comprises:

Met Lys Arg Ala Arg Leu Glu Asp Asp Phe Asn Pro
Val Tyr Pro Tyr Glu His Tyr Asn Pro Leu Asp Ile Pro Phe Ile Thr Pro
Pro Phe Ala Ser Ser Asn Gly Leu Gln Glu Lys Pro Pro Gly Val Leu Ser
Leu Gly Thr Gly Leu Asn Ile Asp Glu Asn Gly Asp Leu Ser Ser Asp Ala
Ser Val Glu Val Ser Ala Pro Ile Thr Lys Thr Asn Lys Ile Val Gly Leu
Asn Tyr Thr Lys Pro Leu Ala Leu Arg Ser Asn Ala Leu Thr Leu Ser Tyr
Asn Ala Pro Leu Asn Val Val Asn Asn Asn Leu Ala Leu Asn Ile Ser Gln
Pro Val Thr Val Asn Ala Asn Asn Glu Leu Ser Leu Leu Ile Asp Ala Pro
Leu Asn Ala Asp Thr Gly Thr Leu Arg Leu Gln Ser Ala Ala Pro Leu Gly
Leu Val Asp Lys Thr Leu Lys Val Leu Phe Ser Ser Pro Leu Tyr Leu Asp
Asn Asn Phe Leu Thr Leu Ala Ile Glu Arg Pro Leu Ala Leu Ser Ser Ser
Arg Ala Val Thr Leu Lys Tyr Ser Pro Pro Leu Lys Ile Glu Asn Glu Asn Leu
Thr Leu Ser Thr Gly Gly Pro Phe Thr Val Ser Gly Gly Asn Leu Asn Leu Thr
Thr Ser Ala Pro Leu Ser Val Gln Asn Asn Ser Leu Ser Leu Val Ile Thr Ser
Pro Leu Lys Val Ile Asn Ser Met Leu Ala Val Gly Val Asn Pro Pro Phe Thr
Ile Thr Asp Ser Gly Leu Ala Met Asp Leu Gly Asp Gly Leu Ala Leu Gly Gly
Ser Lys Leu Ile Ile Asn Leu Gly Pro Gly Leu Gln Met Ser Asn Gly Ala Ile
Thr Leu Ala Leu Asp Ala Ala Leu Pro Leu Gln Tyr Arg Asp Asn Gln Leu Gln
Leu Arg Ile Gly Ser Thr Ser Gly Leu Ile Met Ser Gly Val Thr Gln Thr Leu
Asn Val Asn Ala Asn Thr Gly Lys Gly Leu Ala Val Glu Asn Asn Ser Leu Val
Val Lys Leu Gly Asn Gly Leu Arg Phe Asp Ser Trp Gly Ser Ile Thr Val Ser
Pro Thr Thr Thr Thr Pro Thr Thr Leu Trp Thr Thr Ala Asp Pro Ser Pro Asn
Ala Thr Phe Tyr Glu Ser Leu Asp Ala Lys Val Trp Leu Val Leu Val Lys Cys
Asn Gly Met Val Asn Gly Thr Ile Ser Ile Lys Ala Gln Lys Gly Ile Leu Leu
Arg Pro Thr Ala Ser Phe Ile Ser Phe Val Met Tyr Phe Tyr Ser Asp Gly Thr
Trp Arg Lys Asn Tyr Pro Val Phe Asp Asn Glu Gly Ile Leu Ala Asn Ser Ala
Thr Trp Gly Tyr Arg Gln Gly Gln Ser Ala Asn Thr Asn Val Ser Asn Ala Val
Glu Phe Met Pro Ser Ser Lys Arg Tyr Pro Asn Gln Lys Gly Ser Glu Val Gln
Asn Met Ala Leu Thr Tyr Thr Phe Leu Gln Gly Asp Pro Asn Met Ala Ile Ser
Phe Gln Ser Ile Tyr Asn His Ala Leu Glu Gly Tyr Ser Leu Lys Phe Thr Trp
Arg Val Arg Asn Asn Glu Arg Phe Asp Ile Pro Cys Cys Ser Phe Ser Tyr Val
Thr Glu Gln

6. An isolated nucleic acid having a sequence encoding a human adenovirus type 41 Tak short fiber protein.

7. The nucleic acid of claim 6 wherein said nucleic acid is DNA, cDNA, recombinant DNA or RNA.

8. The nucleic acid according to claim 6 having a nucleotide sequence which comprises:

GATATCAGTT GTTTGTCAAG TTTTTCCAGC AGCACCACCT GCCCTTCCTC CCAACTTTCG
CTATAGTCAA CAAACAGTTC AAAAAGGTCG TCGTGGTGGA CGGGAAGGAG GGTTGAAAGC

TAGGGGATGT GCCAACGGGC AGCAAACTTT CTCCACGTCC TAAAGGGTAT ATCGGTGTTC
ATCCCCTACA CGGTTGCCCG TCGTTTGAAA GAGGTGCAGG ATTTCCCATA TAGCCACAAG

ACCTTTTTAC CCTGACCCAC GATCTTCATC TTGCAG ATG AAA AGA ACC AGA ATT
TGGAAAAATG GGACTGGGTG CTAGAAGTAG AACGTC TAC TTT TCT TGG TCT TAA

| | | | | | | | | | | | | | | | |
|---|---|---|---|---|---|---|---|---|---|---|---|---|---|---|---|
| | | | | | | | | | | ATG<br>TAC | AAA<br>TTT | AGA<br>TCT | ACC<br>TGG | AGA<br>TCT | ATT<br>TAA |
| GAA<br>CTT | GAC<br>CTG | GAC<br>CTG | TTC<br>AAG | AAC<br>TTG | CCC<br>GGG | GTC<br>CAG | TAC<br>ATG | CCC<br>GGG | TAT<br>ATA | GAC<br>CTG | ACC<br>TGG | TTC<br>AAG | TCA<br>AGT | ACT<br>TGA | CCC<br>GGG |
| AGC<br>TCG | ATC<br>TAG | CCC<br>GGG | TAT<br>ATA | GTA<br>CAT | GCT<br>CGA | CCG<br>GGC | CCC<br>GGG | TTC<br>AAG | GTT<br>CAA | TCT<br>AGA | TCT<br>AGA | GAC<br>CTG | GGG<br>CCC | TTA<br>AAT | CAG<br>GTC |
| GAA<br>CTT | AAA<br>TTT | CCC<br>GGG | CCA<br>GGT | GGA<br>CCT | GTT<br>CAA | TTA<br>AAT | GCA<br>CGT | CTC<br>GAG | AAG<br>TCC | TAC<br>ATG | ACT<br>TGA | GAC<br>CTG | CCC<br>GGG | ATT<br>TAA | ACT<br>TGA |
| ACC<br>TGG | AAT<br>TTA | GCT<br>CGA | AAG<br>TTC | CAT<br>GTA | GAG<br>CTC | CTT<br>GAA | ACT<br>TGA | TTA<br>AAT | AAA<br>TTT | CTT<br>GAA | GGA<br>CCT | AGC<br>TCG | AAC<br>TTG | ATA<br>TAT | ACT<br>TGA |
| TTA<br>AAT | GAA<br>CTT | AAT<br>TTA | GGG<br>CCC | TTA<br>AAT | CTT<br>GAA | TCG<br>AGC | GCC<br>CGG | ACA<br>TGT | GTT<br>CAA | CCC<br>GGG | ACT<br>TGA | GTT<br>CAA | TCT<br>AGA | CCT<br>GGA | CCC<br>GGG |
| CTT<br>GAA | ACA<br>TGT | AAC<br>TTG | AGT<br>TCA | AAC<br>TTG | AAC<br>TTG | TCC<br>AGG | CTG<br>GAC | GGT<br>CCA | TTA<br>AAT | GCC<br>CGG | ACA<br>TGT | TCC<br>AGG | GCT<br>CGA | CCC<br>GGG | ATA<br>TAT |
| GCT<br>CGA | GTA<br>CAT | TCA<br>AGT | GCT<br>CGA | AAC<br>TTG | TCT<br>AGA | CTC<br>GAG | ACA<br>TGT | TTG<br>AAC | GCC<br>CGG | ACC<br>TGG | GCC<br>CGG | GCA<br>CGT | CCA<br>GGT | CTG<br>GAC | ACA<br>TGT |
| GTA<br>CAT | AGC<br>TCG | AAC<br>TTG | AAC<br>TTG | CAG<br>GTC | CTT<br>GAA | AGT<br>TCA | ATT<br>TAA | AAC<br>TTG | GCG<br>CGC | GGC<br>CCG | AGA<br>TCT | GGT<br>CCA | TTA<br>AAT | GTT<br>CAA | ATA<br>TAT |
| ACT<br>TGA | AAC<br>TTG | AAT<br>TTA | GCC<br>CGG | TTA<br>AAT | ACA<br>TGT | GTT<br>CAA | AAT<br>TTA | CCT<br>GGA | ACC<br>TGG | GGA<br>CCT | GCG<br>CGC | CTA<br>GAT | GGT<br>CCA | TTC<br>AAG | AAT<br>TTA |
| AAC<br>TTG | ACA<br>TGT | GGA<br>CCT | GCT<br>CGA | TTA<br>AAT | CAA<br>GTT | TTA<br>AAT | AAT<br>TTA | GCT<br>CGA | GCA<br>CGT | GGA<br>CCT | GGA<br>CCT | ATG<br>TAC | AGA<br>TCT | GTG<br>CAC | GAC<br>CTG |
| GGT<br>CCA | GCC<br>CGG | AAC<br>TTG | TTA<br>AAT | ATT<br>TAA | CTT<br>GAA | CAT<br>GTA | GTA<br>CAT | GCA<br>CGT | TAT<br>ATA | CCC<br>GGG | TTT<br>AAA | GAA<br>CTT | GCA<br>CGT | ATC<br>TAG | AAC<br>TTG |
| CAG<br>GTC | CTA<br>GAT | ACA<br>TGT | CTG<br>GAC | CGA<br>GCT | TTA<br>AAT | GAA<br>CTT | AAC<br>TTG | GGG<br>CCC | TTA<br>AAT | GAA<br>CTT | GTA<br>CAT | ACC<br>TGG | AGC<br>TCG | GGA<br>CCT | GGA<br>CCT |
| AAG<br>TTC | CTT<br>GAA | AAC<br>TTG | GTT<br>CAA | AAG<br>TTC | TTG<br>AAC | GGA<br>CCT | TCA<br>AGT | GGC<br>CCG | CTC<br>GAG | CAA<br>GTT | TTT<br>AAA | GAC<br>CTG | AGT<br>TCA | AAC<br>TTG | GGA<br>CCT |
| CGC<br>GCG | ATT<br>TAA | GCT<br>CGA | ATT<br>TAA | AGT<br>TCA | AAT<br>TTA | AGC<br>TCG | AAC<br>TTG | CGA<br>GCT | ACT<br>TGA | CGA<br>GCT | AGT<br>TCA | GTA<br>CAT | CCA<br>GGT | TCC<br>AGG | CTC<br>GAG |
| ACT<br>TGA | ACC<br>TGG | ATT<br>TAA | TGG<br>ACC | TCT<br>AGA | ATC<br>TAG | TCG<br>AGC | CCT<br>GGA | ACG<br>TGC | CCT<br>GGA | AAC<br>TTG | TGC<br>ACG | TCC<br>AGG | ATT<br>TAA | TAT<br>ATA | GAA<br>CTT |
| ACC<br>TGG | CAA<br>GTT | GAT<br>CTA | GCA<br>CGT | AAC<br>TTG | CTA<br>GAT | TTT<br>AAA | CTT<br>GAA | TGT<br>ACA | CTA<br>GAT | ACT<br>TGA | AAA<br>TTT | AAC<br>TTG | GGA<br>CCT | GCT<br>CGA | CAC<br>GTG |
| GTA<br>CAT | TTA<br>AAT | GGT<br>CCA | ACT<br>TGA | ATA<br>TAT | ACA<br>TGT | ATC<br>TAG | AAA<br>TTT | GGT<br>CCA | CTT<br>GAA | AAA<br>TTT | GGA<br>CCT | GCA<br>CGT | CTG<br>GAC | CGG<br>GCC | GAA<br>CTT |
| ATG<br>TAC | CAC<br>GTG | GAT<br>CTA | AAC<br>TTG | GCT<br>CGA | CTA<br>GAT | TCT<br>AGA | TTA<br>AAT | AAA<br>TTT | CTT<br>GAA | CCC<br>GGG | TTT<br>AAA | GAC<br>CTG | AAT<br>TTA | CAG<br>GTC | GGA<br>CCT |
| AAT<br>TTA | TTA<br>AAT | CTT<br>GAA | AAC<br>TTG | TGT<br>ACA | GCC<br>CGG | TTG<br>AAC | GAA<br>CTT | TCA<br>AGT | TCC<br>AGG | ACC<br>TGG | TGG<br>ACC | CGT<br>GCA | TAC<br>ATG | CAG<br>GTC | GAA<br>CTT |
| ACC<br>TGG | AAC<br>TTG | GCA<br>CGT | GTG<br>CAC | GCC<br>CGG | TCT<br>AGA | AAT<br>TTA | GCC<br>CGG | TTA<br>AAT | ACA<br>TGT | TTT<br>AAA | ATG<br>TAC | CCC<br>GGG | AAC<br>TTG | AGT<br>TCA | ACA<br>TGT |
| GTG<br>CAC | TAT<br>ATA | CCA<br>GGT | CGA<br>GCT | AAC<br>TTG | AAA<br>TTT | ACC<br>TGG | GCT<br>CGA | CAC<br>GTG | CCG<br>GGC | GGC<br>CCG | AAC<br>TTG | ATG<br>TAC | CTC<br>GAG | ATC<br>TAG | CAA<br>GTT |
| ATC<br>TAG | TCG<br>AGC | CCT<br>GGA | AAC<br>TTG | ATC<br>TAG | ACC<br>TGG | TTC<br>AAG | AGT<br>TCA | GTC<br>CAG | GTC<br>CAG | TAC<br>ATG | AAC<br>TTG | GAG<br>CTC | ATA<br>TAT | AAC<br>TTG | AGT<br>TCA |
| GGG<br>CCC | TAT<br>ATA | GCT<br>CGA | TTT<br>AAA | ACT<br>TGA | TTT<br>AAA | AAA<br>TTT | TGG<br>ACC | TCA<br>AGT | GCC<br>CGG | GAA<br>CTT | CCG<br>GGC | GGA<br>CCT | AAA<br>TTT | CCT<br>GGA | TTT<br>AAA |
| CAC<br>GTG | CCA<br>GGT | CCT<br>GGA | ACC<br>TGG | GCT<br>CGA | GTA<br>CAT | TTT<br>AAA | TGC<br>ACG | TAC<br>ATG | ATA<br>TAT | ACT<br>TGA | GAA<br>CTT | CAA<br>GTT | TAA<br>ATT | | |

10. The nucleic acid according to claim 6 having a nucleotide sequence encoding an amino acid sequence for Ad41 short fiber protein which comprises:

Met Lys Arg Thr Arg Ile Glu Asp Asp Phe Asn Pro Val Tyr Pro Tyr Asp Thr Phe

-continued

| | | | | | | | | | | | | | | | | | | |
|---|---|---|---|---|---|---|---|---|---|---|---|---|---|---|---|---|---|---|
| Ser | Thr | Pro | Ser | Ile | Pro | Tyr | Val | Ala | Pro | Pro | Phe | Val | Ser | Ser | Asp | Gly | Leu | Gln |
| Glu | Lys | Pro | Pro | Gly | Val | Leu | Ala | Leu | Lys | Tyr | Thr | Asp | Pro | Ile | Thr | Thr | Asn | Ala |
| Lys | His | Glu | Leu | Thr | Leu | Lys | Leu | Gly | Ser | Asn | Ile | Thr | Leu | Glu | Asn | Gly | Leu | Leu |
| Ser | Ala | Thr | Val | Pro | Thr | Val | Ser | Pro | Pro | Leu | Thr | Asn | Ser | Asn | Asn | Ser | Leu | Gly |
| Leu | Ala | Thr | Ser | Ala | Pro | Ile | Ala | Val | Ser | Ala | Asn | Ser | Leu | Thr | Leu | Ala | Thr | Ala |
| Ala | Pro | Leu | Thr | Val | Ser | Asn | Asn | Gln | Leu | Ser | Ile | Asn | Ala | Gly | Arg | Gly | Leu | Val |
| Ile | Thr | Asn | Asn | Ala | Leu | Thr | Val | Asn | Pro | Thr | Gly | Ala | Leu | Gly | Phe | Asn | Asn | Thr |
| Gly | Ala | Leu | Gln | Leu | Asn | Ala | Ala | Gly | Gly | Met | Arg | Val | Asp | Gly | Ala | Asn | Leu | Ile |
| Leu | His | Val | Ala | Tyr | Pro | Phe | Glu | Ala | Ile | Asn | Gln | Leu | Thr | Leu | Arg | Leu | Glu | Asn |
| Gly | Leu | Glu | Val | Thr | Ser | Gly | Gly | Lys | Leu | Asn | Val | Lys | Leu | Gly | Ser | Gly | Leu | Gln |
| Phe | Asp | Ser | Asn | Gly | Arg | Ile | Ala | Ile | Ser | Asn | Ser | Asn | Arg | Thr | Arg | Ser | Val | Pro |
| Ser | Leu | Thr | Thr | Ile | Trp | Ser | Ile | Ser | Pro | Thr | Pro | Asn | Cys | Ser | Ile | Tyr | Glu | Thr |
| Gln | Asp | Ala | Asn | Leu | Phe | Leu | Cys | Leu | Thr | Lys | Asn | Gly | Ala | His | Val | Leu | Gly | Thr |
| Ile | Thr | Ile | Lys | Gly | Leu | Lys | Gly | Ala | Leu | Arg | Glu | Met | His | Asp | Asn | Ala | Leu | Ser |
| Leu | Lys | Leu | Pro | Phe | Asp | Asn | Gln | Gly | Asn | Leu | Leu | Asn | Cys | Ala | Leu | Glu | Ser | Ser |
| Thr | Trp | Arg | Tyr | Gln | Glu | Thr | Asn | Ala | Val | Ala | Ser | Asn | Ala | Leu | Thr | Phe | Met | Pro |
| Asn | Ser | Thr | Val | Tyr | Pro | Arg | Asn | Lys | Thr | Ala | His | Pro | Gly | Asn | Met | Leu | Ile | Gln |
| Ile | Ser | Pro | Asn | Ile | Thr | Phe | Ser | Val | Val | Tyr | Asn | Glu | Ile | Asn | Ser | Gly | Tyr | Ala |
| Phe | Thr | Phe | Lys | Trp | Ser | Ala | Glu | Pro | Gly | Lys | Pro | Phe | His | Pro | Pro | Thr | Ala | Val |
| Phe | Cys | Tyr | Ile | Thr | Glu | Gln | | | | | | | | | | | | |

11. An isolated nucleic acid having a sequence encoding an E3 RL-1 protein of human adenovirus Type 41.

12. An isolated nucleic acid having a sequence encoding an E3 RL-2 protein of human adenovirus Type 41.

13. An isolated nucleic acid having a sequence encoding an E3 RL-3 protein of human adenovirus Type 41.

14. An isolated nucleic acid having a sequence encoding an E3 RL-4 protein of human adenovirus Type 41.

15. An isolated nucleic acid having a sequence encoding an E3 RL-5 protein of human adenovirus Type 41.

16. An isolated nucleic acid having a sequence encoding an E3 RL-6 protein of human adenovirus Type 41.

17. The nucleic acid of any one of claims 11-16 wherein said nucleic acid is DNA, cDNA, recombinant DNA or RNA.

18. An isolated nucleic acid having a sequence encoding the E3 region of human adenovirus Type 41 having a nucleotide sequence which comprises:

```
        20         30         40         50         60
   *    *     *    *     *    *     *    *     *    *     *    *
GAATTCGCGC CACTCGAAAC CAAATTTTGC TGGAGCAAGC TGCCCTGACC TCCACCCCGC
CTTAAGCGCG GTGAGCTTTG GTTTAAAACG ACCTCGTTCG ACGGGACTGG AGGTGGGGCG

        80         90        100        110        120
   *    *     *    *     *    *     *    *     *    *     *    *
GAAGTCAATT GAACCCGCCC AATTGGCCCG CTGCCCAGGT GTATCAGGAA AACCCCGCTC
CTTCAGTTAA CTTGGGCGGG TTAACCGGGC GACGGGTCCA CATAGTCCTT TTGGGGCGAG

       140        150        160        170        180
   *    *     *    *     *    *     *    *     *    *     *    *
CGACCACAGT TCTCCTGCCA CGCGACGCTG AGGCCGAAGT CCAAATGACT AACTCCGGAG
GCTGGTGTCA AGAGGACGGT GCGCTGCGAC TCCGGCTTCA GGTTTACTGA TTGAGGCCTC

       200        210        220        230        240
   *    *     *    *     *    *     *    *     *    *     *    *
CGCAATTAGC GGGCGGATCC AGACACGTCA GGTTCAGAGG TCGGTCCTCG CCCTACTCTC
GCGTTAATCG CCCGCCTAGG TCTGTGCAGT CCAAGTCTCC AGCCAGGAGC GGGATGAGAG

       260        270        280        290        300
   *    *     *    *     *    *     *    *     *    *     *    *
CAGGTCCTAT AAAGAGGCTG ATTATCCGAG GCCGGGGTAT CCAGCTCAAC GACGAAGTGG
GTCCAGGATA TTTCTCCGAC TAATAGGCTC CGGCCCCATA GGTCGAGTTG CTGCTTCACC

       320        330        340        350        360
   *    *     *    *     *    *     *    *     *    *     *    *
TGAGCTCCTT AACCGGTCTC CGACCTGACG GAGTTTTCCA GCTTGGAGGT GCCGGCCGCT
ACTCGAGGAA TTGGCCAGAG GCTGGACTGC CTCAAAAGGT CGAACCTCCA CGGCCGGCGA

       380        390        400        410        420
   *    *     *    *     *    *     *    *     *    *     *    *
CCTCCTTCAC TCCTCGCCAG GCGTACCTGA CACTCCAGAG CTCTTCTTCC CAGCCTCGCT
GGAGGAAGTG AGGAGCGGTC CGCATGGACT GTGAGGTCTC GAGAAGAAGG GTCGGAGCGA

       440        450        460        470        480
   *    *     *    *     *    *     *    *     *    *     *    *
CCGGCGGCAT TGGAACCCTC CAGTTTGTGG AGGAGTTTGT ACCCTCCGTT TACTTCAACC
GGCCGCCGTA ACCTTGGGAG GTCAAACACC TCCTCAAACA TGGGAGGCAA ATGAAGTTGG

       500        510        520        530        540
   *    *     *    *     *    *     *    *     *    *     *    *
CATTCTCGGG CGCTCCTGGT CTTTACCCAG ACGACTTCAT CCCAAACTAC GACGCGGTGA
GTAAGAGCCC GCGAGGACCA GAAATGGGTC TGCTGAAGTA GGGTTTGATG CTGCGCCACT

       560        570        580        590        600
   *    *     *    *     *    *     *    *     *    *     *    *
```

-continued

```
GCGAATCTGT GGACGGCTAC GACTGAATCC CAATGGTGCG TCCGTGACTG TGTGGCTGCA
CGCTTAGACA CCTGCCGATG CTGACTTAGG GTTACCACGC AGGCACTGAC ACACCGACGT

       620        630        640        650        660
ACATCTACAT CGGCGCCGTA ATCCTTGCTA CTTTGTCTGA AAAGTCTGTG ATTTTTACTT
TGTAGATGTA GCCGCGGCAT TAGGAACGAT GAAACAGACT TTTCAGACAC TAAAAATGAA

       680        690        700        710        720
ACCGCTCCAG CGCTTGGATT ACATGAAGAT CTGTGTTCTT TTTTGTGTGC TAAGTTTAAC
TGGCGAGGTC GCGAACCTAA TGTACTTCTA GACACAAGAA AAAACACACG ATTCAAATTG

       740        750        760        770        780
AAGTAGCCTA AGGACTTCAC CTACAACCGT TGGTTCCTTA CGTCAGCTAC AAGATTCCAC
TTCATCGGAT TCCTGAAGTG GATGTTGGCA ACCAAGGAAT GCAGTCGATG TTCTAAGGTG

       800        810        820        830        840
CAAAGGTACA CACCAAACTC TTTATTTTTC TGAGTCTACC ACTTCTATTG CACTTAACTG
GTTTCCATGT GTGGTTTGAG AAATAAAAAG ACTCAGATGG TGAAGATAAC GTGAATTGAC

       850        860        870        880        890        900
TTCTTGTCGT AACCAACTCG TTCAGTGGCG CGCTAACAGA CAATTTTGCA AACTATTTTG
AAGAACAGCA TTGGTTGAGC AAGTCACCGC GCGATTGTCT GTTAAAACGT TTGATAAAAC

       910        920        930        940        950        960
GGACGCTCTT ATTGTTCAAG GAAACAACAG CCTTTGTAAC AACTGTACTG CTACTACTTT
CCTGCGAGAA TAACAAGTTC CTTTGTTGTC GGAAACATTG TTGACATGAC GATGATGAAA

       970        980        990       1000       1010       1020
AACTCTTACA CCTCCTTTTG TTCCCGGTCC ATACTTGTGC ATTGGCACAG GAAGAGGGCC
TTGAGAATGT GGAGGAAAAC AAGGGCCAGG TATGAACACG TAACCGTGTC CTTCTCCCGG

      1030       1040       1050       1060       1070       1080
TAGCTGCTTT AATCGCTGGA CTTTACAAAA AGAGAACCTA ACCACTACCA CCCTCCTTCC
ATCGACGAAA TTAGCGACCT GAAATGTTTT TCTCTTGGAT TGGTGATGGT GGGAGGAAGG

      1090       1100       1110       1120       1130       1140
CCTTACTACT TATACTTTTT CCCAAAAAAA AATTTACTTT TTGCCCATTA TTGCACTTTT
GGAATGATGA ATATGAAAAA GGGTTTTTTT TTAAATGAAA AACGGGTAAT AACGTGAAAA

      1150       1160       1170       1180       1190       1200
GGCCTTTGTC TGTGTTATTA CCGCTAATTA CATTTTAATT TTCAATCTTG ATAATTTTTA
CCGGAAACAG ACACAATAAT GGCGATTAAT GTAAAATTAA AAGTTAGAAC TATTAAAAAT

      1210       1220       1230       1240       1250       1260
CTAATCATGC TGCTGTTTTT ACTTTGCCTT CTTTTCTGCT CTGCCTATGC CGCCGTGCCA
GATTAGTACG ACGACAAAAA TGAAACGGAA GAAAAGACGA GACGGATACG GCGGCACGGT

      1270       1280       1290       1300       1310       1320
GAAAAAACTC TTAACAACCT CGTTCGGGTG TATGCCTTAG TTGGTACCAA TCTATCCCTT
CTTTTTTGAG AATTGTTGGA GCAAGCCCAC ATACGGAATC AACCATGGTT AGATAGGGAA

      1330       1340       1350       1360       1370       1380
GATTCTATGA AAACTCCTCA GATTGACGAA CTTACTAGTC TTAGCTGGAT TAAACAGGAA
CTAAGATACT TTTGAGGAGT CTAACTGCTT GAATGATCAG AATCGACCTA ATTTGTCCTT

      1390       1400       1410       1420       1430       1440
GACAATCCTA ACAAAAACTT ACAATCATTT TTTTTTATTG GTCAAAAACT CTGTGAAGTT
CTGTTAGGAT TGTTTTTGAA TGTTAGTAAA AAAAAATAAC CAGTTTTTGA GACACTTCAA

      1450       1460       1470       1480       1490       1500
ACCAAAGACA AAATCACTGT TTTTAACTAT TATCCGTTGG AATTTTCCTG CGCTAACGTA
TGGTTTCTGT TTTAGTGACA AAAATTGATA ATAGGCAACC TTAAAAGGAC GCGATTGCAT

      1510       1520       1530       1540       1550       1560
ACCTTGTATT TGTATAATCT TAAAACTGAC GATTCTGGCC TCTATAATGG AAAGGCCCAT
TGGAACATAA ACATATTAGA ATTTTGACTG CTAAGACCGG AGATATTACC TTTCCGGGTA
```

-continued

| 1570 | 1580 | 1590 | 1600 | 1610 | 1620 |
|---|---|---|---|---|---|
| ACCAAAGAGC | TTGAACATAA | CACCTATGTT | AGGCTTTATG | TTATTGACAT | TCCTCCGCCT |
| TGGTTTCTCG | AACTTGTATT | GTGGATACAA | TCCGAAATAC | AATAACTGTA | AGGAGGCGGA |
| 1630 | 1640 | 1650 | 1660 | 1670 | 1680 |
| AAGTGTGACA | TTACTTCACG | TTACTTAGGC | ATACAGGCTA | CTGGGGAAGA | TTATTGTTTA |
| TTCACACTGT | AATGAAGTGC | AATGAATCCG | TATGTCCGAT | GACCCCTTCT | AATAACAAAT |
| 1690 | 1700 | 1710 | 1720 | 1730 | 1740 |
| ATTGAAATCA | ATTGCACTAA | CTCCAAATAC | CCAGCTGTGG | TTAAATTTAA | TGGCAGGCAA |
| TAACTTTAGT | TAACGTGATT | GAGGTTTATG | GGTCGACACC | AATTTAAATT | ACCGTCCGTT |
| 1750 | 1760 | 1770 | 1780 | 1790 | 1800 |
| AGCAACTTCT | ACCATTATGT | TAGCGAAAAC | GGAAACAAAG | AACTTCCAAA | TTTTTATGAA |
| TCGTTGAAGA | TGGTAATACA | ATCGCTTTTG | CCTTTGTTTC | TTGAAGGTTT | AAAAATACTT |
| 1810 | 1820 | 1830 | 1840 | 1850 | 1860 |
| ACACACATCA | CTGTTAATGG | TACCCACAAA | AGCTTTCACT | TTAATTACCC | TTTTAACGAC |
| TGTGTGTAGT | GACAATTACC | ATGGGTGTTT | TCGAAAGTGA | AATTAATGGG | AAAATTGCTG |
| 1870 | 1880 | 1890 | 1900 | 1910 | 1920 |
| CTTTGTCAAA | CAACCAGCGC | TCTACAATAT | AATGACAATG | TCCAGGTAGT | CCTCATTCTT |
| GAAACAGTTT | GTTGGTCGCG | AGATGTTATA | TTACTGTTAC | AGGTCCATCA | GGAGTAAGAA |
| 1930 | 1940 | 1950 | 1960 | 1970 | 1980 |
| CTCATAGTAG | TTGGCTTAAT | AATAATTTCC | GCTAGTTTAA | TATTGCTTTA | TTGCCACCGC |
| GAGTATCATC | AACCGAATTA | TTATTAAAGG | CGATCAAATT | ATAACGAAAT | AACGGTGGCG |
| 2000 | 2010 | 2020 | 2030 | 2040 | |
| AAAAAAATCA | AGGCCGAAGT | TCAACATCAA | CCAGTGCATA | TTTGTTTAGA | AAAATAAAAT |
| TTTTTTTAGT | TCCGGCTTCA | AGTTGTAGTT | GGTCACGTAT | AAACAAATCT | TTTTATTTTA |
| 2060 | 2070 | 2080 | 2090 | 2100 | |
| TTTTTTCTTT | TCAGTATGGT | AACTCCTCTT | CTCCTGCTTG | TCTGTCTGCC | AATTATCTAC |
| AAAAAAGAAA | AGTCATACCA | TTGAGGAGAA | GAGGACGAAC | AGACAGACGG | TTAATAGATG |
| 2120 | 2130 | 2140 | 2150 | 2160 | |
| GCCTCCACCA | CCTTCGCCGC | AGTCTCCCAC | CTTGATACGG | ATTGTCTTCC | CGCCTTGCTG |
| CGGAGGTGGT | GGAAGCGGCG | TCAGAGGGTG | GAACTATGCC | TAACAGAAGG | GCGGAACGAC |
| 2180 | 2190 | 2200 | 2210 | 2220 | |
| ACTTATCTCA | TCTTCACCTC | TGTTTGCTGC | ACTGCCATCT | GCAGCATTGC | CACTTTTTTT |
| TGAATAGAGT | AGAAGTGGAG | ACAAACGACG | TGACGGTAGA | CGTCGTAACG | GTGAAAAAAA |
| 2240 | 2250 | 2260 | 2270 | 2280 | |
| GTGGCCATTT | TCCAAACTGC | GGACTACCTA | TACGTTAGAG | TGGCATACTA | TCGTCATCAT |
| CACCGGTAAA | AGGTTTGACG | CCTGATGGAT | ATGCAATCTC | ACCGTATGAT | AGCAGTAGTA |
| 2300 | 2310 | 2320 | 2330 | 2340 | |
| CCCCAATATA | GGAACCACGA | GGTGGCCGCC | CTTCTGTGCC | TGTCATGAAA | GTTCCTCTTC |
| GGGGTTATAT | CCTTGGTGCT | CCACCGGCGG | GAAGACACGG | ACAGTACTTT | CAAGGAGAAG |
| 2360 | 2370 | 2380 | 2390 | 2400 | |
| TCTGTCTTAT | CCTCCTTCAC | AAAGTCCTGG | CCAACTGCCA | CCTCCACCGG | CCCACCGAGT |
| AGACAGAATA | GGAGGAAGTG | TTTCAGGACC | GGTTGACGGT | GGAGGTGGCC | GGGTGGCTCA |
| 2420 | 2430 | 2440 | 2450 | 2460 | |
| TCCTGCGCTG | CTACTCAACA | GAAACCTCTT | CCTTTTGGCT | GTACTCCATT | ATTTTTATTT |
| AGGACGCGAC | GATGAGTTGT | CTTTGGAGAA | GGAAAACCGA | CATGAGGTAA | TAAAAATAAA |
| 2480 | 2490 | 2500 | 2510 | 2520 | |
| TGATTTTCTT | TGCCACCTTT | TTGGGATTAC | AAATTTACGG | CTGCCTTCAC | CTGGGCTGGA |
| ACTAAAAGAA | ACGGTGGAAA | AACCCTAATG | TTTAAATGCC | GACGGAAGTG | GACCCGACCT |
| 2540 | 2550 | 2560 | 2570 | 2580 | |
| TGCATCCTCC | CAACAACCTA | CCCAGATTTC | CTGGTTTCTT | ATTACAGCCC | CCGCCGCCCC |

-continued

```
ACGTAGGAGG GTTGTTGGAT GGGTCTAAAG GACCAAAGAA TAATGTCGGG GGCGGCGGGG

      2600       2610       2620       2630       2640
    *    *     *    *     *    *     *    *     *    *     *    *
CACCAGCTCC TGTACAGCGC GCTCCATCAG TTATTAGCTA CTTTCATCTT AACTCTGAAG
GTGGTCGAGG ACATGTCGCG CGAGGTAGTC AATAATCGAT GAAAGTAGAA TTGAGACTTC

      2660       2670       2680       2690       2700
    *    *     *    *     *    *     *    *     *    *     *    *
ATGTCTGACC AACTAGAAAT CGACGGGCAG CGCACTGAGC AGCTGATCCT TGCTCGGCGA
TACAGACTGG TTGATCTTTA GCTGCCCGTC GCGTGACTCG TCGACTAGGA ACGAGCCGCT

      2720       2730       2740       2750       2760
    *    *     *    *     *    *     *    *     *    *     *    *
AAACTCAAAC AACAAAACCA GGAATTGTTC AACCTTCAAG CCTTACACCA ATGCAAAAAG
TTTGAGTTTG TTGTTTTGGT CCTTAACAAG TTGGAAGTTC GGAATGTGGT TACGTTTTTC

      2780       2790       2800       2810       2820
    *    *     *    *     *    *     *    *     *    *     *    *
GGTCTTTTCT GCCTGGTTAA ACAAGCTGAA CTTTGCTATG ATGTAACCCA ACAGGGGCAT
CCAGAAAAGA CGGACCAATT TGTTCGACTT GAAACGATAC TACATTGGGT TGTCCCCGTA

      2840       2850       2860       2870       2880
    *    *     *    *     *    *     *    *     *    *     *    *
GAGCTATCAT ACACTTTAAA CAAGCAAAGA CAGAGCTTTA TGACTATGGT GGGGGTTAAG
CTCGATAGTA TGTGAAATTT GTTCGTTTCT GTCTCGAAAT ACTGATACCA CCCCCAATTC

      2900       2910       2920       2930       2940
    *    *     *    *     *    *     *    *     *    *     *    *
CCCATTAAGG TTACTCAGCA ATCCGGCCCA GTTGAGGGAA GCATTCTTTG TCAGTGCACC
GGGTAATTCC AATGAGTCGT TAGGCCGGGT CAACTCCCTT CGTAAGAAAC AGTCACGTGG

      2960       2970       2980       2990       3000
    *    *     *    *     *    *     *    *     *    *     *    *
AATTCTGAAT GCATGTACAC TATGGTAAAA ACCCTGTGTG GTCTCAGGGA ACTTCTCCCC
TTAAGACTTA CGTACATGTG ATACCATTTT TGGGACACAC CAGAGTCCCT TGAAGAGGGG

      3020       3030       3040       3050       3060
    *    *     *    *     *    *     *    *     *    *     *    *
TTTAATTAAA GTTATCTGAT TAATAAAGCT TACCTTAAAT TTGATATCAG TTGTTTGTCA
AAATTAATTT CAATAGACTA ATTATTTCGA ATGGAATTTA AACTATAGTC AACAAACAGT

      3080       3090       3100       3110       3120
    *    *     *    *     *    *     *    *     *    *     *    *
AGTTTTTCCA GCAGCACCAC CTGCCCTTCC TCCCAACTTT CGTAGGGGAT GTGCCAACGG
TCAAAAAGGT CGTCGTGGTG GACGGGAAGG AGGGTTGAAA GCATCCCCTA CACGGTTGCC

      3140       3150       3160       3170       3180
    *    *     *    *     *    *     *    *     *    *     *    *
GCAGCAAACT TTCTCCACGT CCTAAAGGGT ATATCGGTGT TCACCTTTTT ACCCTGACCC
CGTCGTTTGA AAGAGGTGCA GGATTTCCCA TATAGCCACA AGTGGAAAAA TGGGACTGGG

      3190       3200       3210       3220       3230       3240
    *    *     *    *     *    *     *    *     *    *     *    *
ACGATCTTCA TCTTGCAGAT GAAAAGAACC AGAATTGAAG ACGACTTCAA CCCCGTCTAC
TGCTAGAAGT AGAACGTCTA CTTTTCTTGG TCTTAACTTC TGCTGAAGTT GGGGCAGATG

      3250       3260       3270       3280       3290       3300
    *    *     *    *     *    *     *    *     *    *     *    *
CCCTATGACA CCTTCTCAAC TCCCAGCATC CCCTATGTAG CTCCGCCCTT CGTTTCTTCT
GGGATACTGT GGAAGAGTTG AGGGTCGTAG GGGATACATC GAGGCGGGAA GCAAAGAAGA

      3310       3320       3330       3340       3350       3360
    *    *     *    *     *    *     *    *     *    *     *    *
GACGGGTTAC AGGAAAAACC CCCAGGAGTT TTAGCACTCA AGTACACTGA CCCCATTACT
CTGCCCAATG TCCTTTTTGG GGGTCCTCAA AATCGTGAGT TCATGTGACT GGGGTAATGA

      3370
    *    *
ACCAATGCTA AGC
TGGTTACGAT TCG
```

19. The nucleic acid according to claim 11 having a nucleotide sequence of FIG. 4 from base 683 to base 1204.

20. The nucleic acid according to claim 19 encoding an amino acid sequence for RL-1 which comprises:

| | | | | | | | | | | | | | | | | |
|---|---|---|---|---|---|---|---|---|---|---|---|---|---|---|---|---|
| Met | Lys | Ile | Cys | Val | Leu | Phe | Cys | Val | Leu | Ser | Leu | Thr | Ser | Ser | Leu | Arg |
| Thr | Ser | Pro | Thr | Thr | Val | Gly | Ser | Leu | Arg | Gln | Leu | Gln | Asp | Ser | Thr | Lys |
| Gly | Thr | His | Gln | Thr | Leu | Tyr | Phe | Ser | Glu | Ser | Thr | Thr | Ser | Ile | Ala | Leu |
| Asn | Cys | Ser | Cys | Arg | Asn | Gln | Leu | Val | Gln | Trp | Arg | Ala | Asn | Arg | Gln | Phe |
| Cys | Lys | Leu | Phe | Trp | Asp | Ala | Leu | Ile | Val | Gln | Gly | Asn | Asn | Ser | Leu | Cys |

-continued

Asn Asn Cys Thr Ala Thr Thr Leu Thr Leu Thr Pro Pro Phe Val Pro Gly
Pro Tyr Leu Cys Ile Gly Thr Gly Arg Gly Pro Ser Cys Phe Asn Arg Trp
Thr Leu Gln Lys Glu Asn Leu Thr Thr Thr Thr Leu Leu Pro Leu Thr Thr
Tyr Thr Phe Ser Gln Lys Lys Ile Tyr Phe Leu Pro Ile Ile Ala Leu Leu
Ala Phe Val Cys Val Ile Thr Ala Asn Tyr Ile Leu Ile Phe Asn Leu Asp
Asn Phe Tyr

21. The nucleic acid according to claim 12 having a nucleotide sequence of FIG. 4 from base 1207 to base 2037.

22. The nucleic acid according to claim 21 encoding an amino acid sequence for RL-2 which comprises:

Met Leu Leu Phe Leu Leu Cys Leu Leu Phe Cys Ser Ala Tyr Ala Ala Val
Pro Glu Lys Thr Leu Asn Asn Leu Val Arg Val Tyr Ala Leu Val Gly Thr
Asn Leu Ser Leu Asp Ser Met Lys Thr Pro Gln Ile Asp Glu Leu Thr Ser
Leu Ser Trp Ile Lys Gln Glu Asp Asn Pro Asn Lys Asn Leu Gln Ser Phe
Phe Phe Ile Gly Gln Lys Leu Cys Glu Val Thr Lys Asp Lys Ile Thr Val
Phe Asn Tyr Tyr Pro Leu Glu Phe Ser Cys Ala Asn Val Thr Leu Tyr Leu
Tyr Asn Leu Lys Thr Asp Asp Ser Gly Leu Tyr Asn Gly Lys Ala His Thr
Lys Glu Leu Glu His Asn Thr Tyr Val Arg Leu Tyr Val Ile Asp Ile Pro
Pro Pro Lys Cys Asp Ile Thr Ser Arg Tyr Leu Gly Ile Gln Ala Thr Gly
Glu Asp Tyr Cys Leu Ile Glu Ile Asn Cys Thr Asn Ser Lys Tyr Pro Ala
Val Val Lys Phe Asn Gly Arg Gln Ser Asn Phe Tyr His Tyr Val Ser Glu
Asn Gly Asn Lys Glu Leu Pro Asn Phe Tyr Glu Thr His Ile Thr Val Asn
Gly Thr His Lys Ser Phe His Phe Asn Tyr Pro Phe Asn Asp Leu Cys Gln
Thr Thr Ser Ala Leu Gln Tyr Asn Asp Asn Val Gln Val Val Leu Ile Leu
Leu Ile Val Val Gly Leu Ile Ile Ile Ser Ala Ser Leu Ile Leu Leu Tyr
Cys His Arg Lys Lys Ile Lys Ala Glu Val Gln His Gln Pro Val His Ile
Cys Leu Glu Lys

23. The nucleic acid according to claim 13 having a nucleotide sequence of FIG. 4 from base 1730 to base 1909.

24. The nucleic acid according to claim 23 encoding an amino acid sequence for RL-3 which comprises:

Met Ala Gly Lys Ala Thr Ser Thr Ile Met Leu Ala Lys Thr Glu Thr Lys
Asn Phe Gln Ile Phe Met Lys His Thr Ser Leu Leu Met Val Pro Thr Lys
Ala Phe Thr Leu Ile Thr Leu Leu Thr Thr Phe Val Lys Gln Pro Ala Leu
Tyr Asn Ile Met Thr Met Ser Arg

25. The nucleic acid according to claim 14 having a nucleotide sequence of FIG. 4 from base 2056 to base 2328.

26. The nucleic acid according to claim 25 encoding an amino acid sequence for RL-4 which comprises:

Met Val Thr Pro Leu Leu Leu Leu Val Cys Leu Pro Ile Ile Tyr Ala Ser
Thr Thr Phe Ala Ala Val Ser His Leu Asp Thr Asp Cys Leu Pro Ala Leu
Leu Thr Tyr Leu Ile Phe Thr Ser Val Cys Cys Thr Ala Ile Cys Ser Ile
Ala Thr Phe Phe Val Ala Ile Phe Gln Thr Ala Asp Tyr Leu Tyr Val Arg
Val Ala Tyr Tyr Arg His His Pro Gln Tyr Arg Asn His Glu Val Ala Ala
Leu Leu Cys Leu Ser

27. The nucleic acid according to claim 15 having a nucleotide sequence of FIG. 4 from base 2325 to base 2648.

28. The nucleic acid according to claim 27 encoding an amino acid sequence for RL-5 which comprises:

Met Lys Val Pro Leu Leu Cys Leu Ile Leu Leu His Lys Val Leu Ala Asn
Cys His Leu His Arg Pro Thr Glu Phe Leu Arg Cys Tyr Ser Thr Glu Thr
Ser Ser Phe Trp Leu Tyr Ser Ile Ile Phe Ile Leu Ile Phe Phe Ala Thr
Phe Leu Gly Leu Gln Ile Tyr Gly Cys Leu His Leu Gly Trp Met His Pro
Pro Asn Asn Leu Pro Arg Phe Pro Gly Phe Leu Leu Gln Pro Pro Pro Pro
Pro Pro Ala Pro Val Gln Arg Ala Pro Ser Val Ile Ser Tyr Phe His Leu
Asn Ser Glu Asp Val

29. The nucleic acid according to claim 16 having a nucleotide sequence of FIG. 4 from base 2641 to base 3009.

30. The nucleic acid according to claim 29 encoding an amino acid sequence for RL-6 which comprises:

Met Ser Asp Gln Leu Glu Ile Asp Gly Gln Arg Thr Glu Gln Leu Ile Leu
Ala Arg Arg Lys Leu Lys Gln Gln Asn Gln Glu Leu Phe Asn Leu Gln Ala
Leu His Gln Cys Lys Lys Gly Leu Phe Cys Leu Val Lys Gln Ala Glu Leu
Cys Tyr Asp Val Thr Gln Gln Gly His Glu Leu Ser Tyr Thr Leu Asn Lys
Gln Arg Gln Ser Phe Met Thr Met Val Gly Val Lys Pro Ile Lys Val Thr
Gln Gln Ser Gly Pro Val Glu Gly Ser Ile Leu Cys Gln Cys Thr Asn Ser
Glu Cys Met Tyr Thr Met Val Lys Thr Leu Cys Gly Leu Arg Glu Leu Leu
Pro Phe Asn

31. The nucleic acid of claim 4 which encodes a human Ad41 long fiber protein of 60.6 kd.

32. The nucleic acid of claim 9 which encodes a human Ad41 short fiber protein of 41.4 kd.

33. The nucleic acid of claim 19 which encodes an RL-1 protein of the Ad41 E3 region 19.4 kd.

34. The nucleic acid of claim 21 which encodes an RL-2 protein of the Ad41 E3 region 31.6 kd.

35. The nucleic acid of claim 23 which encodes an RL-3 protein of the Ad41 E3 region 6.7 kd.

36. The nucleic acid of claim 25 which encodes an RL-4 protein of the Ad41 E3 region 10.1 kd.

37. The nucleic acid of claim 27 which encodes an RL-5 protein of the Ad41 E3 region 12.3 kd.

38. The nucleic acid of claim 29 which encodes an RL-6 protein of the Ad41 E3 region of 14.0 kd.

39. The nucleic acid of claim 31 which encodes the protein comprising (a) a tail region of 42 amino acids;

(b) a shaft region of 346 amino acids; and (c) a knob region of 174 amino acids.

40. The nucleic acid of claim 32 which encodes the protein comprising (a) a tail region of 42 amino acids;

(b) a shaft region of 191 amino acids; and (c) a knob region of 154 amino acids.

* * * * *

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

Column 1, line 6: delete "Pat."

Column 12, lines 17-18: "5-aminosali-cyclic" should read as --5-aminosalicylic--.

Column 30, line 8: "TCC" should read as --TTC--

Columns 32, 33, 34, 35, 36, 37, and 38, Claim 18:

"

```
         20         30         40         50         60
    .    .     .    .     .    .     .    .     .    .     .    .
GAATTCGCGC CACTCGAAAC CAAATTTTGC TGGAGCAAGC TGCCCTGACC TCCACCCCGC
CTTAAGCGCG GTGAGCTTTG GTTTAAAACG ACCTCGTTCG ACGGGACTGG AGGTGGGGCG

         80         90        100        110        120
    .    .     .    .     .    .     .    .     .    .     .    .
GAAGTCAATT GAACCCGCCC AATTGGCCCG CTGCCCAGGT GTATCAGGAA AACCCCGCTC
CTTCAGTTAA CTTGGGCGGG TTAACCGGGC GACGGGTCCA CATAGTCCTT TTGGGGCGAG

        140        150        160        170        180
    .    .     .    .     .    .     .    .     .    .     .    .
CGACCACAGT TCTCCTGCCA CGCGACGCTG AGGCCGAAGT CCAAATGACT AACTCCGGAG
GCTGGTGTCA AGAGGACGGT GCGCTGCGAC TCCGGCTTCA GGTTTACTGA TTGAGGCCTC

        200        210        220        230        240
    .    .     .    .     .    .     .    .     .    .     .    .
CGCAATTAGC GGGCGGATCC AGACACGTCA GGTTCAGAGG TCGGTCCTCG CCCTACTCTC
GCGTTAATCG CCCGCCTAGG TCTGTGCAGT CCAAGTCTCC AGCCAGGAGC GGGATGAGAG
```

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

```
       260        270        280        290        300
CAGGTCCTAT AAAGAGGCTG ATTATCCGAG GCCGGGGTAT CCAGCTCAAC GACGAAGTGG
GTCCAGGATA TTTCTCCGAC TAATAGGCTC CGGCCCCATA GGTCGAGTTG CTGCTTCACC

       320        330        340        350        360
TGAGCTCCTT AACCGGTCTC CGACCTGACG GAGTTTTCCA GCTTGGAGGT GCCGGCCGCT
ACTCGAGGAA TTGGCCAGAG GCTGGACTGC CTCAAAAGGT CGAACCTCCA CGGCCGGCGA

       380        390        400        410        420
CCTCCTTCAC TCCTCGCCAG GCGTACCTGA CACTCCAGAG CTCTTCTTCC CAGCCTCGCT
GGAGGAAGTG AGGAGCGGTC CGCATGGACT GTGAGGTCTC GAGAAGAAGG GTCGGAGCGA

       440        450        460        470        480
CCGGCGGCAT TGGAACCCTC CAGTTTGTGG AGGAGTTTGT ACCCTCCGTT TACTTCAACC
GGCCGCCGTA ACCTTGGGAG GTCAAACACC TCCTCAAACA TGGGAGGCAA ATGAAGTTGG

       500        510        520        530        540
CATTCTCGGG CGCTCCTGGT CTTTACCCAG ACGACTTCAT CCCAAACTAC GACGCGGTGA
GTAAGAGCCC GCGAGGACCA GAAATGGGTC TGCTGAAGTA GGGTTTGATG CTGCGCCACT

       560        570        580        590        600
GCGAATCTGT GGACGGCTAC GACTGAATCC CAATGGTGCG TCCGTGACTG TGTGGCTGCA
CGCTTAGACA CCTGCCGATG CTGACTTAGG GTTACCACGC AGGCACTGAC ACACCGACGT

       620        630        640        650        660
ACATCTACAT CGGCGCCGTA ATCCTTGCTA CTTTGTCTGA AAAGTCTGTG ATTTTTACTT
TGTAGATGTA GCCGCGGCAT TAGGAACGAT GAAACAGACT TTTCAGACAC TAAAAATGAA

       680        690        700        710        720
ACCGCTCCAG CGCTTGGATT ACATGAAGAT CTGTGTTCTT TTTTGTGTGC TAAGTTTAAC
TGGCGAGGTC GCGAACCTAA TGTACTTCTA GACACAAGAA AAAACACACG ATTCAAATTG

       740        750        760        770        780
AAGTAGCCTA AGGACTTCAC CTACAACCGT TGGTTCCTTA CGTCAGCTAC AAGATTCCAC
TTCATCGGAT TCCTGAAGTG GATGTTGGCA ACCAAGGAAT GCAGTCGATG TTCTAAGGTG

       800        810        820        830        840
CAAAGGTACA CACCAAACTC TTTATTTTTC TGAGTCTACC ACTTCTATTG CACTTAACTG
GTTTCCATGT GTGGTTTGAG AAATAAAAAG ACTCAGATGG TGAAGATAAC GTGAATTGAC

       850        860        870        880        890        900
TTCTTGTCGT AACCAACTCG TTCAGTGGCG CGCTAACAGA CAATTTTGCA AACTATTTTG
AAGAACAGCA TTGGTTGAGC AAGTCACCGC GCGATTGTCT GTTAAAACGT TTGATAAAAC
```

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

| | | | | | |
|---|---|---|---|---|---|
| 910 | 920 | 930 | 940 | 950 | 960 |
| GGACGCTCTT | ATTGTTCAAG | GAAACAACAG | CCTTTGTAAC | AACTGTACTG | CTACTACTTT |
| CCTGCGAGAA | TAACAAGTTC | CTTTGTTGTC | GGAAACATTG | TTGACATGAC | GATGATGAAA |
| 970 | 980 | 990 | 1000 | 1010 | 1020 |
| AACTCTTACA | CCTCCTTTTG | TTCCCGGTCC | ATACTTGTGC | ATTGGCACAG | GAAGAGGGCC |
| TTGAGAATGT | GGAGGAAAAC | AAGGGCCAGG | TATGAACACG | TAACCGTGTC | CTTCTCCCGG |
| 1030 | 1040 | 1050 | 1060 | 1070 | 1080 |
| TAGCTGCTTT | AATCGCTGGA | CTTTACAAAA | AGAGAACCTA | ACCACTACCA | CCCTCCTTCC |
| ATCGACGAAA | TTAGCGACCT | GAAATGTTTT | TCTCTTGGAT | TGGTGATGGT | GGGAGGAAGG |
| 1090 | 1100 | 1110 | 1120 | 1130 | 1140 |
| CCTTACTACT | TATACTTTTT | CCCAAAAAAA | AATTTACTTT | TTGCCCATTA | TTGCACTTTT |
| GGAATGATGA | ATATGAAAAA | GGGTTTTTTT | TTAAATGAAA | AACGGGTAAT | AACGTGAAAA |
| 1150 | 1160 | 1170 | 1180 | 1190 | 1200 |
| GGCCTTTGTC | TGTGTTATTA | CCGCTAATTA | CATTTTAATT | TTCAATCTTG | ATAATTTTTA |
| CCGGAAACAG | ACACAATAAT | GGCGATTAAT | GTAAAATTAA | AAGTTAGAAC | TATTAAAAAT |
| 1210 | 1220 | 1230 | 1240 | 1250 | 1260 |
| CTAATCATGC | TGCTGTTTTT | ACTTTGCCTT | CTTTTCTGCT | CTGCCTATGC | CGCCGTGCCA |
| GATTAGTACG | ACGACAAAAA | TGAAACGGAA | GAAAAGACGA | GACGGATACG | GCGGCACGGT |
| 1270 | 1280 | 1290 | 1300 | 1310 | 1320 |
| GAAAAAACTC | TTAACAACCT | CGTTCGGGTG | TATGCCTTAG | TTGGTACCAA | TCTATCCCTT |
| CTTTTTTGAG | AATTGTTGGA | GCAAGCCCAC | ATACGGAATC | AACCATGGTT | AGATAGGGAA |
| 1330 | 1340 | 1350 | 1360 | 1370 | 1380 |
| GATTCTATGA | AAACTCCTCA | GATTGACGAA | CTTACTAGTC | TTAGCTGGAT | TAAACAGGAA |
| CTAAGATACT | TTTGAGGAGT | CTAACTGCTT | GAATGATCAG | AATCGACCTA | ATTTGTCCTT |
| 1390 | 1400 | 1410 | 1420 | 1430 | 1440 |
| GACAATCCTA | ACAAAAACTT | ACAATCATTT | TTTTTTATTG | GTCAAAAACT | CTGTGAAGTT |
| CTGTTAGGAT | TGTTTTTGAA | TGTTAGTAAA | AAAAAATAAC | CAGTTTTTGA | GACACTTCAA |
| 1450 | 1460 | 1470 | 1480 | 1490 | 1500 |
| ACCAAAGACA | AAATCACTGT | TTTTAACTAT | TATCCGTTGG | AATTTTCCTG | CGCTAACGTA |
| TGGTTTCTGT | TTTAGTGACA | AAAATTGATA | ATAGGCAACC | TTAAAAGGAC | GCGATTGCAT |
| 1510 | 1520 | 1530 | 1540 | 1550 | 1560 |
| ACCTTGTATT | TGTATAATCT | TAAAACTGAC | GATTCTGGCC | TCTATAATGG | AAAGGCCCAT |
| TGGAACATAA | ACATATTAGA | ATTTTGACTG | CTAAGACCGG | AGATATTACC | TTTCCGGGTA |

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

| | | | | | |
|---|---|---|---|---|---|
| 1570 | 1580 | 1590 | 1600 | 1610 | 1620 |
| ACCAAAGAGC<br>TGGTTTCTCG | TTGAACATAA<br>AACTTGTATT | CACCTATGTT<br>GTGGATACAA | AGGCTTTATG<br>TCCGAAATAC | TTATTGACAT<br>AATAACTGTA | TCCTCCGCCT<br>AGGAGGCGGA |
| 1630 | 1640 | 1650 | 1660 | 1670 | 1680 |
| AAGTGTGACA<br>TTCACACTGT | TTACTTCACG<br>AATGAAGTGC | TTACTTAGGC<br>AATGAATCCG | ATACAGGCTA<br>TATGTCCGAT | CTGGGGAAGA<br>GACCCCTTCT | TTATTGTTTA<br>AATAACAAAT |
| 1690 | 1700 | 1710 | 1720 | 1730 | 1740 |
| ATTGAAATCA<br>TAACTTTAGT | ATTGCACTAA<br>TAACGTGATT | CTCCAAATAC<br>GAGGTTTATG | CCAGCTGTGG<br>GGTCGACACC | TTAAATTTAA<br>AATTTAAATT | TGGCAGGCAA<br>ACCGTCCGTT |
| 1750 | 1760 | 1770 | 1780 | 1790 | 1800 |
| AGCAACTTCT<br>TCGTTGAAGA | ACCATTATGT<br>TGGTAATACA | TAGCGAAAAC<br>ATCGCTTTTG | GGAAACAAAG<br>CCTT[illegible]GTTTC | AACTTCCAAA<br>TTGAAGGTTT | TTTTTATGAA<br>AAAAATACTT |
| 1810 | 1820 | 1830 | 1840 | 1850 | 1860 |
| ACACACATCA<br>TGTGTGTAGT | CTGTTAATGG<br>GACAATTACC | TACCCACAAA<br>ATGGGTGTTT | AGCTTTCACT<br>TCGAAAGTGA | TTAATTACCC<br>AATTAATGGG | TTTTAACGAC<br>AAAATTGCTG |
| 1870 | 1880 | 1890 | 1900 | 1910 | 1920 |
| CTTTGTCAAA<br>GAAACAGTTT | CAACCAGCGC<br>GTTGGTCGCG | TCTACAATAT<br>AGATGTTATA | AATGACAATG<br>TTACTGTTAC | TCCAGGTAGT<br>AGGTCCATCA | CCTCATTCTT<br>GGAGTAAGAA |
| 1930 | 1940 | 1950 | 1960 | 1970 | 1980 |
| CTCATAGTAG<br>GAGTATCATC | TTGGCTTAAT<br>AACCGAATTA | AATAATTTCC<br>TTATTAAAGG | GCTAGTTTAA<br>CGATCAAATT | TATTGCTTTA<br>ATAACGAAAT | TTGCCACCGC<br>AACGGTGGCG |
| 2000 | 2010 | 2020 | 2030 | 2040 | |
| AAAAAAATCA<br>TTTTTTTAGT | AGGCCGAAGT<br>TCCGGCTTCA | TCAACATCAA<br>AGTTGTAGTT | CCAGTGCATA<br>GGTCACGTAT | TTTGTTTAGA<br>AAACAAATCT | AAAATAAAAT<br>TTTTATTTTA |
| 2060 | 2070 | 2080 | 2090 | 2100 | |
| TTTTTTCTTT<br>AAAAAAGAAA | TCAGTATGGT<br>AGTCATACCA | AACTCCTCTT<br>TTGAGGAGAA | CTCCTGCTTG<br>GAGGACGAAC | TCTGTCTGCC<br>AGACAGACGG | AATTATCTAC<br>TTAATAGATG |
| 2120 | 2130 | 2140 | 2150 | 2160 | |
| GCCTCCACCA<br>CGGAGGTGGT | CCTTCGCCGC<br>GGAAGCGGCG | AGTCTCCCAC<br>TCAGAGGGTG | CTTGATACGG<br>GAACTATGCC | ATTGTCTTCC<br>TAACAGAAGG | CGCCTTGCTG<br>GCGGAACGAC |

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

| | | | | | |
|---|---|---|---|---|---|
| 2180 | 2190 | 2200 | 2210 | 2220 | |
| ACTTATCTCA | TCTTCACCTC | TGTTTGCTGC | ACTGCCATCT | GCAGCATTGC | CACTTTTTTT |
| TGAATAGAGT | AGAAGTGGAG | ACAAACGACG | TGACGGTAGA | CGTCGTAACG | GTGAAAAAAA |
| 2240 | 2250 | 2260 | 2270 | 2280 | |
| GTGGCCATTT | TCCAAACTGC | GGACTACCTA | TACGTTAGAG | TGGCATACTA | TCGTCATCAT |
| CACCGGTAAA | AGGTTTGACG | CCTGATGGAT | ATGCAATCTC | ACCGTATGAT | AGCAGTAGTA |
| 2300 | 2310 | 2320 | 2330 | 2340 | |
| CCCCAATATA | GGAACCACGA | GGTGGCCGCC | CTTCTGTGCC | TGTCATGAAA | GTTCCTCTTC |
| GGGGTTATAT | CCTTGGTGCT | CCACCGGCGG | GAAGACACGG | ACAGTACTTT | CAAGGAGAAG |
| 2360 | 2370 | 2380 | 2390 | 2400 | |
| TCTGTCTTAT | CCTCCTTCAC | AAAGTCCTGG | CCAACTGCCA | CCTCCACCGG | CCCACCGAGT |
| AGACAGAATA | GGAGGAAGTG | TTTCAGGACC | GGTTGACGGT | GGAGGTGGCC | GGGTGGCTCA |
| 2420 | 2430 | 2440 | 2450 | 2460 | |
| TCCTGCGCTG | CTACTCAACA | GAAACCTCTT | CCTTTTGGCT | GTACTCCATT | ATTTTTATTT |
| AGGACGCGAC | GATGAGTTGT | CTTTGGAGAA | GGAAAACCGA | CATGAGGTAA | TAAAAATAAA |
| 2480 | 2490 | 2500 | 2510 | 2520 | |
| TGATTTTCTT | TGCCACCTTT | TTGGGATTAC | AAATTTACGG | CTGCCTTCAC | CTGGGCTGGA |
| ACTAAAAGAA | ACGGTGGAAA | AACCCTAATG | TTTAAATGCC | GACGGAAGTG | GACCCGACCT |
| 2540 | 2550 | 2560 | 2570 | 2580 | |
| TGCATCCTCC | CAACAACCTA | CCCAGATTTC | CTGGTTTCTT | ATTACAGCCC | CCGCCGCCCC |
| ACGTAGGAGG | GTTGTTGGAT | GGGTCTAAAG | GACCAAAGAA | TAATGTCGGG | GGCGGCGGGG |
| 2600 | 2610 | 2620 | 2630 | 2640 | |
| CACCAGCTCC | TGTACAGCGC | GCTCCATCAG | TTATTAGCTA | CTTTCATCTT | AACTCTGAAG |
| GTGGTCGAGG | ACATGTCGCG | CGAGGTAGTC | AATAATCGAT | GAAAGTAGAA | TTGAGACTTC |
| 2660 | 2670 | 2680 | 2690 | 2700 | |
| ATGTCTGACC | AACTAGAAAT | CGACGGGCAG | CGCACTGAGC | AGCTGATCCT | TGCTCGGCGA |
| TACAGACTGG | TTGATCTTTA | GCTGCCCGTC | GCGTGACTCG | TCGACTAGGA | ACGAGCCGCT |
| 2720 | 2730 | 2740 | 2750 | 2760 | |
| AAACTCAAAC | AACAAAACCA | GGAATTGTTC | AACCTTCAAG | CCTTACACCA | ATGCAAAAAG |
| TTTGAGTTTG | TTGTTTTGGT | CCTTAACAAG | TTGGAAGTTC | GGAATGTGGT | TACGTTTTTC |

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

```
         2780        2790          2800        2810         2820
    .     .      .     .       .     .     .     .      .     .      .     .
GGTCTTTTCT  GCCTGGTTAA  ACAAGCTGAA  CTTTGCTATG  ATGTAACCCA  ACAGGGGCAT
CCAGAAAAGA  CGGACCAATT  TGTTCGACTT  GAAACGATAC  TACATTGGGT  TGTCCCCGTA

         2840        2850          2860        2870         2880
    .     .      .     .       .     .     .     .      .     .      .     .
GAGCTATCAT  ACACTTTAAA  CAAGCAAAGA  CAGAGCTTTA  TGACTATGGT  GGGGGTTAAG
CTCGATAGTA  TGTGAAATTT  GTTCGTTTCT  GTCTCGAAAT  ACTGATACCA  CCCCCAATTC

         2900        2910          2920        2930         2940
    .     .      .     .       .     .     .     .      .     .      .     .
CCCATTAAGG  TTACTCAGCA  ATCCGGCCCA  GTTGAGGGAA  GCATTCTTTG  TCAGTGCACC
GGGTAATTCC  AATGAGTCGT  TAGGCCGGGT  CAACTCCCTT  CGTAAGAAAC  AGTCACGTGG

         2960        2970          2980        2990         3000
    .     .      .     .       .     .     .     .      .     .      .     .
AATTCTGAAT  GCATGTACAC  TATGGTAAAA  ACCCTGTGTG  GTCTCAGGGA  ACTTCTCCCC
TTAAGACTTA  CGTACATGTG  ATACCATTTT  TGGGACACAC  CAGAGTCCCT  TGAAGAGGGG

         3020        3030          3040        3050         3060
    .     .      .     .       .     .     .     .      .     .      .     .
TTTAATTAAA  GTTATCTGAT  TAATAAAGCT  TACCTTAAAT  TTGATATCAG  TTGTTTGTCA
AAATTAATTT  CAATAGACTA  ATTATTTCGA  ATGGAATTTA  AACTATAGTC  AACAAACAGT

         3080        3090          3100        3110         3120
    .     .      .     .       .     .     .     .      .     .      .     .
AGTTTTTCCA  GCAGCACCAC  CTGCCCTTCC  TCCCAACTTT  CGTAGGGGAT  GTGCCAACGG
TCAAAAAGGT  CGTCGTGGTG  GACGGGAAGG  AGGGTTGAAA  GCATCCCCTA  CACGGTTGCC

         3140        3150          3160        3170         3180
    .     .      .     .       .     .     .     .      .     .      .     .
GCAGCAAACT  TTCTCCACGT  CCTAAAGGGT  ATATCGGTGT  TCACCTTTTT  ACCCTGACCC
CGTCGTTTGA  AAGAGGTGCA  GGATTTCCCA  TATAGCCACA  AGTGGAAAAA  TGGGACTGGG

         3190        3200          3210        3220         3230        3240
    .     .      .     .       .     .     .     .      .     .      .     .
ACGATCTTCA  TCTTGCAGAT  GAAAAGAACC  AGAATTGAAG  ACGACTTCAA  CCCCGTCTAC
TGCTAGAAGT  AGAACGTCTA  CTTTTCTTGG  TCTTAACTTC  TGCTGAAGTT  GGGGCAGATG

         3250        3260          3270        3280         3290        3300
    .     .      .     .       .     .     .     .      .     .      .     .
CCCTATGACA  CCTTCTCAAC  TCCCAGCATC  CCCTATGTAG  CTCCGCCCTT  CGTTTCTTCT
GGGATACTGT  GGAAGAGTTG  AGGGTCGTAG  GGGATACATC  GAGGCGGGAA  GCAAAGAAGA

         3310        3320          3330        3340         3350        3360
    .     .      .     .       .     .     .     .      .     .      .     .
GACGGGTTAC  AGGAAAAACC  CCCAGGAGTT  TTAGCACTCA  AGTACACTGA  CCCCATTACT
CTGCCCAATG  TCCTTTTTGG  GGGTCCTCAA  AATCGTGAGT  TCATGTGACT  GGGGTAATGA

         3370
    .     .
ACCAATGCTA  AGC    "
TGGTTACGAT  TCG
```

should read as:

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

--

```
        10         20         30         40         50         60
    *    *     *    *     *    *     *    *     *    *     *    *
GAATTCGCGC CACTCGAAAC CAAATTTTGC TGGAGCAAGC TGCCCTGACC TCCACCCCGC
CTTAAGCGCG GTGAGCTTTG GTTTAAAACG ACCTCGTTCG ACGGGACTGG AGGTGGGGCG

        70         80         90        100        110        120
    *    *     *    *     *    *     *    *     *    *     *    *
GAAGTCAATT GAACCCGCCC AATTGGCCCG CTGCCCAGGT GTATCAGGAA AACCCCGCTC
CTTCAGTTAA CTTGGGCGGG TTAACCGGGC GACGGGTCCA CATAGTCCTT TTGGGGCGAG

       130        140        150        160        170        180
    *    *     *    *     *    *     *    *     *    *     *    *
CGACCACAGT TCTCCTGCCA CGCGACGCTG AGGCCGAAGT CCAAATGACT AACTCCGGAG
GCTGGTGTCA AGAGGACGGT GCGCTGCGAC TCCGGCTTCA GGTTTACTGA TTGAGGCCTC

       190        200        210        220        230        240
    *    *     *    *     *    *     *    *     *    *     *    *
CGCAATTAGC GGGCGGATCC AGACACGTCA GGTTCAGAGG TCGGTCCTCG CCCTACTCTC
GCGTTAATCG CCCGCCTAGG TCTGTGCAGT CCAAGTCTCC AGCCAGGAGC GGGATGAGAG

       250        260        270        280        290        300
    *    *     *    *     *    *     *    *     *    *     *    *
CAGGTCCTAT AAAGAGGCTG ATTATCCGAG GCCGGGGTAT CCAGCTCAAC GACGAAGTGG
GTCCAGGATA TTTCTCCGAC TAATAGGCTC CGGCCCCATA GGTCGAGTTG CTGCTTCACC

       310        320        330        340        350        360
    *    *     *    *     *    *     *    *     *    *     *    *
TGAGCTCCTT AACCGGTCTC CGACCTGACG GAGTTTTCCA GCTTGGAGGT GCCGGCCGCT
ACTCGAGGAA TTGGCCAGAG GCTGGACTGC CTCAAAAGGT CGAACCTCCA CGGCCGGCGA

       370        380        390        400        410        420
    *    *     *    *     *    *     *    *     *    *     *    *
CCTCCTTCAC TCCTCGCCAG GCGTACCTGA CACTCCAGAG CTCTTCTTCC CAGCCTCGCT
GGAGGAAGTG AGGAGCGGTC CGCATGGACT GTGAGGTCTC GAGAAGAAGG GTCGGAGCGA

       430        440        450        460        470        480
    *    *     *    *     *    *     *    *     *    *     *    *
CCGGCGGCAT TGGAACCCTC CAGTTTGTGG AGGAGTTTGT ACCCTCCGTT TACTTCAACC
GGCCGCCGTA ACCTTGGGAG GTCAAACACC TCCTCAAACA TGGGAGGCAA ATGAAGTTGG
```

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

```
       490        500        510        520        530        540
    *    *     *    *     *    *     *    *     *    *     *    *
CATTCTCGGG CGCTCCTGGT CTTTACCCAG ACGACTTCAT CCCAAACTAC GACGCGGTGA
GTAAGAGCCC GCGAGGACCA GAAATGGGTC TGCTGAAGTA GGGTTTGATG CTGCGCCACT

       550        560        570        580        590        600
    *    *     *    *     *    *     *    *     *    *     *    *
GCGAATCTGT GGACGGCTAC GACTGAATCC CAATGGTGCG TCCGTGACTG TGTGGCTGCA
CGCTTAGACA CCTGCCGATG CTGACTTAGG GTTACCACGC AGGCACTGAC ACACCGACGT

       610        620        630        640        650        660
    *    *     *    *     *    *     *    *     *    *     *    *
ACATCTACAT CGGCGCCGTA ATCCTTGCTA CTTTGTCTGA AAAGTCTGTG ATTTTTACTT
TGTAGATGTA GCCGCGGCAT TAGGAACGAT GAAACAGACT TTTCAGACAC TAAAAATGAA

       670        680        690        700        710        720
    *    *     *    *     *    *     *    *     *    *     *    *
ACCGCTCCAG CGCTTGGATT ACATGAAGAT CTGTGTTCTT TTTTGTGTGC TAAGTTTAAC
TGGCGAGGTC GCGAACCTAA TGTACTTCTA GACACAAGAA AAAACACACG ATTCAAATTG

       730        740        750        760        770        780
    *    *     *    *     *    *     *    *     *    *     *    *
AAGTAGCCTA AGGACTTCAC CTACAACCGT TGGTTCCTTA CGTCAGCTAC AAGATTCCAC
TTCATCGGAT TCCTGAAGTG GATGTTGGCA ACCAAGGAAT GCAGTCGATG TTCTAAGGTG

       790        800        810        820        830        840
    *    *     *    *     *    *     *    *     *    *     *    *
CAAAGGTACA CACCAAACTC TTTATTTTTC TGAGTCTACC ACTTCTATTG CACTTAACTG
GTTTCCATGT GTGGTTTGAG AAATAAAAAG ACTCAGATGG TGAAGATAAC GTGAATTGAC

       850        860        870        880        890        900
    *    *     *    *     *    *     *    *     *    *     *    *
TTCTTGTCGT AACCAACTCG TTCAGTGGCG CGCTAACAGA CAATTTTGCA AACTATTTTG
AAGAACAGCA TTGGTTGAGC AAGTCACCGC GCGATTGTCT GTTAAAACGT TTGATAAAAC

       910        920        930        940        950        960
    *    *     *    *     *    *     *    *     *    *     *    *
GGACGCTCTT ATTGTTCAAG GAAACAACAG CCTTTGTAAC AACTGTACTG CTACTACTTT
CCTGCGAGAA TAACAAGTTC CTTTGTTGTC GGAAACATTG TTGACATGAC GATGATGAAA

       970        980        990       1000       1010       1020
    *    *     *    *     *    *     *    *     *    *     *    *
AACTCTTACA CCTCCTTTTG TTCCCGGTCC ATACTTGTGC ATTGGCACAG GAAGAGGGCC
TTGAGAATGT GGAGGAAAAC AAGGGCCAGG TATGAACACG TAACCGTGTC CTTCTCCCGG
```

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

```
      1030       1040       1050       1060       1070       1080
   *     *    *     *    *     *    *     *    *     *    *     *
TAGCTGCTTT AATCGCTGGA CTTTACAAAA AGAGAACCTA ACCACTACCA CCCTCCTTCC
ATCGACGAAA TTAGCGACCT GAAATGTTTT TCTCTTGGAT TGGTGATGGT GGGAGGAAGG

      1090       1100       1110       1120       1130       1140
   *     *    *     *    *     *    *     *    *     *    *     *
CCTTACTACT TATACTTTTT CCCAAAAAAA AATTTACTTT TTGCCCATTA TTGCACTTTT
GGAATGATGA ATATGAAAAA GGGTTTTTTT TTAAATGAAA AACGGGTAAT AACGTGAAAA

      1150       1160       1170       1180       1190       1200
   *     *    *     *    *     *    *     *    *     *    *     *
GGCCTTTGTC TGTGTTATTA CCGCTAATTA CATTTTAATT TTCAATCTTG ATAATTTTTA
CCGGAAACAG ACACAATAAT GGCGATTAAT GTAAAATTAA AAGTTAGAAC TATTAAAAAT

      1210       1220       1230       1240       1250       1260
   *     *    *     *    *     *    *     *    *     *    *     *
CTAATCATGC TGCTGTTTTT ACTTTGCCTT CTTTTCTGCT CTGCCTATGC CGCCGTGCCA
GATTAGTACG ACGACAAAAA TGAAACGGAA GAAAAGACGA GACGGATACG GCGGCACGGT

      1270       1280       1290       1300       1310       1320
   *     *    *     *    *     *    *     *    *     *    *     *
GAAAAAACTC TTAACAACCT CGTTCGGGTG TATGCCTTAG TTGGTACCAA TCTATCCCTT
CTTTTTTGAG AATTGTTGGA GCAAGCCCAC ATACGGAATC AACCATGGTT AGATAGGGAA

      1330       1340       1350       1360       1370       1380
   *     *    *     *    *     *    *     *    *     *    *     *
GATTCTATGA AAACTCCTCA GATTGACGAA CTTACTAGTC TTAGCTGGAT TAAACAGGAA
CTAAGATACT TTTGAGGAGT CTAACTGCTT GAATGATCAG AATCGACCTA ATTTGTCCTT

      1390       1400       1410       1420       1430       1440
   *     *    *     *    *     *    *     *    *     *    *     *
GACAATCCTA ACAAAAACTT ACAATCATTT TTTTTTATTG GTCAAAAACT CTGTGAAGTT
CTGTTAGGAT TGTTTTTGAA TGTTAGTAAA AAAAAATAAC CAGTTTTTGA GACACTTCAA

      1450       1460       1470       1480       1490       1500
   *     *    *     *    *     *    *     *    *     *    *     *
ACCAAAGACA AAATCACTGT TTTTAACTAT TATCCGTTGG AATTTTCCTG CGCTAACGTA
TGGTTTCTGT TTTAGTGACA AAAATTGATA ATAGGCAACC TTAAAAGGAC GCGATTGCAT
```

UNITED STATES PATENT AND TRADEMARK OFFICE

CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

```
      2050       2060       2070       2080       2090       2100
         *          *          *          *          *          *
TTTTTTCTTT TCAGTATGGT AACTCCTCTT CTCCTGCTTG TCTGTCTGCC AATTATCTAC
AAAAAAGAAA AGTCATACCA TTGAGGAGAA GAGGACGAAC AGACAGACGG TTAATAGATG

      2110       2120       2130       2140       2150       2160
         *          *          *          *          *          *
GCCTCCACCA CCTTCGCCGC AGTCTCCCAC CTTGATACGG ATTGTCTTCC CGCCTTGCTG
CGGAGGTGGT GGAAGCGGCG TCAGAGGGTG GAACTATGCC TAACAGAAGG GCGGAACGAC

      2170       2180       2190       2200       2210       2220
         *          *          *          *          *          *
ACTTATCTCA TCTTCACCTC TGTTTGCTGC ACTGCCATCT GCAGCATTGC CACTTTTTTT
TGAATAGAGT AGAAGTGGAG ACAAACGACG TGACGGTAGA CGTCGTAACG GTGAAAAAAA

      2230       2240       2250       2260       2270       2280
         *          *          *          *          *          *
GTGGCCATTT TCCAAACTGC GGACTACCTA TACGTTAGAG TGGCATACTA TCGTCATCAT
CACCGGTAAA AGGTTTGACG CCTGATGGAT ATGCAATCTC ACCGTATGAT AGCAGTAGTA

      2290       2300       2310       2320       2330       2340
         *          *          *          *          *          *
CCCCAATATA GGAACCACGA GGTGGCCGCC CTTCTGTGCC TGTCATGAAA GTTCCTCTTC
GGGGTTATAT CCTTGGTGCT CCACCGGCGG GAAGACACGG ACAGTACTTT CAAGGAGAAG

      2350       2360       2370       2380       2390       2400
         *          *          *          *          *          *
TCTGTCTTAT CCTCCTTCAC AAAGTCCTGG CCAACTGCCA CCTCCACCGG CCCACCGAGT
AGACAGAATA GGAGGAAGTG TTTCAGGACC GGTTGACGGT GGAGGTGGCC GGGTGGCTCA

      2410       2420       2430       2440       2450       2460
         *          *          *          *          *          *
TCCTGCGCTG CTACTCAACA GAAACCTCTT CCTTTTGGCT GTACTCCATT ATTTTTATTT
AGGACGCGAC GATGAGTTGT CTTTGGAGAA GGAAAACCGA CATGAGGTAA TAAAAATAAA

      2470       2480       2490       2500       2510       2520
         *          *          *          *          *          *
TGATTTTCTT TGCCACCTTT TTGGGATTAC AAATTTACGG CTGCCTTCAC CTGGGCTGGA
ACTAAAAGAA ACGGTGGAAA AACCCTAATG TTTAAATGCC GACGGAAGTG GACCCGACCT
```

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

```
      2530       2540       2550       2560       2570       2580
  *    *     *    *     *    *     *    *     *    *     *    *
TGCATCCTCC CAACAACCTA CCCAGATTTC CTGGTTTCTT ATTACAGCCC CCGCCGCCCC
ACGTAGGAGG GTTGTTGGAT GGGTCTAAAG GACCAAAGAA TAATGTCGGG GGCGGCGGGG

      2590       2600       2610       2620       2630       2640
  *    *     *    *     *    *     *    *     *    *     *    *
CACCAGCTCC TGTACAGCGC GCTCCATCAG TTATTAGCTA CTTTCATCTT AACTCTGAAG
GTGGTCGAGG ACATGTCGCG CGAGGTAGTC AATAATCGAT GAAAGTAGAA TTGAGACTTC

      2650       2660       2670       2680       2690       2700
  *    *     *    *     *    *     *    *     *    *     *    *
ATGTCTGACC AACTAGAAAT CGACGGGCAG CGCACTGAGC AGCTGATCCT TGCTCGGCGA
TACAGACTGG TTGATCTTTA GCTGCCCGTC GCGTGACTCG TCGACTAGGA ACGAGCCGCT

      2710       2720       2730       2740       2750       2760
  *    *     *    *     *    *     *    *     *    *     *    *
AAACTCAAAC AACAAAACCA GGAATTGTTC AACCTTCAAG CCTTACACCA ATGCAAAAAG
TTTGAGTTTG TTGTTTTGGT CCTTAACAAG TTGGAAGTTC GGAATGTGGT TACGTTTTTC

      2770       2780       2790       2800       2810       2820
  *    *     *    *     *    *     *    *     *    *     *    *
GGTCTTTTCT GCCTGGTTAA ACAAGCTGAA CTTTGCTATG ATGTAACCCA ACAGGGGCAT
CCAGAAAAGA CGGACCAATT TGTTCGACTT GAAACGATAC TACATTGGGT TGTCCCCGTA

      2830       2840       2850       2860       2870       2880
  *    *     *    *     *    *     *    *     *    *     *    *
GAGCTATCAT ACACTTTAAA CAAGCAAAGA CAGAGCTTTA TGACTATGGT GGGGGTTAAG
CTCGATAGTA TGTGAAATTT GTTCGTTTCT GTCTCGAAAT ACTGATACCA CCCCCAATTC

      2890       2900       2910       2920       2930       2940
  *    *     *    *     *    *     *    *     *    *     *    *
CCCATTAAGG TTACTCAGCA ATCCGGCCCA GTTGAGGGAA GCATTCTTTG TCAGTGCACC
GGGTAATTCC AATGAGTCGT TAGGCCGGGT CAACTCCCTT CGTAAGAAAC AGTCACGTGG

      2950       2960       2970       2980       2990       3000
  *    *     *    *     *    *     *    *     *    *     *    *
AATTCTGAAT GCATGTACAC TATGGTAAAA ACCCTGTGTG GTCTCAGGGA ACTTCTCCCC
TTAAGACTTA CGTACATGTG ATACCATTTT TGGGACACAC CAGAGTCCCT TGAAGAGGGG
```

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

```
      3010       3020       3030       3040       3050       3060
    *    *     *    *     *    *     *    *     *    *     *    *
TTTAATTAAA GTTATCTGAT TAATAAAGCT TACCTTAAAT TTGATATCAG TTGTTTGTCA
AAATTAATTT CAATAGACTA ATTATTTCGA ATGGAATTTA AACTATAGTC AACAAACAGT

      3070       3080       3090       3100       3110       3120
    *    *     *    *     *    *     *    *     *    *     *    *
AGTTTTTCCA GCAGCACCAC CTGCCCTTCC TCCCAACTTT CGTAGGGGAT GTGCCAACGG
TCAAAAAGGT CGTCGTGGTG GACGGGAAGG AGGGTTGAAA GCATCCCCTA CACGGTTGCC

      3130       3140       3150       3160       3170       3180
    *    *     *    *     *    *     *    *     *    *     *    *
GCAGCAAACT TTCTCCACGT CCTAAAGGGT ATATCGGTGT TCACCTTTTT ACCCTGACCC
CGTCGTTTGA AAGAGGTGCA GGATTTCCCA TATAGCCACA AGTGGAAAAA TGGGACTGGG

      3190       3200       3210       3220       3230       3240
    *    *     *    *     *    *     *    *     *    *     *    *
ACGATCTTCA TCTTGCAGAT GAAAAGAACC AGAATTGAAG ACGACTTCAA CCCCGTCTAC
TGCTAGAAGT AGAACGTCTA CTTTTCTTGG TCTTAACTTC TGCTGAAGTT GGGGCAGATG
```

UNITED STATES PATENT AND TRADEMARK OFFICE
CERTIFICATE OF CORRECTION

PATENT NO. : 5,106,965

DATED : April 21, 1992

INVENTOR(S) : Norman J. Pieniazek, et al.

It is certified that error appears in the above-identified patent and that said Letters Patent is hereby corrected as shown below:

```
      1510       1520       1530       1540       1550       1560
    *    *     *    *     *    *     *    *     *    *     *    *
ACCTTGTATT TGTATAATCT TAAAACTGAC GATTCTGGCC TCTATAATGG AAAGGCCCAT
TGGAACATAA ACATATTAGA ATTTTGACTG CTAAGACCGG AGATATTACC TTTCCGGGTA

      1570       1580       1590       1600       1610       1620
    *    *     *    *     *    *     *    *     *    *     *    *
ACCAAAGAGC TTGAACATAA CACCTATGTT AGGCTTTATG TTATTGACAT TCCTCCGCCT
TGGTTTCTCG AACTTGTATT GTGGATACAA TCCGAAATAC AATAACTGTA AGGAGGCGGA

      1630       1640       1650       1660       1670       1680
    *    *     *    *     *    *     *    *     *    *     *    *
AAGTGTGACA TTACTTCACG TTACTTAGGC ATACAGGCTA CTGGGGAAGA TTATTGTTTA
TTCACACTGT AATGAAGTGC AATGAATCCG TATGTCCGAT GACCCCTTCT AATAACAAAT

      1690       1700       1710       1720       1730       1740
    *    *     *    *     *    *     *    *     *    *     *    *
ATTGAAATCA ATTGCACTAA CTCCAAATAC CCAGCTGTGG TTAAATTTAA TGGCAGGCAA
TAACTTTAGT TAACGTGATT GAGGTTTATG GGTCGACACC AATTTAAATT ACCGTCCGTT

      1750       1760       1770       1780       1790       1800
    *    *     *    *     *    *     *    *     *    *     *    *
AGCAACTTCT ACCATTATGT TAGCGAAAAC GGAAACAAAG AACTTCCAAA TTTTTATGAA
TCGTTGAAGA TGGTAATACA ATCGCTTTTG CCTTTGTTTC TTGAAGGTTT AAAAATACTT

      1810       1820       1830       1840       1850       1860
    *    *     *    *     *    *     *    *     *    *     *    *
ACACACATCA CTGTTAATGG TACCCACAAA AGCTTTCACT TTAATTACCC TTTTAACGAC
TGTGTGTAGT GACAATTACC ATGGGTGTTT TCGAAAGTGA AATTAATGGG AAAATTGCTG

      1870       1880       1890       1900       1910       1920
    *    *     *    *     *    *     *    *     *    *     *    *
CTTTGTCAAA CAACCAGCGC TCTACAATAT AATGACAATG TCCAGGTAGT CCTCATTCTT
GAAACAGTTT GTTGGTCGCG AGATGTTATA TTACTGTTAC AGGTCCATCA GGAGTAAGAA

      1930       1940       1950       1960       1970       1980
    *    *     *    *     *    *     *    *     *    *     *    *
CTCATAGTAG TTGGCTTAAT AATAATTTCC GCTAGTTTAA TATTGCTTTA TTGCCACCGC
GAGTATCATC AACCGAATTA TTATTAAAGG CGATCAAATT ATAACGAAAT AACGGTGGCG

      1990       2000       2010       2020       2030       2040
    *    *     *    *     *    *     *    *     *    *     *    *
AAAAAAATCA AGGCCGAAGT TCAACATCAA CCAGTGCATA TTTGTTTAGA AAAATAAAAT
TTTTTTTAGT TCCGGCTTCA AGTTGTAGTT GGTCACGTAT AAACAAATCT TTTTATTTTA
```

UNITED STATES PATENT AND TRADEMARK OFFICE

CERTIFICATE OF CORRECTION

PATENT NO. : 5,106,965

DATED : April 21, 1992

INVENTOR(S) : Norman J. Pieniazek, et al

It is certified that error appears in the above-indentified patent and that said Letters Patent is hereby corrected as shown below:

```
       3250       3260       3270       3280       3290       3300
     *    *     *    *     *    *     *    *     *    *     *    *
CCCTATGACA CCTTCTCAAC TCCCAGCATC CCCTATGTAG CTCCGCCCTT CGTTTCTTCT
GGGATACTGT GGAAGAGTTG AGGGTCGTAG GGGATACATC GAGGCGGGAA GCAAAGAAGA

       3310       3320       3330       3340       3350       3360
     *    *     *    *     *    *     *    *     *    *     *    *
GACGGGTTAC AGGAAAAACC CCCAGGAGTT TTAGCACTCA AGTACACTGA CCCCATTACT
CTGCCCAATG TCCTTTTTGG GGGTCCTCAA AATCGTGAGT TCATGTGACT GGGGTAATGA

       3370
     *    *
ACCAATGCTA AGC    --
TGGTTACGAT TCG
```

Signed and Sealed this

Twenty-sixth Day of July, 1994

Attest:

Bruce Lehman

BRUCE LEHMAN

*Attesting Officer*

*Commissioner of Patents and Trademarks*